US006933279B2

(12) United States Patent
Fogelman et al.

(10) Patent No.: US 6,933,279 B2
(45) Date of Patent: Aug. 23, 2005

(54) ORALLY ADMINISTERED PEPTIDES TO AMELIORATE ATHEROSCLEROSIS

(75) Inventors: Alan M. Fogelman, Beverly Hills, CA (US); Gattadahalli M. Anantharamaiah, Birmingham, AL (US); Mohamad Navab, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/896,841

(22) Filed: Jun. 29, 2001

(65) Prior Publication Data

US 2003/0045460 A1 Mar. 6, 2003

Related U.S. Application Data

(63) Continuation-in-part of application No. 09/645,454, filed on Aug. 24, 2000.

(51) Int. Cl.[7] .................. A61K 38/10; A61K 38/16; C07K 7/08; C07K 14/00
(52) U.S. Cl. ................... 514/13; 514/12; 530/324; 530/325; 530/326; 530/345
(58) Field of Search .................. 514/12, 13, 14, 514/15, 21; 530/324, 325, 326, 327, 328, 345

(56) References Cited

U.S. PATENT DOCUMENTS

| | | | |
|---|---|---|---|
| 3,767,040 A | 10/1973 | Tushaus | 428/352 |
| 4,155,913 A | 5/1979 | Hellerbach et al. | 540/560 |
| 4,643,988 A | 2/1987 | Segrest et al. | 514/12 |
| 5,344,822 A | 9/1994 | Levine et al. | 514/13 |
| 5,721,138 A | 2/1998 | Lawn | 435/325 |
| 5,733,549 A | 3/1998 | Yamada et al. | 424/185.1 |
| 5,733,879 A | 3/1998 | Rosseneu et al. | 514/13 |
| 5,814,467 A | 9/1998 | Curtiss et al. | 435/7.9 |
| 5,854,238 A | 12/1998 | Kempen | 514/220 |
| 6,004,925 A | 12/1999 | Dasseux et al. | 514/2 |
| 6,037,323 A | 3/2000 | Dasseux et al. | 514/12 |
| 6,046,166 A | 4/2000 | Dasseux et al. | 514/13 |
| 6,086,918 A | 7/2000 | Stern et al. | 424/474 |
| 6,265,377 B1 | 7/2001 | Dasseux et al. | 514/12 |
| 6,287,590 B1 | 9/2001 | Dasseux et al. | 424/450 |
| 6,329,341 B1 | 12/2001 | Dasseux et al. | 514/13 |
| 6,376,464 B1 | 4/2002 | Dasseux et al. | 514/12 |
| 6,455,088 B1 | 9/2002 | Dasseux et al. | 426/450 |
| 6,518,412 B1 | 2/2003 | Dasseux et al. | 536/23.1 |
| 6,573,239 B1 | 6/2003 | Dasseux et al. | 514/12 |
| 6,602,854 B1 | 8/2003 | Dasseux et al. | 514/13 |
| 6,630,450 B1 | 10/2003 | Dasseux et al. | 514/13 |
| 6,664,230 B1 | 12/2003 | Fogelman et al. | 814/13 |
| 6,716,816 B1 | 4/2004 | Dasseux et al. | 514/13 |
| 6,734,169 B2 | 5/2004 | Dasseux et al. | 514/12 |
| 6,753,313 B1 | 6/2004 | Dasseux et al. | 514/12 |
| 2001/0005714 A1 | 6/2001 | Boffelli et al. | 514/21 |
| 2003/0045460 A1 | 3/2003 | Fogelman et al. | 514/12 |

FOREIGN PATENT DOCUMENTS

| | | |
|---|---|---|
| IN | 185761 | 4/2004 |
| WO | WO 97/36927 | 10/1997 |
| WO | WO 97/36927 A1 | 10/1997 |
| WO | WO 99/47566 A1 | 9/1999 |

OTHER PUBLICATIONS

Anantharamaiah (1986) "Synthetic Peptide Analogs of Appolipoproteins." *Methods in Enzymology* 128:627–647.

(Continued)

*Primary Examiner*—Jeffrey Edwin Russel
(74) *Attorney, Agent, or Firm*—Quine Intellectual Property Law Group, P.C.; Tom Hunter

(57) ABSTRACT

This invention provides novel peptides that ameliorate one or more symptoms of atherosclerosis. The peptides are highly stable and readily administered via an oral route.

48 Claims, 25 Drawing Sheets

OTHER PUBLICATIONS

Anantharamaiah and Garber (1996) "Chromatographic Methods for Quantitation of Apolipoprotein A–1." *Meth. Enzymol.* 263: 267–282.

Anantharamaiah et al. (1990) "Use of Synthetic Peptide Analogues to Localize Lecithin: Cholseterol Acyltransferase Activating Domain in Apolipoprotein A–1." *Arteriosclerosis* 10:95–105.

Anantharamaiah et al. (1993) "An Atlas of the Amphipathis Helical Domains of Human Exchangeable Plasma Apolipoproteins."chapter 6: pp. 109–142 In: *The Amphipathic Helix* (Expand, R. M., ed), CRC Press, Boca Raton, FL.

Anantharamaiah et at. (1985) "Studies of Synthetic Peptide of the Amphipathic Helix." *The Journal of Biological Chemistry* 260:10248–10255.

Armstrong et al. (1993) D amino acid levels in human physiological fluids, *Chirality*, 5: 375–378.

Badimon et al. (1990) "Regression of Atherosclerotic Lesions by High Density Lipoprotein Plasma Fraction in the Cholesterol–fed Rabbit." *J. Clinical Investigation* 85:1234–1241.

Boffeli et al. (1997) "The uptake of cholesterol at the small–intestinal brush border membrane is inhibited by apolipoproteins." FEBS Letters, 411:7–11.

Borhani et al. (1999) "Crystal structure of truncated human apolipoprotein A–I suggests a lipid–bound conformation." *Proc. Natl. Acad. Sci. USA.* 94:12291–12296.

Brouillette and Anantharamaiah (1995) "Structural models of human apolipoprotein A–I." *Biochim. Biophys. Acta* 1256: 103–129.

Chung et al. (1985) "Studies of Synthetic Peptide Analogs of the Amphipathic Helix." *J. Biol. Chem.* 60(18): 10256–10262.

Davidson et al. (1994) "The Influence of Apolipoprotein Structure on the Efflux of Celluar Free Cholesterol to High Density Lipoprotein." *J. Biol. Chem.* 269(37): 22975–22982.

Dunlop and Neidle (1997) "The Orgion and Turnover of D–Serine in Brain." *Biochemical And Biophysical Research Communication* 235:26–30.

Ehara et al. (2001) "Elevated Levels of Oxidized Low Density Lipoprotein Show a Positive Relationship With the Severity of Acute Coronary Syndromes." *Circulation* 103:1955–1960.

Epand et al. (1987) "Studies Synthetic Peptide Analog of the Amphipathic Helix" *J. Biol. Chem.* 262(19): 9389–9396.

Field et al. (2001) "Gene expression of sterol regulatory element–binding proteins in hamster small intestine." *Journal of Lipid Research* 42:1–9.

Fielding and Fielding (1995) "Molecular physiology of reverse cholesterol transport." *J. Lipid Res.* 36:211–228.

Fielding et al. (1972) "A Protein of Lecithin: Cholester Acyltransferase." *Biochem. Biophys. Res. Comm.* 46(2):1492–1498.

Garber et al. (1999) "Protection against Atherosclerosis in Mice by a Synthetic Class A Amphipathic Peptide Analog of Apolipoproteins A–I." *Circulation* 100:2838.

Garber et al. (1997) *Circulation* 96–1–490.

Garber et al. (2001) "A new synthetic class A amphipathic peptide analogue protects mice from diet–induced atherosclerosis." *Journal of Lipid Research* 42:545–552.

Garber et al. (1992) "Turnover of synthetic class A amphipathic peptide analogues of exchangeable apolipoproteins in rats. Correlation with physical properties." *Arteriosclerosis and Thrombosis*, 12(8): 886–894.

Glomset (1968) "The Plasma lecithin: cholesterol acytransferase reaction." *J. Lipid Res.* 9:155–167.

Gong et al. (1994) "Structural and functional properties of human and mouse apolipoprotein A–I." *Biochim. Biophys. Acta* 1213:335–342.

Hashimoto et al. (2000) "Improvement of intestinal absorption of peptides: absorption of B1–Phe monoglucosylated insulin to rat intestinal brush–border membrane vesicles." *J. Pharmaceutics & Therapeutics* 50(2):197–204.

Hayry et al. "Stabile D–peptide analog of insulin–like growth factor–1 inhibits smooth muscle cell proliferation after carotid ballooning injury in the rat." *FASEB J.* 9(13):1336–1344 (1995).

Johnson et al. (1991) "Cholesterol transport between cells and high–density lipoproteins." *Biochim. Biophys. Acta.* 1085: 273–298.

Jonas (1991) "Lecithin–cholesterol acyltransferase in the metabolism of high–density lipoproteins." *Biochim. Biophys. Acta* 1084: 205–220.

Jonas (2000) Lecithin cholesterol acyltransferase. *Biochim. Biophys. Acta* 1529: 245–256.

Kigasawa et al. (1995) "Inhibition of corneal ulceration by tetrapeptidyl hydroxyamic acid." *Jap. J. Ophthalmology* 39(1):35–42.

Kreiger (1999) "Charting The Fate of the "Good Cholesterol": Identification and Characterization of the High–Density Lipoprotein Receptor Sr–Bi." *Ann Rev. Biochem.* 68: 523–558.

Lancet (Sep. 25, 1999) New options developed for needle–free drug delivery.

Levi et al. (2000) "A retro–inverso minantibody with anti–HIV activity." *Aids Res. & Human Retruvirus* 16(1):59–65.

Man et al. (1987) D–aspartate in human brain. *J Neurochem* 48:510–515.

Mishra et al. (1995) "Effect of the Arrangement of Tandem Repeating Units of Class A Amphipathic α–Helixes on Lipid Interaction." *J. Biol. Chem.* 270: 1602–1611.

Mishra et al. (1994) "Interaction of Synthetic Peptide Analogs of the Class A", *J. Biol. Chem.* 269: 7185–7191.

Mishra et al. (1998) Studies of Synthetic Peptides of Human Apolipoprotein A–I Containing Tandem Amphipathic α–Helixes *Biochemistry* 37: 10313–10324.

Mor et al. (1992) Enter a new post–translational modification: D–amino acids in gene–encoded peptides, *TIBS*, 17: 481–485.

Nagata et al. (1994) Distrubution of free D–serine in vertebrate brains, *Brain Res.*, 634: 291–295.

Nagata et al. (1995) Free D–serine concentration in normal and Alzheimer human brain, *Brain Res. Bull.*, 38(2): 181–183.

Navab et al. (2000) "Normal high density lipoprotein inhibits three steps in the formation of midly oxidized low density lipoprotein: step 1." *J. Lipid Res.* 41: 1481–1494.

Navab et al. (2000) "Normal high density lipoprotein inhibits three steps in the formation of mildly oxidized low density lipoprotein: steps 2 and 3." *J. Lipid Res.* 41: 1495–1508.

Nomoto et al. (1998) "Improved of intestinal abosrbtion of peptide drugs by Gyycosylation: Transport of Tetrapeptide by the Sodium Ion–Dependent D–Glucose Transporter." *J. Pharmaceutics Science* 87(3):326–332.

Ohtani et al. (1995) Age–related changes in D–aspartic acid of rat teeth, *Growth Develop. & Aging*, 59: 55–61.

Oram and Yokoyama (1996) "Apolipoprotein–mediated removal of cellular cholesterol and phospholipids." *J. Lipid Res.* 37: 2473–2491.

Paigen et al. (1990) "Atherosclerosis Susceptibility Differences among Progenitors of Recombinant Inbred Strains of Mice." *Arteriosclerosis* 10: 316–323.

Palgunachari et al. (1996) "Only the Two End Xelises of Eight Tandem Amphipathic Helical Domaine of Human Apo A–I Have Significant Lipid Affinity." *Arteriosclerosis, Thrombosis, & Vascular Biology* 16: 328–338.

Pappenheimer et al. (1997) "Absorption and Excretion of Undergradable Peptides: Rols of Lipid Solubility and Net Charge." *J. Pharmacology & Experimental Therapeutics* 280(1):292–300.

Patszty et al. (1994) "Apolipoprotein AI Transgene Corrects Apolipoprotein E Deficiency–induced Atherosclerosis in Mice." *J. Clinical Investigation* 94:899–903.

Pharmalicensing (Jan. 27, 2001) Esperion Builds a Novel Peptides Program (2 pages).

Pharmalicensing (Jan. 28, 2001) Multiple Peptide Systems Forms Joint Venture With Elan.

Pharmalicensing (Jan. 28, 2001) Unigene to Receive Patent for Delivery of Peptide Pharmaceuticals (2 pages).

Philips et al. (1993) "Plasma Lipoproteins and Progression of Cornonary Artery Disease Evaluated by Angiography and Clinical Events." *Circulation* 88: 2762–2770.

Pilone (2000) D–amino acid oxidase: new findings. *CMLS, Cell. Mol. Life Sci.*, 57: 1732–1747.

Plump et al. (1994) "Human apolipoprotein A–I gene expression increases high density lipoprotein and suppresses atherosclerosis in the apolipoprotein E–deficient mouse." *Proc. Natl. Acad. Sci.* USA 91:9607–9611.

Purdue News (Oct. 2000) 'Microspheres' Offer Promise for Oral Drug Delivery (3 pages).

Purdue News (Sep. 12, 1997) New Oral Insulin Delivery System Shows Promise (3 pages).

Reubsaet et al. (1999) "Qualitative and quantitative aspects of the degradation of several tripeptides derived from the antitumour peptide antagonist [$Arg^6$, D–$Trp^{7,9}$, $MePhe^8$] substance P(6–11)." *J. Pharmaceut. & Biomed Analysis* 19(3–4):277–284.

Rubin et al. (1991) "Inhibition of early atherogenesis in transgenic mice by human apolipoprotein AI." *Nature* 353:265–267.

Segrest et al. (1990) "Amphipathic Helc Motif: Classes and Properties." *Proteins* 8: 103–117.

Segrest et al. (1994) "The Amphipathic $\alpha$ Helix: A Multifunctional Structural Motif in Plasma Apolipoproteins." *Adv. Prot. Chem.* 45: 303–369.

Segrest et al. (2000) "Structure and function of apolipoprotein A–I and high–density lipoprotein." *Current Opin. Lipidol.* 11:105–115.

Segrest et al. (1974) "A Molecular Theory of Lipid–Protein Interaction in the Plasma Lipoproteins." *FEBS Lett.* 38:247–253.

Shah et al. (1998) "Effect of Recombinant Apolipoprotein A–$I_{Milano}$ on Aortic Atherosclerosis in Apolipoprptein E–Deficient Mice." *Circulation* 97:780–785.

Sprecher et al. (1993) "The Low HDL Cholesterol/High Triglyceride Trait." *Arterioscler. Thromb.* 13: 495–504.

Su and Amidon (1995) Investigation into the intestinal metabolism of [D–Ala] peptide T amide: Implication for oral drug delivery, *Biochim et Biophys.*, 1245:62–68.

The Wall Street Journal (Jan. 13, 2000) Emisphere technologies develops oral Heparin.

Tsai et al. (1998) D–serine added to antipsychotics for the treatment of schizophrenia. *Biol. Psychiatry*, 44: 1081–1089.

Tsimikas et al. (2001) "Measuring Circulating Oxidized Low–Density Lipoprotein to Evaluate Coronary Risk." *Circulation* 103:1930–1932.

Venkatachalapathi et al. (1993) "Effect of End Group Blockage on the Properties of a Class A Amphipathic Helical Peptied." *Proteins: Structure, Function, and Genetics* 15:349–359.

Wilson et al. (1988) "High Density Lipoprotein Cholesterol and mortality: The Framingham Heart Study." *Arteriosclerosis* 8: 737–741.

Yancy et al. (1995) "Efflux of Cellular Cholesterol and Phospholipid to Lipid–free Apolipoproteins and Class A Amphipathic Peptides." *Biochemistry*, 34: 7955–7965.

Boffelli et al. (1997) "Reconstitution and Further Characterization of the Cholesterol Transport Activity of the Small–Intestinal Brush Border Membrane" *Biochemistry* 36:10784–10792.

Bauer et al. (1982) "SMS 201–995: A Very Potent and Selective Octapeptide Analogue of Somatostatin with Prolonged Action" *Life Sciences* 31:1133–1140.

Brouillette et al. (2001) "Structural Models of Human Apolipoprotein A–I: A Critical Analysis and Review" *Biochemica et Biophyisca Acta* 55753:1–44.

Datta et al. (2001) Effects of Increasing Hydrophobicity on the Physical–Chemical and Biological Properties of a Class A Amphipathic Helical Peptide. *J Lipid Research* 42:1096–1104.

Diederich et al. (2001) "Apolipoprotein AI and $HDL_3$ Inhibit Spreading of Primary Human Monocytes through a Mechanism that Involves Cholesterol Depletion and Regulation of CD42" *Atherosclerosis* 159:313–324.

Dooley et al. (1994) "An All D–Amino Acid Opioid Peptide with Central Analgesic Activity from a Combinatorial Library" *Science* 2019–2022.

Fricker et al. (1995) "Enteral Absorption of Octreotide: Modulation of Intestinal Permeability by Distinct Carbohydrates" *The Journal of Pharmacology and Experimental Therapeutics* 274:826–832.

Fuessl et al. (1987) "Oral Absorption of the Somatostatin Analogue SMS 201–995: Theoretical and Practial Implications" *Clinical Science* 72: 255–257.

Gurfinkel et al. (2000) "Influenza Vaccine Pilot Study in Acute Coronary Syndromes and Planned Percutaneous Coronary Interventions. The Flu Vaccination Acute Coronary Syndromes (FLUVACS) Study" *Circulation* 105:2143–2147.

Hamase et al. (2001) "Determination of Free D–Proline and D–Leucine in the Brains of Mutant Mice Lacking D–Amino Acid Oxidase Activity" *Analytical Biochemistry* 298:253–258.

Hardy et al. (2001) "An Automated High–Performance Liquid Chromatography Procedure for the Quantitation of L– and D–Amino Acids by Means of Stepwise Precolum Derivatization" Analytical Biochemistry 291:297–299.

Hauser et al. (1998) "Identification of a Receptor Mediating Absorption of Dietary Cholesterol in the Intestine" *Biochemistry* 178423–17850.

Hyka et al. (2001) "Apolipoprotein A–I Inhibits the Production of Interleukin–1β and Tumor Necrosis Factor–α by Blocking Contact–Mediated Activation of Monocytes by T Lymphocytes" *Blood* 97:2381–2389.

Jones et al. (1992) "Computer Programs to Identify and Classify Amphipathic α Helical Domains" *Journal of Lipid Research* 33:287–296.

Kullman et al. (1999) "Evaluation of the Enantiomeric Composition of Amino Acids in Tobacco" *Chirality* 11:669–673.

Lundin et al. (1986) "Absorption of Intragastrically Administered DDAVP in Conscious Dogs" *Life Sciences* 38:703–709.

Merrifield et al. (1995) "Retro and Retroenantio Analogs of Cercropin–Melittin Hybrids" *Proc Natl Acad Sci USA* 92:3449–3453.

Navab et al. (2002) "Oral Administration of an Apo A–I Mimetic Peptide Synthesized from D–Amino Acids Dramatically Reduces Atherosclerosis in Mice Independent of Plasma Cholesterol" *Circulation* 105: 290–292.

Owens et al. (1990) "Apolipoprotein A–I and its Amphipathic Helix Peptide Analogues Inhibit Human Immunodeficiency Virus–Induced Syncytium Formation" *J Clin Invest* 86: 1142–1150.

Pappenheimer et al. (1994) "Intestinal Absorption and Excretion of Octapeptides Composed of D Amino Acids" *Proc Natl Acad Sci USA* 91: 1942–1945.

Peng et al. (2001) "Effects of L–glutamate, D–aspartate, and Monensin on Glycolytic and Oxidative Glucose Metabolism in Mouse Astrocyte Cultures: Further Evidence that Glutamate Uptake is Metabolically Driven by Oxidative Metabolism" *Neurochemistry International* 38:437–443.

Panizzutti et al. (2001) "A New Strategy to Decrease N–methyl–D–aspartate (NMDA) Receptor Coactivation: Inhibition of D–serine Synthesis by Converting Serine Racemase into an Eliminase" *PNAS* 98:5294–5299.

Segrest et al. (1992) "The Amphipathic Helix in the Exchangable Apolipoproteins: A Review of Secondary Structure and Function" *J Lipid Research* 33:141–166.

Sing et al. (2000) "Innate Defences Against Viraemia" *Rev Med Virol.* 10:395–403.

Srinivas et al. (1990) "Antivrial Effects of Apolipoprotein A–I and Its Synthetic Amphipathic Peptide Analogs" *Virology* 176:48–57.

Tsao et al. (2001) "Hibernation–induction Peptide and Cell Death: [D–Ala$^2$, D–Leu$^5$]enkephalin Blocks Bax–related Apoptotic Processes" *European Journal of Pharmacology* 428:149–151.

Van Lenten et al. (2001) "Acute Influenza A Infectin Promotes Increased Macrophage Infiltration into the Artery Wall that is Prevented by Apolipoprotein A–I" *Circulation* 104(suppl II):II–470. Abstract.

Canadian Pharmacists Association, Starlix General Monograph. http://cpha.infinetcomm.com/content/hcp/tools/cps_cnp_updates/starlix.cfm (2002).

Starlix MC—Aminio Acid Fact Sheet. http://www.starlix.com/media_center/content/pages/amino.htm. (2002).

Aravinda, S., Shamala, N., Das, C., Sriranjini, A., Karle, I. And Balaram, P. Aromatic–Aromatic Interactions in Crystal Structures of Helical Peptide Scaffolds Containing Projecting Phenylalinine Residues, J.Am Chem Soc. 2003; 125:5308–5315.

Ashby D, Gamble J. Vadas M, Fidge N, Siggins S, Rye K, Barter PJ. Lack of effect of serum amyloid A (SAA) on the ability of high–density lipoproteins to inhibit endothelial cell adhesion molecule expression. *Atherosclerosis.* 2001;154:113–121.

Ashby DT, Rye K–A, Clay MA., Vadas MA, Gamble J, Barter PJ. Factors influencing the ability of HDL to inhibit expression of vascular cell adhesion molecule–1 in endothelial cells. *Arteriosclerosis, Thrombosis and Vascular Biology,* 1998, 18:1450–1455.

Baker PW, Rye K–A, Gamble JR, Vadas MA, Barter PJ. Ability of reconstituted high density lipoproteins to inhibit cytokine–induced expression of vascular cell adhesion molecule–1 in human umbilical cell endothelial cells. *Journal of Lipid Research,* 1999, 40:345–353.

Baker PW, Rye KA, Gamble JR, Vadas MA, Barter PJ. Phospholipid composition of reconstituted high density lipoproteins influences their ability to inhibit endothelial cell adhesion molecule expression. *J Lipid Res* 2000;41:1261–1267.

Barter PJ, Baker PW, Rye K–A., Effect of high–density lipoproteins on the expression of adhesion molecules in endothelial cells. *Current Opinion in Lipidology,* 2002, 13:285–288.

Barter PJ, Rye K–A. High density lipoproteins and coronary heart disease. *Atherosclerosis,* 1996, 121:1–12.

Blankenberg S, Rupprecht HJ, Bickel C, Peetz D, Hafner G, Tiret L, Meyer J. Circulating cell adhesion molecules and death in patients with coronary artery disease. *Circulation* 2001;104:1336–1342.

Bourdillon MC, Poston RN, Covacho C, Chignier E, Bricca G, McGregor JL. ICAM–1 deficiency reduces atherosclerotic lesions in double–knockout mice (ApoE(–/–)/ ICMA–1(–/–)) fed a fat or a chow diet. *Arterioscler Thromb Vasc Biol* 2000;20:2630–2635.

Bowry VW, Stanley KK, Stocker R. High density lipoprotein in the major carrier of lipid hydroperoxides in human blood plasma from fasting donors. *Proc Natl Acad Sci U S A.* 1992;89:10316–10320.

Burger D, Dayer J–M. High–density lipoprotein–associated apolipoprotein A–I: the missing link between infection and chronic inflammation? *Autoimmunity Reviews* 2002;1:111–117.

Calabresi L, Franceschini G, Sirtori CR, De Palma A, Saresella M, Ferrante P, Taramelli D. Inhibition of VCAM–1 expression in endothelial cells by reconstituted high density lipoproteins. *Biochem Biophys Res Commun.* 1997;238:61–65.

Calabresi L, Gomaraschi M, Villa B, Omoboni L, Dmitrieff C, Franceschini G. Elevated cellular adhesion molecules in subjects with low HDL–cholesterol. *Arterioscler Thromb Vasc Biol.* 2002;22:656–661.

Carlos TM, Schwartz BR, Kovach NL, Yee E, Rosa M, Osborn L, Chi–Rosso G, Newman B, Lobb R, Rosso M, et al. Vascular cell adhesion molecule–1 mediates lymphocyte adherence to cytokine–activated cultured human endothelial cells. *Blood* 1990;76:965–970.

Carr AC, McCall MR, Frei B. Oxidation of LDL by myeloperoxidase and reactive nitrogen species oxidation of LDL by myeloperoxidase and reactive nitrogen species. *Arterioscler Thromb Vasc Biol.* 2000;20:1716–1723.

Castelli WP, Garrison RJ, Wilson PW, Abbott RD, Kalousdian S, Kannel WB. Incidence of coronary heart disease and lipoprotein cholesterol levels. The Framingham study. *JAMA* 1986;256:2835–2838.

Chiesa G, Monteggia E, Marchesi M, Lorenzon P, Laucello M, Lorusso V, Di Mario C, Karvouni E, Newton RS, Bisgaier CL, Franceschini G, Sirtori CR. Recombinant apolipoprotein A–I(Milano) infusion into rabbit carotid artery rapidly removes lipid from fatty streaks. *Circ Res.* 2002;90:974–980.

Christison J, Karjalainen A, Brauman J, Byrave F, Stocker R. Rapid reduction and removal of HDL– but not LDL–associated cholesteryl ester hydroperoxides by rat liver perfused in situ. *Biochem J.* 1996;314:739–742.

Clay MA, Pyle DH, Rye K–A, Vadas MA, Gamble JR, Barter PJ. Time sequence of the inhibition of endothelial adhesion molecule expression by reconstituted high density lipoproteins. *Atherosclerosis,* 2001,157:23–29.

Cockerill GW, Huehns TY, Weerasinghe A, Stocker C, Lerch PG, Miller NE, Haskard DO. Elevation of plasma high–density lipoprotein concentration reduces interleukin–1–induced expression of E–selectin in an in vivo model of acute inflammation. *rculation* 2001;103:108–112.

Cockerill GW, Rye KA, Gamble JR, Vadas MA, Barter PJ. High–density lipoproteins inhibit cytokine–induced expression of endothelial cell adhesion molecules. *Arterioscler Thromb Vasc Biol.* 1995;15:1987–1994.

Cockerill GW, Saklatvala J, Ridley SH, Yarwood H, Miller NE, Oral B, Nithyanathan S, Taylor G, Haskard DO. High–density lipoproteins differentially modulate cytokine–induced expression of E–selectin and cyclooxygenase–2. *Arterioscler Thromb Vasc. Biol.* 1999;19:910–917.

Cybulsky MI, Iiyama K, Li H, et al. A major role of VCAM–1 but not ICAM–1, in early atherosclerosis. *Journal of Clinical Investigation* 2001;107:1255–1262.

Cyrus T, Pratico D, Zhao L, Witzturn JL, Rader DJ, Rokach J, FitzGerald GA, Funk CD. Absence of 12/15–lipoxygenase expression decreases lipid peroxidation and atherogenesis in apolipoprotein E–deficient mice. *Circulation.* 2001;103:2277–2282.

Dansky HM, Barlow CB, Lominska C, Sikes JL, Kao C, Weinsaft J, Cybulsky MI, Smith JD. Adhesion of monocytes to arterial endothelium and initiation of atherosclerosis are critically dependent on vascular cell adhesion molecule–1 gene dosage. *Arterioscler Thromb Vasc Biol.* 2001;21:1662–1667.

Dansky HM, Charlton SA, Barlow CB, Tamminen M, Smith JD, Frank JS, Breslow JL. Apo A–I inhibits foam cell formation in Apo–E–deficient mice after monocyte adherence to endothelium. *J Clin Invest.* 1999;104:31–39.

Davenport P, Tipping PG. The role of interleukin–4 and interleukin–12 in the progression of atherosclerosis in apolipoprotein E–deficient mice. *Am J Pathol* 2003;163:1117–1125.

Davies MJ, Gordon JL, Gearing AJ, Pigott R, Woolf N, Katz D, Kyriakopoulos A. The expression of the adhesion molecules ICAM–1, VCAM–1, PECAM, and Eselectin in human atherosclerosis. *J Pathol* 1993;171:223–229.

De Caterina R, Bernini W. Carluccio MA, Liao JK, Libby P. Structural requirements for inhibition of cytokine–induced endothelial activation by unsaturated fatty acids. *J. Lipid Res.* 1998;39:1062–1070.

Dimayuga P, Zhu J, Oguchi S, Chyu KY, XU XO, Yano J, Shah PK, Nilsson J, Cercek B. Reconstituted HDL containing human apolipoprotein A–1 reduces VCAM–1 expression and neointima formation following periadventitial cuffinduced carotid injury in apoE null mice. *Biochem Biophys Res Commun.* 1999;264:465–468.

Epand RM, Stafford A, Leon B, Lock PE, Tytler EM, Segrest JP, Anantharamaiah GM. HDL and apolipoprotein A–I protect erythrocytes against the generation of procoagulant activity. *Arterioscler. Thromb.* 1994;14:1775–1783.

Fleisher LN, Tall AR, Whitte LD, Miller RW, Cannon PJ. Stimulation of arterial endothelial cell prostacyclin synthesis by high density lipoproteins. *J. Biol. Chem.* 1982;257:6653–6655.

Fogelman AM, Shechter I, Seager J, Hokom M, Child JS, Edwards PA. Malondialdehyde alteration of low density lipoproteins leads to cholesteryl ester accumulation in human monocyte–macrophages. *Proc Natl Acad Sci U S A.* 1980;77:2214–2218.

Fogelman AM. When good cholesterol goes bad. Nat Med 2004;10:902–903.

Forte TM, Subbanagounder G, Berliner JA, Blanche PJ, Clermont AO, Jia Z, Oda MN, Krauss RM, Bielicki JK. Altered activities of anti–atherogenic enzymes LCAT, paraoxonase, and platelet–activating factor acetylhydrolase in atherosclerosis–susceptible mice. *J. Lipid Res.* 2002;43:477–485.

Gabay C, Kushner I. Acute–phase proteins and other systemic responses to inflammation, *N. Engl. J. Med.* 1999; 340: 448–454.

Garner B, Waldeck AR, Witting PK, Rye KA, Stocker R. Oxidation of high density lipoproteins. II. Evidence for direct reduction of lipid hydroperoxides by methionine residues of apolipoproteins AI and AII. *J Biol Chem* 1998;273:6088–6095.

Garner B, Witting PK, Waldeck AR, Christison JK, Raftery M, Stocker R. Oxidation.

of high density lipoproteins. I. Formation of methionine sulfoxide in apolipoproteins AI and AII is an early event that accompanies lipid peroxidation and can be enhanced by alpha–tocopherol. *J Biol Chem* 1998;273:6080–6087.

Gaut JP, Byun J, Tran HD, Lauber WM, Carrol JA, Hotchkiss RS, Belaaouaj A, Heinecke JW. Myeloperoxidase produces nitrating oxidants in vivo. *J Clin Invest* 2002:109:1311–1319.

George J, Afek A, Shaish A, Levkovitz H, Bloom N, Cyrus T, Zhao L, Funk CD, Sigal E, Harats D. 12/15–lipoxygenase gene disruption attenuates atherogenesis in LDL receptor–deficient mice. *Circulation.* 2001;104:1646–1650.

Gordon T, Castelli WP, Hjortland MC, et al. High density lipoprotein as a protective factor against coronary heart disease. *Am. J. Med.* 1977;62: 707–714.

Harats D, Shaish A, George J, Mulkins M, Kurihara H, Levkovitz H, Sigal E. Overexpression of 15–lipoxygenase in vascular endothelium accelerates early atherosclerosis in LDL receptor–deficient mice. *Arterioscler Thromb Vasc Biol.* 2000;20:2100–2105.

Henricksen T, Mahoney EM, Steinberg D. Enhanced macrophage degradation of low density lipoprotein previously incubated with cultured endothelial cells: recognition by receptor for acetylated low density lipoproteins. *Proc Natl Acad Sci U S A.* 1981;78:6499–6503.

Hessler JR, Robertson AL, Chisolm GM. LDL–induced cytotoxicity and its inhibition by HDL in human vascular smooth muscle and endothelial cells in culture. *Atherosclerosis* 1979; 32:213–229.

Hwang SJ, Ballantyne CM, Sharrett AR, Smith LC, Davis CE, Gotto AM Jr, Boerwinkle E. Circulating adhesion molecules VCAM–1, ICAM–1, and E–selectin in carotid atherosclerosis and incident coronary heart disease cases. The atherosclerosis risk in communities (ARIC) study. *Circulation* 1997;96:4219–4225.

Jin W, Millar JS, Broedl U, et al. Inhibition of endothelial lipase causes increased HDL cholesterol levels in vivo. *J. Clin Invest* 2003:111–357–362.

Karle I., Gopi, H., and Balaram, P. Crystal structure of hydrophobic 19–residue peptide helix containing three centrally located D amino acids PNAS 2003;100:24:13946–13951.

Karle, I, Prasad, S. and Balaram, P. A combined extented and helical backbone for Boc–(Ala–Leu–Ac7C)2–OME, Peptides Res. 2004; 63:174–180.

Ko Y, Haring R, Stiebler H, Wieczorek AJ, Vetter H, Sachinidis A. Highdensity lipoprotein reduces epidermal growth factor–induced DNA synthesis in vascular smooth muscle cells. *Atherosclerosis* 1993;99: 253–259.

Kume N, Cybulsky MI, Gimbrone Jr MA. Lysophosphatidylcholine, a component of atherogenic lipoproteins, induces mononuclear leukocyte adhesion molecules in cultured human and rabbit arterial endothelial cells. *Journal of Clinical Investigation* 1992;90:1138–1144.

Lawrence MB, Springer TA. Leukocytes roll on a selectin as physiologic flow rates: distinction from and prerequisite for adhesion through integrins. *Cell* 1991;65:859–873.

Lee SH, Oe T, Blair IA. Vitamin C–induced decomposition of lipid hydroperoxides to endogenous genotoxins. *Science* 2001;292:2083–2086.

Levine DM, Parker TS, Donnelly TM, Walsh A, Rubin AL. In vivo protection against endotoxin by plasma high density lipoprotein. *Proc. Natl. Acad. Sci.* USA 1993:90 : 12040–12044.

Li H, Cybulsky MI, Gimbrone MA, Jr., Libby P. An atherogenic diet rapidly induces VCAM–1, a cytokine–regulatable mononuclear leukocyte adhesion molecule, in rabbit aortic endothelium. *Arteriosclerosis and Thrombosis* 1993;13:197–204.

Libby P, Ridker PM, Maseri A. Inflammation and atherosclerosis. *Circulation* 2002;105:1135–1143.

Mehrabian M, Allayee H, Wong J, Shi W, Wang XP, Shaposhnik Z, Funk CD, Lusis AJ, Shih W. Identification of 5–lipoxygenase as a major gene contributing to atherosclerosis susceptibility in mice. *Circ Res.* 2002;91:120–126.

Murugesan G, Sa G, Fox PL. High–density lipoprotein stimulates endothelial cell movement by a mechanism distinct from basic fibroblast growth factor. *Circ. Res.* 1994;74:1149–1156.

Nanjee MN, Doran JE, Lerch PG, Miller NE. Acute effects of intravenous infusion of apoA–I/phosphosphatidycholine discs on plasma lipoproteins in humans.. *Arterioscler Thromb Vasc Biol.* 1999;19:979–989.

Nanjee MN, Cooke CJ, Garvin R, et al. Intravenous apoA–I–lecithin discs increase pre–b–HDL concentration in tissue fluid and stimulate reverse cholesterol transport in humans. *J Lipid Res* 2001;42:1586–1593.

Navab M, Anantharamaiah GM, Reddy ST, et al. The oxidation hypothesis of atherogenesis: the role of oxidized phospholipids and HDL. *J. Lipid Res.* 2004; 45: 993–1007.

Navab M, Anantharamaiah GM, Reddy ST, et al. Oral D–4F causes formation of pre–□ high–density lipoprotein and improves high–density lipoprotein–mediated cholesterol efflux and reverse cholesterol transport from macrophages in apoE–null mice. *Circulation* 2004;109:r120–r125.

Navab M, Berliner JA, Subbanagounder G, Hama S, Lusis AJ, Castellani LW, Reddy S, Shih D, Shi W, Watson AD, Van Lenten BJ, Vora D, Fogelman AM. HDL and the inflammatory response induced response induced by LDL–derived oxidized phospholipids. *Arterioscler Thromb Vasc Biol.* 2001;21:481–488.

Navab M, Hama S, Hough G et al. Oral synthetic phospholipids (DMPC) raises high–density lipoprotein cholesterol levels, improves high–density lipoprotein function, and markedly reduces athersclerosis in apolipoprotein E–null mice. *Circulation* 2003:108:1735–1739.

Navab M, Hama SY, Gough GP, et al. A cell–free assay for detecting HDL that is dysfucntional in preventing the formation of or inactivating oxidized phospholipids. *J. Lipid Res* 2001;42:1308–1317.

Navab M, Hama–Levy, S, Van Lenten BJ, et al. Mildly oxidized LDL induces an increases apolipoprotein J/paraoxonase ratio. *J. Clin. Invest.* 1997; 99: 2205–2019.

Navab M, Imes SS, Hama SY, Hough GP, Ross LA, Bork RW, Valente AJ, Berliner JA, Drinkwater DC, Laks H,, et al. Monocyte transmigration induced by modification of low density lipoprotein in cocultures of human aortic wall cells is due to induction of monocyte chemotactic protein 1 synthesis and is abolished by high density lipoprotein. *Journal of Clinical Investigation* 1991;88:2039–2046.

Nievelstein PF, Fogelman AM, Mottino G, Frank JS. Lipid accumulation in rabbit aortic intima two hours after bolus infusion of low density lipoprotein: A deep–etch and immuno–localization study of ultra–rapidly frozen tissue. *Arteriosclerosis and Thrombosis* 1991;11:1795–1805.

Lumsden AB, Chen C, Hughes JD, Kelly AB, Hanson SR, Harker LA. Anti– VLA–4 antibody reduces intimal hyperplasia in the endarterectomized carotid artery in nonhuman primates. *J Vasc Sug* 1997;26:87–93.

Mach F, Schonbeck U, Sukhova GK, Atkinson E, Libby P. Reduction of atherosclerosis in mice by inhibition of CD40 signalling. *Nature* 1998;394:200–203.

O'Brien KD, McDonald TO, Chait A, Allen MD, Alpers CE. Neovascular expression of E–selectin, intercellular adhesion molecule–1, and vascular cell adhesion molecule–1 in human atherosclerosis and their relation to intimal leukocyte content. *Circulation* 1996;93:672–82.

O'Connell BJ, Genest J Jr. High–density lipoproteins and endothelial function. *Circulation* 2001;104:1978–1983.

Oguchi S, Dimayuga P, Zhu J, Chyu KY, Yano J, Shah PK, Nilsson J, Cercek B. Monoclonal antibody against vascular cell adhesion molecule–1 inhibits neointimal formation after periadventitial carotid artery injury in genetically hypercholesterolemic mice. *Arterioscler Thromb Vasc Biol.* 2000;20:1729–1736.

Papo N, Oren Z, Pag U, et al. The consequence of sequence alteration of an amphipathic α–helical antimicrobial peptide and its diastereomers. *J. Biol. Chem.* 2002;277(37):33912–33921.

Parthasarathy S, Santanam N. Mechanisms of oxidation antioxidants, and atherosclerosis. *Curr Opin Lipidol* 1994;5:371–375.

Pasceri V, Cheng JS, Willerson JT, Yeh ET, Chang J. Modulation of Creactive protein–meidated monocyte chemoattractant protein–1 induction in human endothelial cells by anti–atherosclerosis drugs. *Circulation.* 2001;103:2531–2534.

Pasceri V, Willerson JT, Yeh Et. Direct proinflammatory effect of C–reactive protein on human endothelial cells. *Circulation.* 2000;102:2165–2168.

Ou J, Geiger T, Zhijun O, et al. AP–4F, antennapedia peptide linked to an amphipathic α helical peptide, increases the efficiency of lipofectamine–mediated gene transfection in endothelial cells. *Biochem Biophys Res Commun* 2003;305:605–610.

Ou J, Ou Z, Jones DW, et al. L–4F, an apolipoprotein A–I mimetic, dramatically improves vasodilation in hypercholesterolemic and sickel cell disease. *Circulation* 2003;107:2337–2341.

Ou Z, Ou J, Ackerman AW et al. L–4F, an apolipoprotein A–I mimetic, restores nitric oxide and superoxide anion balance in low–density lipoprotein–treated endothelial cells. *Circulation* 2003;107:1520–1524.

Ranganathan, D, Kurur, S, Kunwar, A, Sarma, A, Vairamani, M, Karle, I. Channel–forming, self–assembling, bishelical amphiphilic peptides: design, synthesis and crystal structure of Py(Aibn)21 n=2, 3, 4. *J. Peptide Res.* 2000 56:416–426.

Reape TJ, Groot PH. Chemokines and atherosclerosis. *Atherosclerosis* 1999;147:213–225.

Reddy ST, Wadleigh DJ, Grijalva V, Ng C, Hama S, Gangopadhyay A, Shih DM, Lusis AJ, Navab M, Fogelman AM. Human paraoxonase–3 is an HDLassociated enzyme with biological activity similar to paraoxonase–1 protein but is not regulated by oxidized lipids. *Arterioscler Thromb Vasc Biol* 2001;21:542–547.

Reddy ST, Nguyen JT, Grijalva V, et al. Potential role for mitogen–activated protein kinase phosphatase–1 in the development of atherosclerotic lesion in mouse models. *Arterioscler Thromb Vasc Biol.* 2004;24:1676–1681.

Ridker PM. On evolutionary biology, inflammation, infection, and the causes of atherosclerosis. *Circulation* 2002;105:2–4.

Rong JX, Li J, Reis Ed. Choudhury RP, Dansky HM, Elmalem VI, Fallon JT, Breslow JL, Fisher EA. Elevating high–density lipoprotein cholesterol in apolipoprotein E–deficient mice remodels advanced atherosclerotic lesions by decreasing macrophage and increasing smooth muscle cell content. *Circulation* 2001;104:2447–2452.

Sattler W, Stocker R. Greater selective uptake by Hep G2 cells of highdensity lipoprotein cholesteryl ester hydroperoxides than of unoxidized cholesteryl esters. *Biochem J.* 1993;294:771–778.

Shah PK, Nilsson J, Kaul S. Effects of recombinant apolipoprotein A–I(Milano) on aortic atherosclerosis in apolipoprotein E–deficient mice. *Circulation,* 1998:97(8): 780–785.

Shah PK, Yano J, Reyes O, Chyu KY, Kaul S, Bisgaier CL, Drake S, Cercek B. High–dose recombinant apolipoproteins A–IMilano mobilizes tissue cholesterol and rapidly reduces plaque lipid and macrophage content in apolipoprotein Edeficient mice: potential implications for acute plaque stabilization. *Circulation.* 2001;103:3047–3050.

Shih D.M., Xia Y–R., Wang X–P., Miller E., Castellani L. W., Subbanagounder G., Cheroutre H., Gaull K., Berliner J.A., Witztum J.L., Lusis A.J. Combined serum paraoxonase/apolipoprotein E knockout mice exhibit increased lipoprotein oxidation and atherosclerosis. *J. Biol. Chem.,* 2000;275:17527–17535.

Shih PT, Elices MJ, Fang ZT, Ugarova TP, Strahl D, Territo MC, Frank JS, Kovach NL, Cabanas C, Berliner JA, Vora DK. Minimally modified low–density lipoprotein induces monocyte adhesion to endothelial connecting segment–1 by activating beta integrin. *J Clin Invest* 1999;103:613–625.

Shishehbor MH, Aviles RJ, Brennan ML, Fu X, Goormastic M, Pearce GL, Gokce N, Keaney JF Jr, Penn MS, Sprecher DL, Vita JA, Hazen SL. Association of nitrotyrosine levels with cardiovascular disease and modulation by statin therapy. *JAMA* 2003:289:1675–1680.

Singh IP, Baron S. Innate defences against viremia. *Rev Med Virol.* 2000;10:395–403.

Sorescu D, Szocs K, Griendling KK. NAD(P)H oxidases and their relevance to atherosclerosis. *Trends Cardiovas Med* 2001;11:124–131.

Spieker LE, Sudano I, Hurlimann D, Lerch PG, Lang MG, Binggeli C, Corti R, Ruschitzka F, Luscher TF, Noll G. High–density lipoprotein restores endothelial function in hypercholesterolemic men. *Circulation.* 2002:105:1399–1402.

Springer TA. Adhesion receptors of the immune system. *Nature* 1990;346:425–434.

Stannard AK, Khan S, Graham A, Owen JS, Allen SP. Inability of plasma high–density lipoproteins to inhibit cell adhesion molecule expression in human coronary artery endothelial cells. *Atherosclerosis* 2001;154:31–38.

Sugatani J, Miwa M, Komiyama Y, Ito S. High–density lipoprotein inhibits the synthesis of platelet–activating factor in human vascular endothelial cells. *J. Lipid Mediators Cell Signal.* 1996:13:73–88.

Tward A, Xia YR, Wang XP, Shi YS, Park C. Castellani LW, Lusis AJ, Shih DM. Decreased atherosclerotic lesion formation in human serum paraoxonase transgenic mice. *Circulation* 2002;106:484–490.

Van Lenten BJ, Jama SY, de Beer FC, Stafforini DM, McIntyre TM, Prescott SM, La Du BN, Fogelman AM, Navab M. Anti–inflammatory HDL becomes proinflammatory during the acute phase response. Loss of protective effect of HDL agains LDL oxidation in aortic wall cell cocultures. *J Clin Invest* 1995;96:2758–2767.

Van Lenten BJ, Wagner AC, Nayak DP, Hama S, Navab M, Fogelman AM. High–density lipoprotein loses its anti–inflammatory properties during acute influenza A infection. Circulation 2001;103:2283–2288.

Van Lenten BJ, Wagner AC, Anantharamaiah GM, Garber DW, Fishbein Mc, Adhikary L, Nayak DP, Hama S, Navab M, Fogelman AM. Influenza infection promotes macrophage traffic into arteries of mice that is prevented by D–4F, an apolipoprotein A–I mimetic peptide. *Circulation* 2002; 106:1127–1132.

Venugopal SK, Devaraj S, Yuhanna I, Shaul P, Jialal I. Demonstration that C-reactive protein decreases eNOS expression and bioactivity in human aortic endothelial cells. *Circulation.* 2002;106:1439–1441.

Walpola PL, Gotlieb AI, Cybulsky MI, Langille BL. Expression of ICAM-1 and VCAM-1 and monocyte adherence in arteries exposed to altered shear stress. *Arterioscler Thromb Vasc Biol* 1995;15:2–10.

Watson AD, Navab M, Hama SY, Sevanian A, Prescott SM, Stafforini DM, McIntyre TM, Du BN, Fogelman AM, Berliner JA. Effect of platelet activating factor–acetylhydrolase on the formation and action of minimally oxidized–low density lipoprotein. *J Clin Invest* 1995;95:774–782.

Watson AD, Berliner JA, Hama SY, et al. Protective effect of high density lipoprotein associated paraoxonase. Inhibition of the biological activity of minimally oxidized low density lipoprotein. *J Clin Invest* 1995;96:2882–2891.

Xia P, Vadas MA, Rye KA, Barter PJ, Gamble JR High density lipoproteins (HDL) interrupt the sphingosine kinase signaling pathway. A possible mechanism for protection against atherosclerosis by HDL. *J Biol Chem.* 1999;274-33143–33147.

Yamashita S, Maruyama T, Hirano K, et al. Molecular mechanisms, lipoprotein abnormalities and atherogenicity of hyperalphalipoproteinemia. *Atherosclerosis* 2000; 152:271–285.

Yan D, Navab M, Bruce C et al. PLTP deficiency improves the anti–inflammatory properties of HDL and reduces the ability of LDL to induce monocyte chemotactic activity. *J. Lipid Res* 2004;45:1852–1858.

Yui Y. Aoyama T, Morishita H, Takahashi M, Takatsu Y, Kawai C. Serum prostacyclin stabilizing factor is identical to apolipoprotein A–I (Apo A–I). A novel function of Apo A–I. *J. Clin. Invest.* 1998;82: 803–807.

Zeiher AM, Schachinger V. Hohnloser SH, et al. Coronary atherosclerotic wall thickening and vascular reactivity in humans. Elevated high–density lipoprotein levels ameliorate abnormal vasoconstriction in early atherosclerosis. *Circulation* 1994;89:2525–2532.

Zhang R, Brennan ML, Shen Z, MacPherson JC, Schmitt D, Molenda CE, Haze SL. Myeloperoxidase functions as a major enzymatic catalyst for initiation of lipid peroxidation at sites of inflammation. *J Biol Chem* 2002;277:46116–46122.

Zhang WJ, Stocker R, McCall MR, Forte TM, Frei B. Lack of inhibitory effect of HDL on TNFalpha–induced adhesion molecule expression in human aortic endothelial cells. *Atherosclerosis* 2002;165:241–249.

Zhao L, Cuff CA, Moss e, Wile U, Cyrus T, Klein EA, Pratico D, Rader DJ, Hunter CA, Pure E, Funk CD. Selective interleukin–12 synthesis defect in 12/15–lipoxygenase deficient macrophages associated with reduced atherosclerosis in a ouse model of familial hypercholesterolemia. *J Biol Chem* 2002;277:35350–35356.

Fig. 3A
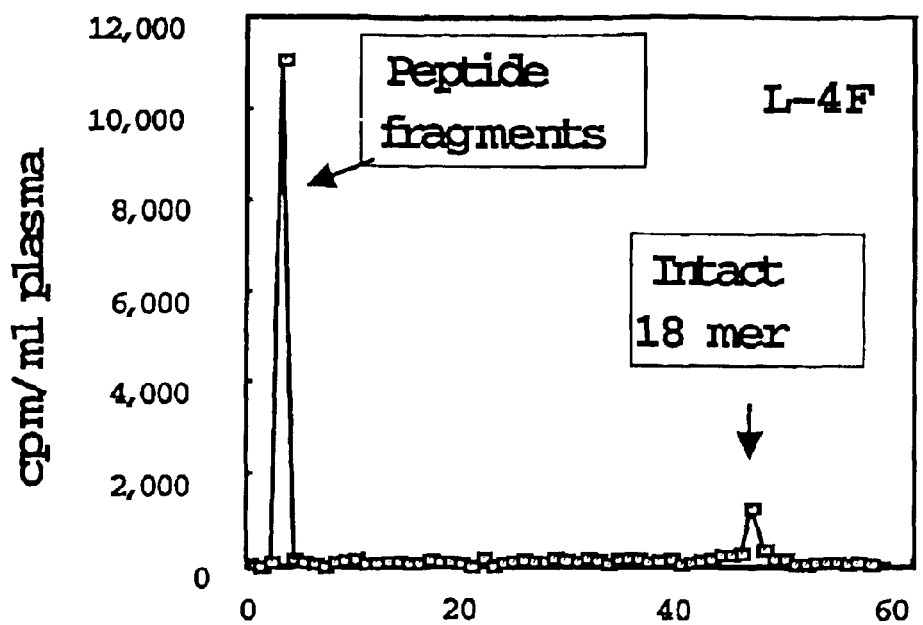
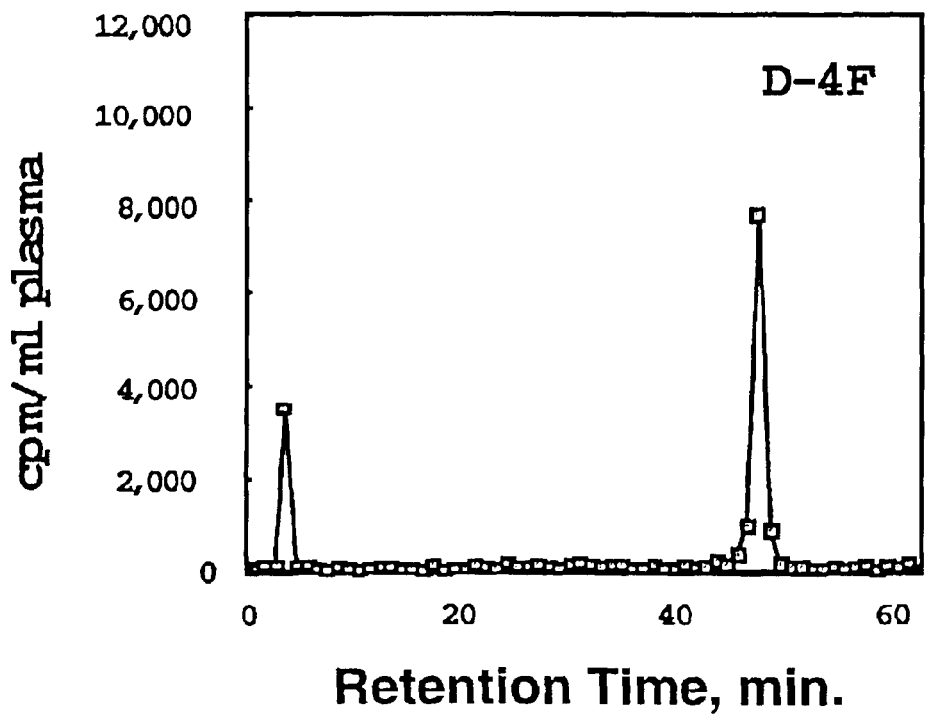
Fig. 3B

SEQUENCE LISTING

```
<160> NUMBER OF SEQ ID NOS: 86

<210> SEQ ID NO 1
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 1

Asp Trp Leu Lys Ala Phe Tyr Asp Lys Val Ala Glu Lys Leu Lys Glu
1               5                   10                  15

Ala Phe

<210> SEQ ID NO 2
```

```
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 2

Asp Trp Leu Lys Ala Phe Tyr Asp Lys Val Ala Glu Lys Leu Lys Glu
1               5                   10                  15

Ala Phe

<210> SEQ ID NO 3
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 3

Asp Trp Phe Lys Ala Phe Tyr Asp Lys Val Ala Glu Lys Leu Lys Glu
1               5                   10                  15

Ala Phe

<210> SEQ ID NO 4
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 4

Asp Trp Leu Lys Ala Phe Tyr Asp Lys Val Ala Glu Lys Phe Lys Glu
1               5                   10                  15

Ala Phe

<210> SEQ ID NO 5
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 5

Asp Trp Phe Lys Ala Phe Tyr Asp Lys Val Ala Glu Lys Phe Lys Glu
1               5                   10                  15

Ala Phe

<210> SEQ ID NO 6
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 6

Asp Trp Leu Lys Ala Phe Tyr Asp Lys Val Phe Glu Lys Phe Lys Glu
1               5                   10                  15

Phe Phe

<210> SEQ ID NO 7
<211> LENGTH: 18
<212> TYPE: PRT
<213> ORGANISM: Artificial Sequence
<220> FEATURE:
```

-continued

<223> OTHER INFORMATION: synthetic or recombinant class A peptide

<400> SEQUENCE: 7

Asp Trp Leu Lys Ala Phe Tyr Asp Lys Phe Phe Glu Lys Phe Lys Glu
1               5                   10                  15

Phe Phe

<210> SEQ ID NO 8
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 8

Asp Trp Phe Lys Ala Phe Tyr Asp Lys Phe Phe Glu Lys Phe Lys Glu
1               5                   10                  15

Phe Phe

<210> SEQ ID NO 9
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 9

Asp Trp Leu Lys Ala Phe Tyr Asp Lys Val Ala Glu Lys Leu Lys Glu
1               5                   10                  15

Phe Phe

<210> SEQ ID NO 10
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 10

Asp Trp Leu Lys Ala Phe Tyr Asp Lys Val Phe Glu Lys Phe Lys Glu
1               5                   10                  15

Ala Phe

<210> SEQ ID NO 11
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 11

Asp Trp Leu Lys Ala Phe Tyr Asp Lys Val Phe Glu Lys Leu Lys Glu
1               5                   10                  15

Phe Phe

<210> SEQ ID NO 12
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 12

-continued

Asp Trp Leu Lys Ala Phe Tyr Asp Lys Val Ala Glu Lys Phe Lys Glu
1               5                   10                  15

Phe Phe

<210> SEQ ID NO 13
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 13

Asp Trp Leu Lys Ala Phe Tyr Asp Lys Val Phe Glu Lys Phe Lys Glu
1               5                   10                  15

Phe Phe

<210> SEQ ID NO 14
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 14

Glu Trp Leu Lys Leu Phe Tyr Glu Lys Val Leu Glu Lys Phe Lys Glu
1               5                   10                  15

Ala Phe

<210> SEQ ID NO 15
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 15

Glu Trp Leu Lys Ala Phe Tyr Asp Lys Val Ala Glu Lys Phe Lys Glu
1               5                   10                  15

Ala Phe

<210> SEQ ID NO 16
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 16

Glu Trp Leu Lys Ala Phe Tyr Asp Lys Val Ala Glu Lys Leu Lys Glu
1               5                   10                  15

Phe Phe

<210> SEQ ID NO 17
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 17

Glu Trp Leu Lys Ala Phe Tyr Asp Lys Val Phe Glu Lys Phe Lys Glu
1               5                   10                  15

Ala Phe

```
<210> SEQ ID NO 18
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 18

Glu Trp Leu Lys Ala Phe Tyr Asp Lys Val Phe Glu Lys Leu Lys Glu
1               5                   10                  15

Phe Phe

<210> SEQ ID NO 19
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 19

Glu Trp Leu Lys Ala Phe Tyr Asp Lys Val Ala Glu Lys Phe Lys Glu
1               5                   10                  15

Phe Phe

<210> SEQ ID NO 20
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 20

Glu Trp Leu Lys Ala Phe Tyr Asp Lys Val Phe Glu Lys Phe Lys Glu
1               5                   10                  15

Phe Phe

<210> SEQ ID NO 21
<211> LENGTH: 14
<212> TYPE: PRT
<213> ORGANISM: Artificial Sequence
<220> FEATURE:
<223> OTHER INFORMATION: synthetic or recombinant class A peptide

<400> SEQUENCE: 21

Ala Phe Tyr Asp Lys Val Ala Glu Lys Leu Lys Glu Ala Phe
1               5                   10

<210> SEQ ID NO 22
<211> LENGTH: 14
<212> TYPE: PRT
<213> ORGANISM: Artificial Sequence
<220> FEATURE:
<223> OTHER INFORMATION: synthetic or recombinant class A peptide

<400> SEQUENCE: 22

Ala Phe Tyr Asp Lys Val Ala Glu Lys Phe Lys Glu Ala Phe
1               5                   10

<210> SEQ ID NO 23
<211> LENGTH: 14
<212> TYPE: PRT
<213> ORGANISM: Artificial Sequence
<220> FEATURE:
<223> OTHER INFORMATION: synthetic or recombinant class A peptide
```

```
<400> SEQUENCE: 23

Ala Phe Tyr Asp Lys Val Ala Glu Lys Phe Lys Glu Ala Phe
1               5                   10

<210> SEQ ID NO 24
<211> LENGTH: 14
<212> TYPE: PRT
<213> ORGANISM: Artificial Sequence
<220> FEATURE:
<223> OTHER INFORMATION: synthetic or recombinant class A peptide

<400> SEQUENCE: 24

Ala Phe Tyr Asp Lys Phe Phe Glu Lys Phe Lys Glu Phe Phe
1               5                   10

<210> SEQ ID NO 25
<211> LENGTH: 14
<212> TYPE: PRT
<213> ORGANISM: Artificial Sequence
<220> FEATURE:
<223> OTHER INFORMATION: synthetic or recombinant class A peptide

<400> SEQUENCE: 25

Ala Phe Tyr Asp Lys Phe Phe Glu Lys Phe Lys Glu Phe Phe
1               5                   10

<210> SEQ ID NO 26
<211> LENGTH: 14
<212> TYPE: PRT
<213> ORGANISM: Artificial Sequence
<220> FEATURE:
<223> OTHER INFORMATION: synthetic or recombinant class A peptide

<400> SEQUENCE: 26

Ala Phe Tyr Asp Lys Val Ala Glu Lys Phe Lys Glu Ala Phe
1               5                   10

<210> SEQ ID NO 27
<211> LENGTH: 14
<212> TYPE: PRT
<213> ORGANISM: Artificial Sequence
<220> FEATURE:
<223> OTHER INFORMATION: synthetic or recombinant class A peptide

<400> SEQUENCE: 27

Ala Phe Tyr Asp Lys Val Ala Glu Lys Leu Lys Glu Phe Phe
1               5                   10

<210> SEQ ID NO 28
<211> LENGTH: 14
<212> TYPE: PRT
<213> ORGANISM: Artificial Sequence
<220> FEATURE:
<223> OTHER INFORMATION: synthetic or recombinant class A peptide

<400> SEQUENCE: 28

Ala Phe Tyr Asp Lys Val Phe Glu Lys Phe Lys Glu Ala Phe
1               5                   10

<210> SEQ ID NO 29
<211> LENGTH: 14
<212> TYPE: PRT
<213> ORGANISM: Artificial Sequence
<220> FEATURE:
<223> OTHER INFORMATION: synthetic or recombinant class A peptide
```

```
<400> SEQUENCE: 29

Ala Phe Tyr Asp Lys Val Phe Glu Lys Leu Lys Glu Phe Phe
1               5                   10

<210> SEQ ID NO 30
<211> LENGTH: 14
<212> TYPE: PRT
<213> ORGANISM: Artificial Sequence
<220> FEATURE:
<223> OTHER INFORMATION: synthetic or recombinant class A peptide

<400> SEQUENCE: 30

Ala Phe Tyr Asp Lys Val Ala Glu Lys Phe Lys Glu Phe Phe
1               5                   10

<210> SEQ ID NO 31
<211> LENGTH: 14
<212> TYPE: PRT
<213> ORGANISM: Artificial Sequence
<220> FEATURE:
<223> OTHER INFORMATION: synthetic or recombinant class A peptide

<400> SEQUENCE: 31

Lys Ala Phe Tyr Asp Lys Val Phe Glu Lys Phe Lys Glu Phe
1               5                   10

<210> SEQ ID NO 32
<211> LENGTH: 14
<212> TYPE: PRT
<213> ORGANISM: Artificial Sequence
<220> FEATURE:
<223> OTHER INFORMATION: synthetic or recombinant class A peptide

<400> SEQUENCE: 32

Leu Phe Tyr Glu Lys Val Leu Glu Lys Phe Lys Glu Ala Phe
1               5                   10

<210> SEQ ID NO 33
<211> LENGTH: 14
<212> TYPE: PRT
<213> ORGANISM: Artificial Sequence
<220> FEATURE:
<223> OTHER INFORMATION: synthetic or recombinant class A peptide

<400> SEQUENCE: 33

Ala Phe Tyr Asp Lys Val Ala Glu Lys Phe Lys Glu Ala Phe
1               5                   10

<210> SEQ ID NO 34
<211> LENGTH: 14
<212> TYPE: PRT
<213> ORGANISM: Artificial Sequence
<220> FEATURE:
<223> OTHER INFORMATION: synthetic or recombinant class A peptide

<400> SEQUENCE: 34

Ala Phe Tyr Asp Lys Val Ala Glu Lys Leu Lys Glu Phe Phe
1               5                   10

<210> SEQ ID NO 35
<211> LENGTH: 14
<212> TYPE: PRT
<213> ORGANISM: Artificial Sequence
<220> FEATURE:
<223> OTHER INFORMATION: synthetic or recombinant class A peptide

<400> SEQUENCE: 35
```

Ala Phe Tyr Asp Lys Val Phe Glu Lys Phe Lys Glu Ala Phe
1               5                   10

<210> SEQ ID NO 36
<211> LENGTH: 14
<212> TYPE: PRT
<213> ORGANISM: Artificial Sequence
<220> FEATURE:
<223> OTHER INFORMATION: synthetic or recombinant class A peptide

<400> SEQUENCE: 36

Ala Phe Tyr Asp Lys Val Phe Glu Lys Leu Lys Glu Phe Phe
1               5                   10

<210> SEQ ID NO 37
<211> LENGTH: 14
<212> TYPE: PRT
<213> ORGANISM: Artificial Sequence
<220> FEATURE:
<223> OTHER INFORMATION: synthetic or recombinant class A peptide

<400> SEQUENCE: 37

Ala Phe Tyr Asp Lys Val Ala Glu Lys Phe Lys Glu Phe Phe
1               5                   10

<210> SEQ ID NO 38
<211> LENGTH: 14
<212> TYPE: PRT
<213> ORGANISM: Artificial Sequence
<220> FEATURE:
<223> OTHER INFORMATION: synthetic or recombinant class A peptide

<400> SEQUENCE: 38

Ala Phe Tyr Asp Lys Val Phe Glu Lys Phe Lys Glu Phe Phe
1               5                   10

<210> SEQ ID NO 39
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 39

Asp Trp Leu Lys Ala Leu Tyr Asp Lys Val Ala Glu Lys Leu Lys Glu
1               5                   10                  15

Ala Leu

<210> SEQ ID NO 40
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 40

Asp Trp Phe Lys Ala Phe Tyr Glu Lys Val Ala Glu Lys Leu Lys Glu
1               5                   10                  15

Phe Phe

<210> SEQ ID NO 41
<211> LENGTH: 18
<212> TYPE: PRT
<213> ORGANISM: Artificial Sequence
<220> FEATURE:

<223> OTHER INFORMATION: synthetic or recombinant class A peptide

<400> SEQUENCE: 41

Asp Trp Phe Lys Ala Phe Tyr Glu Lys Phe Phe Glu Lys Phe Lys Glu
1               5                   10                  15
Phe Phe

<210> SEQ ID NO 42
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 42

Glu Trp Leu Lys Ala Leu Tyr Glu Lys Val Ala Glu Lys Leu Lys Glu
1               5                   10                  15
Ala Leu

<210> SEQ ID NO 43
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 43

Glu Trp Leu Lys Ala Phe Tyr Glu Lys Val Ala Glu Lys Leu Lys Glu
1               5                   10                  15
Ala Phe

<210> SEQ ID NO 44
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 44

Glu Trp Phe Lys Ala Phe Tyr Glu Lys Val Ala Glu Lys Leu Lys Glu
1               5                   10                  15
Phe Phe

<210> SEQ ID NO 45
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 45

Glu Trp Leu Lys Ala Phe Tyr Glu Lys Val Phe Glu Lys Phe Lys Glu
1               5                   10                  15
Phe Phe

<210> SEQ ID NO 46
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 46

```
Glu Trp Leu Lys Ala Phe Tyr Glu Lys Phe Phe Glu Lys Phe Lys Glu
1               5                   10                  15

Phe Phe

<210> SEQ ID NO 47
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 47

Glu Trp Phe Lys Ala Phe Tyr Glu Lys Phe Phe Glu Lys Phe Lys Glu
1               5                   10                  15

Phe Phe

<210> SEQ ID NO 48
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 48

Asp Phe Leu Lys Ala Trp Tyr Asp Lys Val Ala Glu Lys Leu Lys Glu
1               5                   10                  15

Ala Trp

<210> SEQ ID NO 49
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 49

Glu Phe Leu Lys Ala Trp Tyr Glu Lys Val Ala Glu Lys Leu Lys Glu
1               5                   10                  15

Ala Trp

<210> SEQ ID NO 50
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 50

Asp Phe Trp Lys Ala Trp Tyr Asp Lys Val Ala Glu Lys Leu Lys Glu
1               5                   10                  15

Trp Trp

<210> SEQ ID NO 51
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 51

Glu Phe Trp Lys Ala Trp Tyr Glu Lys Val Ala Glu Lys Leu Lys Glu
1               5                   10                  15

Trp Trp
```

<210> SEQ ID NO 52
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 52

Asp Lys Leu Lys Ala Phe Tyr Asp Lys Val Phe Glu Trp Ala Lys Glu
1               5                   10                  15

Ala Phe

<210> SEQ ID NO 53
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 53

Asp Lys Trp Lys Ala Val Tyr Asp Lys Phe Ala Glu Ala Phe Lys Glu
1               5                   10                  15

Phe Leu

<210> SEQ ID NO 54
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 54

Glu Lys Leu Lys Ala Phe Tyr Glu Lys Val Phe Glu Trp Ala Lys Glu
1               5                   10                  15

Ala Phe

<210> SEQ ID NO 55
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 55

Glu Lys Trp Lys Ala Val Tyr Glu Lys Phe Ala Glu Ala Phe Lys Glu
1               5                   10                  15

Phe Leu

<210> SEQ ID NO 56
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 56

Asp Trp Leu Lys Ala Phe Val Asp Lys Phe Ala Glu Lys Phe Lys Glu
1               5                   10                  15

Ala Tyr

<210> SEQ ID NO 57
<211> LENGTH: 18

<212> TYPE: PRT
<213> ORGANISM: Artificial Sequence
<220> FEATURE:
<223> OTHER INFORMATION: synthetic or recombinant class A peptide

<400> SEQUENCE: 57

Glu Lys Trp Lys Ala Val Tyr Glu Lys Phe Ala Glu Ala Phe Lys Glu
1               5                   10                  15
Phe Leu

<210> SEQ ID NO 58
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 58

Asp Trp Leu Lys Ala Phe Val Tyr Asp Lys Val Phe Lys Leu Lys Glu
1               5                   10                  15
Phe Phe

<210> SEQ ID NO 59
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 59

Glu Trp Leu Lys Ala Phe Val Tyr Glu Lys Val Phe Lys Leu Lys Glu
1               5                   10                  15
Phe Phe

<210> SEQ ID NO 60
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 60

Asp Trp Leu Arg Ala Phe Tyr Asp Lys Val Ala Glu Lys Leu Lys Glu
1               5                   10                  15
Ala Phe

<210> SEQ ID NO 61
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 61

Glu Trp Leu Arg Ala Phe Tyr Glu Lys Val Ala Glu Lys Leu Lys Glu
1               5                   10                  15
Ala Phe

<210> SEQ ID NO 62
<211> LENGTH: 18
<212> TYPE: PRT
<213> ORGANISM: Artificial Sequence
<220> FEATURE:
<223> OTHER INFORMATION: synthetic or recombinant class A peptide

```
<400> SEQUENCE: 62

Asp Trp Leu Lys Ala Phe Tyr Asp Arg Val Ala Glu Lys Leu Lys Glu
1               5                   10                  15

Ala Phe

<210> SEQ ID NO 63
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 63

Glu Trp Leu Lys Ala Phe Tyr Glu Arg Val Ala Glu Lys Leu Lys Glu
1               5                   10                  15

Ala Phe

<210> SEQ ID NO 64
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 64

Asp Trp Leu Lys Ala Phe Tyr Asp Lys Val Ala Glu Arg Leu Lys Glu
1               5                   10                  15

Ala Phe

<210> SEQ ID NO 65
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 65

Glu Trp Leu Lys Ala Phe Tyr Glu Lys Val Ala Glu Arg Leu Lys Glu
1               5                   10                  15

Ala Phe

<210> SEQ ID NO 66
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 66

Asp Trp Leu Lys Ala Phe Tyr Asp Lys Val Ala Glu Lys Leu Arg Glu
1               5                   10                  15

Ala Phe

<210> SEQ ID NO 67
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 67

Glu Trp Leu Lys Ala Phe Tyr Glu Lys Val Ala Glu Lys Leu Arg Glu
```

-continued

```
                1               5                  10                 15
Ala Phe

<210> SEQ ID NO 68
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 68

Asp Trp Leu Lys Ala Phe Tyr Asp Arg Val Ala Glu Arg Leu Lys Glu
1               5                  10                 15

Ala Phe

<210> SEQ ID NO 69
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 69

Glu Trp Leu Lys Ala Phe Tyr Glu Arg Val Ala Glu Arg Leu Lys Glu
1               5                  10                 15

Ala Phe

<210> SEQ ID NO 70
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 70

Asp Trp Leu Arg Ala Phe Tyr Asp Lys Val Ala Glu Lys Leu Arg Glu
1               5                  10                 15

Ala Phe

<210> SEQ ID NO 71
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 71

Glu Trp Leu Arg Ala Phe Tyr Glu Lys Val Ala Glu Lys Leu Arg Glu
1               5                  10                 15

Ala Phe

<210> SEQ ID NO 72
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 72

Asp Trp Leu Arg Ala Phe Tyr Asp Arg Val Ala Glu Lys Leu Lys Glu
1               5                  10                 15

Ala Phe
```

```
<210> SEQ ID NO 73
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 73

Glu Trp Leu Arg Ala Phe Tyr Glu Arg Val Ala Glu Lys Leu Lys Glu
1               5                   10                  15

Ala Phe

<210> SEQ ID NO 74
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 74

Asp Trp Leu Lys Ala Phe Tyr Asp Lys Val Ala Glu Arg Leu Arg Glu
1               5                   10                  15

Ala Phe

<210> SEQ ID NO 75
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 75

Glu Trp Leu Lys Ala Phe Tyr Glu Lys Val Ala Glu Arg Leu Arg Glu
1               5                   10                  15

Ala Phe

<210> SEQ ID NO 76
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 76

Asp Trp Leu Arg Ala Phe Tyr Asp Lys Val Ala Glu Arg Leu Lys Glu
1               5                   10                  15

Ala Phe

<210> SEQ ID NO 77
<211> LENGTH: 18
<212> TYPE: PRT
<213> ORGANISM: Artificial Sequence
<220> FEATURE:
<223> OTHER INFORMATION: synthetic or recombinant class A peptide

<400> SEQUENCE: 77

Glu Trp Leu Arg Ala Phe Tyr Glu Lys Val Ala Glu Arg Leu Lys Glu
1               5                   10                  15

Ala Phe

<210> SEQ ID NO 78
<211> LENGTH: 37
<212> TYPE: PRT
```

<213> ORGANISM: Artificial Sequence
<220> FEATURE:
<223> OTHER INFORMATION: synthetic or recombinant class A peptide

<400> SEQUENCE: 78

Asp Trp Leu Lys Ala Phe Tyr Asp Lys Val Ala Glu Lys Leu Lys Glu
1               5                   10                  15

Ala Phe Pro Asp Trp Leu Lys Ala Phe Tyr Asp Lys Val Ala Glu Lys
            20                  25                  30

Leu Lys Glu Ala Phe
        35

<210> SEQ ID NO 79
<211> LENGTH: 37
<212> TYPE: PRT
<213> ORGANISM: Artificial Sequence
<220> FEATURE:
<223> OTHER INFORMATION: synthetic or recombinant class A peptide

<400> SEQUENCE: 79

Asp Trp Leu Lys Ala Phe Tyr Asp Lys Val Ala Glu Lys Leu Lys Glu
1               5                   10                  15

Phe Phe Pro Asp Trp Leu Lys Ala Phe Tyr Asp Lys Val Ala Glu Lys
            20                  25                  30

Leu Lys Glu Phe Phe
        35

<210> SEQ ID NO 80
<211> LENGTH: 37
<212> TYPE: PRT
<213> ORGANISM: Artificial Sequence
<220> FEATURE:
<223> OTHER INFORMATION: synthetic or recombinant class A peptide

<400> SEQUENCE: 80

Asp Trp Phe Lys Ala Phe Tyr Asp Lys Val Ala Glu Lys Leu Lys Glu
1               5                   10                  15

Ala Phe Pro Asp Trp Phe Lys Ala Phe Tyr Asp Lys Val Ala Glu Lys
            20                  25                  30

Leu Lys Glu Ala Phe
        35

<210> SEQ ID NO 81
<211> LENGTH: 37
<212> TYPE: PRT
<213> ORGANISM: Artificial Sequence
<220> FEATURE:
<223> OTHER INFORMATION: synthetic or recombinant class A peptide

<400> SEQUENCE: 81

Asp Lys Leu Lys Ala Phe Tyr Asp Lys Val Phe Glu Trp Ala Lys Glu
1               5                   10                  15

Ala Phe Pro Asp Lys Leu Lys Ala Phe Tyr Asp Lys Val Phe Glu Trp
            20                  25                  30

Leu Lys Glu Ala Phe
        35

<210> SEQ ID NO 82
<211> LENGTH: 37
<212> TYPE: PRT
<213> ORGANISM: Artificial Sequence
<220> FEATURE:
<223> OTHER INFORMATION: synthetic or recombinant class A peptide

<400> SEQUENCE: 82

Asp Lys Trp Lys Ala Val Tyr Asp Lys Phe Ala Glu Ala Phe Lys Glu
1               5                   10                  15

Phe Leu Pro Asp Lys Trp Lys Ala Val Tyr Asp Lys Phe Ala Glu Ala
            20                  25                  30

Phe Lys Glu Phe Leu
            35

<210> SEQ ID NO 83
<211> LENGTH: 37
<212> TYPE: PRT
<213> ORGANISM: Artificial Sequence
<220> FEATURE:
<223> OTHER INFORMATION: synthetic or recombinant class A peptide

<400> SEQUENCE: 83

Asp Trp Phe Lys Ala Phe Tyr Asp Lys Val Ala Glu Lys Phe Lys Glu
1               5                   10                  15

Ala Phe Pro Asp Trp Phe Lys Ala Phe Tyr Asp Lys Val Ala Glu Lys
            20                  25                  30

Phe Lys Glu Ala Phe
            35

<210> SEQ ID NO 84
<211> LENGTH: 37
<212> TYPE: PRT
<213> ORGANISM: Artificial Sequence
<220> FEATURE:
<223> OTHER INFORMATION: synthetic or recombinant class A peptide

<400> SEQUENCE: 84

Asp Trp Leu Lys Ala Phe Val Tyr Asp Lys Val Phe Lys Leu Lys Glu
1               5                   10                  15

Phe Phe Pro Asp Trp Leu Lys Ala Phe Val Tyr Asp Lys Val Phe Lys
            20                  25                  30

Leu Lys Glu Phe Phe
            35

<210> SEQ ID NO 85
<211> LENGTH: 37
<212> TYPE: PRT
<213> ORGANISM: Artificial Sequence
<220> FEATURE:
<223> OTHER INFORMATION: synthetic or recombinant class A peptide

<400> SEQUENCE: 85

Asp Trp Leu Lys Ala Phe Tyr Asp Lys Phe Ala Glu Lys Phe Lys Glu
1               5                   10                  15

Phe Phe Pro Asp Trp Leu Lys Ala Phe Tyr Asp Lys Phe Ala Glu Lys
            20                  25                  30

Phe Lys Glu Phe Phe
            35

<210> SEQ ID NO 86
<211> LENGTH: 18
<212> TYPE: PRT
<213> ORGANISM: Artificial Sequence
<220> FEATURE:
<223> OTHER INFORMATION: synthetic or recombinant class A peptide
<220> FEATURE:
<221> NAME/KEY: misc_feature
<222> LOCATION: (1)..(1)

```
<223> OTHER INFORMATION: Xaa is aspartic acid or glutamic acid, or
      homologues or analogues thereo
<220> FEATURE:
<221> NAME/KEY: misc_feature
<222> LOCATION: (8)..(8)
<223> OTHER INFORMATION: Xaa is aspartic acid or glutamic acid, or
      homologues or analogues thereo
<220> FEATURE:
<221> NAME/KEY: misc_feature
<222> LOCATION: (12)..(12)
<223> OTHER INFORMATION: Xaa is aspartic acid or glutamic acid, or
      homologues or analogues thereo
<220> FEATURE:
<221> NAME/KEY: misc_feature
<222> LOCATION: (16)..(16)
<223> OTHER INFORMATION: Xaa is aspartic acid or glutamic acid, or
      homologues or analogues thereo
<220> FEATURE:
<221> NAME/KEY: misc_feature
<222> LOCATION: (2)..(3)
<223> OTHER INFORMATION: Xaa is tryptophan, phenylalanine, alanine,
      leucine, tyrosine, isoleucine, valine or alpha-naphthylalanine,
      or homologues or analogues thereo
<220> FEATURE:
<221> NAME/KEY: misc_feature
<222> LOCATION: (6)..(7)
<223> OTHER INFORMATION: Xaa is tryptophan, phenylalanine, alanine,
      leucine, tyrosine, isoleucine, valine or alpha-naphthylalanine,
      or homologues or analogues thereo
<220> FEATURE:
<221> NAME/KEY: misc_feature
<222> LOCATION: (10)..(11)
<223> OTHER INFORMATION: Xaa is tryptophan, phenylalanine, alanine,
      leucine, tyrosine, isoleucine, valine or alpha-naphthylalanine,
      or homologues or analogues thereo
<220> FEATURE:
<221> NAME/KEY: misc_feature
<222> LOCATION: (14)..(14)
<223> OTHER INFORMATION: Xaa is tryptophan, phenylalanine, alanine,
      leucine, tyrosine, isoleucine, valine or alpha-naphthylalanine,
      or homologues or analogues thereo
<220> FEATURE:
<221> NAME/KEY: misc_feature
<222> LOCATION: (17)..(18)
<223> OTHER INFORMATION: Xaa is tryptophan, phenylalanine, alanine,
      leucine, tyrosine, isoleucine, valine or alpha-naphthylalanine,
      or homologues or analogues thereo
<220> FEATURE:
<221> NAME/KEY: misc_feature
<222> LOCATION: (4)..(4)
<223> OTHER INFORMATION: Xaa is lysine or arginine
<220> FEATURE:
<221> NAME/KEY: misc_feature
<222> LOCATION: (9)..(9)
<223> OTHER INFORMATION: Xaa is lysine or arginine
<220> FEATURE:
<221> NAME/KEY: misc_feature
<222> LOCATION: (13)..(13)
<223> OTHER INFORMATION: Xaa is lysine or arginine
<220> FEATURE:
<221> NAME/KEY: misc_feature
<222> LOCATION: (15)..(15)
<223> OTHER INFORMATION: Xaa is lysine or arginine
<220> FEATURE:
<221> NAME/KEY: misc_feature
<222> LOCATION: (5)..(5)
<223> OTHER INFORMATION: Xaa is serine, threonine, alanine, glycine,
      histidine, or homologues or analogues thereo

<400> SEQUENCE: 86

Xaa Xaa Xaa Xaa Xaa Xaa Xaa Xaa Xaa Xaa Xaa Xaa Xaa Xaa Xaa Xaa
1               5                   10                  15

Xaa Xaa
```

ORALLY ADMINISTERED PEPTIDES TO AMELIORATE ATHEROSCLEROSIS

CROSS-REFERENCE TO RELATED APPLICATIONS

This application is a continuation-in-part of U.S. Ser. No. 09/645,454, filed on Aug. 24, 2000, which is incorporated herein by reference in its entirety for all purposes.

STATEMENT AS TO RIGHTS TO INVENTIONS MADE UNDER FEDERALLY SPONSORED RESEARCH AND DEVELOPMENT

This work was supported by United States Public Health Service and National Heart, Lung, and Blood Institute Grants HL30568 and HL34343. The Government of the United States of America may have certain rights in this invention.

FIELD OF THE INVENTION

This invention relates to the field of atherosclerosis. In particular, this invention pertains to the identification of a class of peptides that are orally administrable and that ameliorate one or more symptoms of atherosclerosis.

BACKGROUND OF THE INVENTION

Cardiovascular disease is a leading cause of morbidity and mortality, particularly in the United States and in Western European countries. Several causative factors are implicated in the development of cardiovascular disease including hereditary predisposition to the disease, gender, lifestyle factors such as smoking and diet, age, hypertension, and hyperlipidemia, including hypercholesterolemia. Several of these factors, particularly hyperlipidemia and hypercholesteremia (high blood cholesterol concentrations) provide a significant risk factor associated with atherosclerosis.

Cholesterol is present in the blood as free and esterified cholesterol within lipoprotein particles, commonly known as chylomicrons, very low density lipoproteins (VLDLs), low density lipoproteins (LDLs), and high density lipoproteins (HDLs). Concentration of total cholesterol in the blood is influenced by (1) absorption of cholesterol from the digestive tract, (2) synthesis of cholesterol from dietary constituents such as carbohydrates, proteins, fats and ethanol, and (3) removal of cholesterol from blood by tissues, especially the liver, and subsequent conversion of the cholesterol to bile acids, steroid hormones, and biliary cholesterol.

Maintenance of blood cholesterol concentrations is influenced by both genetic and environmental factors. Genetic factors include concentration of rate-limiting enzymes in cholesterol biosynthesis, concentration of receptors for low density lipoproteins in the liver, concentration of rate-limiting enzymes for conversion of cholesterols bile acids, rates of synthesis and secretion of lipoproteins and gender of person. Environmental factors influencing the hemostasis of blood cholesterol concentration in humans include dietary composition, incidence of smoking, physical activity, and use of a variety of pharmaceutical agents. Dietary variables include amount and type of fat (saturated and polyunsaturated fatty acids), amount of cholesterol, amount and type of fiber, and perhaps amounts of vitamins such as vitamin C and D and minerals such as calcium.

Epidemiological studies show an inverse correlation of high density lipoprotein (HDL) and apolipoprotein (apo) A-I levels with the occurrence of atherosclerotic events (Wilson et al. (1988) *Arteriosclerosis* 8: 737–741). Injection of HDL into rabbits fed an atherogenic diet has been shown to inhibit atherosclerotic lesion formation (Badimon et al. (1990) *J. Clin. Invest.* 85: 1234–1241).

Human apo A-I has been a subject of intense study because of its anti-atherogenic properties. Exchangeable apolipoproteins, including apo A-I, possess lipid-associating domains (Brouillette and Anantharamaiah (1995) *Biochim. Biophys. Acta* 1256:103–129; Segrest et al. (1974) *FEBS Lett.* 38::247–253). Apo A-I has been postulated to possess eight tandem repeating 22 mer sequences, most of which have the potential to form class A amphipathic helical structures (Segrest et al. (1974) *FEBS Lett.* 38: :247–253). Characteristics of the class A amphipathic helix include the presence of positively charged residues at the polar-nonpolar interface and negatively charged residues at the center of the polar face (Segrest et al. (1974) FEBS Lett. 38: 247–253; Segrest et al. (1990) *Proteins: Structure, Function, and Genetics* 8: 103–117). Apo A-I has been shown to strongly associate with phospholipids to form complexes and to promote cholesterol efflux from cholesterol-enriched cells. The delivery and maintenance of serum levels of apo A-I to effectively mitigate one or more symptoms of atherosclerosis has heretofore proven elusive.

SUMMARY OF THE INVENTION

This invention provides novel peptides administration of which mitigate one or more symptoms of atherosclerosis. In particular, it was a discovery of this invention that peptides comprising a class A amphipathic helix when formulated with "D" amino acid residue(s) and/or having protected amino and carboxyl termini can be orally administered to an organism, are readily taken up and delivered to the serum, and are effective to mitigate one or more symptoms of atherosclerosis.

Thus, in one embodiment, this invention provides a peptide that ameliorates a symptom of atherosclerosis, where the peptide ranges in length from about 10 to about 30 amino acids, comprises at least one class A amphipathic helix, comprises at least one "D" amino acid residue, protects a phospholipid against oxidation by an oxidizing agent, and is not the D-18A peptide (e.g. D-W-L-K-A-F-Y-D-K-V-A-E-K-L-K-E-A-F (SEQ ID NO: 1) having all D form amino acid residues). In particularly preferred embodiments, the peptide further comprises a protecting group coupled to the amino and/or carboxyl terminus. Preferred protecting groups include, but are not limited to acetyl, amide, and 3 to 20 carbon alkyl groups, Fmoc, t-boc, 9-fluoreneacetyl group, 1-fluorenecarboxylic group, 9-florenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethylbenzenesulphonyl (Mtr), Mesitylene-2-sulphonyl (Mts), 4,4-dimethoxybenzhydryl (Mbh),Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), Benzyloxymethyl (Bom), t-butoxycarbonyl (Boc), cyclohexyloxy (cHxO),t-butoxymethyl (Bum), t-butoxy (tBuO), t-Butyl (tBu), Acetyl (Ac), and Trifluoroacetyl (TFA). In certain particularly preferred embodiments the peptide further comprises a first protecting group coupled to the amino terminus and a second protecting group coupled to the carboxyl terminus. Particularly preferred peptides comprise greater than about 50% amino acid sequence identity with human or mouse apo A-I or with the polypeptide encoded by the exon encoding a class A amphipathic helix of human or mouse apo A-1. In certain preferred embodiments, at least 50%, more preferably at least 75%, and most preferably at least 90% and even 100% of the enantiomeric amino acids are "D" amino acids. The peptide may be combined with a pharmacologically acceptable excipient (e.g. an excipient suitable for oral administration to a mammal).

In certain particularly preferred embodiments, the peptide comprises one or more of the following amino acid sequences: D-W-L-K-A-F-Y-D-K-V-A-E-K-L-K-E-A-F (SEQ ID NO: 2), D-W-F-K-A-F-Y-D-K-V-A-E-K-L-K-E-A-F (SEQ-ID-NO:3), D-W-L-K-A-F-Y-D-K-V-A-E-K-F-K-E-A-F (SEQ-ID-NO:4), D-W-F-K-A-F-Y-D-K-V-A-E-K-F-K-E-A-F(SEQ-ID-NO:5), D-W-L-K-A-F-Y-D-K-F-F-E-K-F-K-E-F-F (SEQ-ID-NO:6), D-W-F-K-A-F-Y-D-K-F-F-E-K-F-K-E-F-F (SEQ-ID-NO:7), D-W-L-K-A-F-Y-D-K-V-A-E-K-F-K-E-A-F (SEQ-ID-NO:8), D-W-L-K-A-F-Y-D-K-V-A-E-K-L-K-E-F-F (SEQ-ID-NO:9), D-W-L-K-A-F-Y-D-K-V-F-E-K-F-K-E-A-F (SEQ-ID-NO:10), D-W-L-K-A-F-Y-D-K-V-F-E-K-L-K-E-F-F (SEQ-ID-NO:11), D-W-L-K-A-F-Y-D-K-V-A-E-K-F-K-E-F-F (SEQ-ID-NO: 12), D-W-L-K-A-F-Y-D-K-V-F-E-K-F-K-E-F-F (SEQ-ID-NO: 13), E-W-L-K-L-F-Y-E-K-V-L-E-K-F-K-E-A-F (SEQ-ID-NO:14), E-W-L-K-A-F-Y-D-K-V-A-E-K-F-K-E-A-F (SEQ-ID-NO:15), E-W-L-K-A-F-Y-D-K-V-A-E-K-L-K-E-F-F (SEQ-ID-NO:16), E-W-L-K-A-F-Y-D-K-V-F-E-K-F-K-E-A-F (SEQ-ID-NO: 17), E-W-L-K-A-F-Y-D-K-V-F-E-K-L-K-E-F-F (SEQ-ID-NO:18), E-W-L-K-A-F-Y-D-K-V-A-E-K-F-K-E-F-F (SEQ-ID-NO:19), E-W-L-K-A-F-Y-D-K-V-F-E-K-F-K-E-F-F (SEQ ID NO: 20), and A-F-Y-D-K-V-A-E-K-L-K-E-A-F (SEQ ID NO: 21), A-F-Y-D-K-V-A-E-K-F-K-E-A-F (SEQ ID NO:22), A-F-Y-D-K-V-A-E-K-F-K-E-A-F (SEQ ID NO:23), A-F-Y-D-K-F-F-E-K-F-K-E-F-F (SEQ ID NO:24), A-F-Y-D-K-F-F-E-K-F-K-E-F-F (SEQ ID NO:25), A-F-Y-D-K-V-A-E-K-F-K-E-A-F (SEQ ID NO:26), A-F-Y-D-K-V-A-E-K-L-K-E-F-F (SEQ ID NO:27), A-F-Y-D-K-V-F-E-K-F-K-E-A-F (SEQ ID NO:28), A-F-Y-D-K-V-F-E-K-L-K-E-F-F (SEQ ID NO:29), A-F-Y-D-K-V-A-E-K-F-K-E-F-F (SEQ ID NO:30), K-A-F-Y-D-K-V-F-E-K-F-K-E-F (SEQ ID NO:31), L-F-Y-E-K-V-L-E-K-F-K-E-A-F (SEQ ID NO:32), A-F-Y-D-K-V-A-E-K-F-K-E-A-F (SEQ ID NO:33), A-F-Y-D-K-V-A-E-K-L-K-E-F-F (SEQ ID NO:34), A-F-Y-D-K-V-F-E-K-F-K-E-A-F (SEQ ID NO:35), A-F-Y-D-K-V-F-E-K-L-K-E-F-F (SEQ ID NO:36), A-F-Y-D-K-V-A-E-K-F-K-E-F-F (SEQ ID NO:37), A-F-Y-D-K-V-F-E-K-F-K-E-F-F (SEQ ID NO:38), D-W-L-K-A-L-Y-D-K-V-A-E-K-L-K-E-A-L (SEQ ID NO:39), D-W-F-K-A-F-Y-E-K-V-A-E-K-L-K-E-F-F (SEQ ID NO:40), D-W-F-K-A-F-Y-E-K-F-F-E-K-F-K-E-F-F (SEQ ID NO:41), E-W-L-K-A-L-Y-E-K-V-A-E-K-L-K-E-A-L (SEQ ID NO:42), E-W-L-K-A-F-Y-E-K-V-A-E-K-L-K-E-A-F (SEQ ID NO:43), E-W-F-K-A-F-Y-E-K-V-A-E-K-L-K-E-F-F (SEQ ID NO:44), E-W-L-K-A-F-Y-E-K-V-F-E-K-F-K-E-F-F (SEQ ID NO:45), E-W-L-K-A-F-Y-E-K-F-F-E-K-F-K-E-F-F (SEQ ID NO:46), E-W-F-K-A-F-Y-E-K-F-F-E-K-F-K-E-F-F (SEQ ID NO:47), D-F-L-K-A-W-Y-D-K-V-A-E-K-L-K-E-A-W (SEQ ID NO:48), E-F-L-K-A-W-Y-E-K-V-A-E-K-L-K-E-A-W (SEQ ID NO:49), D-F-W-K-A-W-Y-D-K-V-A-E-K-L-K-E-W-W (SEQ ID NO:50), E-F-W-K-A-W-Y-E-K-V-A-E-K-L-K-E-W-W (SEQ ID NO:51), D-K-L-K-A-F-Y-D-K-V-F-E-W-A-K-E-A-F (SEQ ID NO:52), D-K-W-K-A-V-Y-D-K-F-A-E-A-F-K-E-F-L (SEQ ID NO:53), E-K-L-K-A-F-Y-E-K-V-F-E-W-A-K-E-A-F (SEQ ID NO:54), E-K-W-K-A-V-Y-E-K-F-A-E-A-F-K-E-F-L (SEQ ID NO:55), D-W-L-K-A-F-V-D-K-F-A-E-K-F-K-E-A-Y (SEQ ID NO:56), E-K-W-K-A-V-Y-E-K-F-A-E-A-F-K-E-F-L (SEQ ID NO:57), D-W-L-K-A-F-V-Y-D-K-V-F-K-L-K-E-F-F (SEQ ID NO:58), E-W-L-K-A-F-V-Y-E-K-V-F-K-L-K-E-F-F (SEQ ID NO:59), D-W-L-R-A-F-Y-D-K-V-A-E-K-L-K-E-A-F (SEQ ID NO:60), E-W-L-R-A-F-Y-E-K-V-A-E-K-L-K-E-A-F (SEQ ID NO:61), D-W-L-K-A-F-Y-D-R-V-A-E-K-L-K-E-A-F (SEQ ID NO:62), E-W-L-K-A-F-Y-E-R-V-A-E-K-L-K-E-A-F (SEQ ID NO:63), D-W-L-K-A-F-Y-D-K-V-A-E-R-L-K-E-A-F (SEQ ID NO:64), E-W-L-K-A-F-Y-E-K-V-A-E-R-L-K-E-A-F (SEQ ID NO:65), D-W-L-K-A-F-Y-D-K-V-A-E-K-L-R-E-A-F (SEQ ID NO:66), E-W-L-K-A-F-Y-E-K-V-A-E-K-L-R-E-A-F (SEQ ID NO:67), D-W-L-K-A-F-Y-D-R-V-A-E-R-L-K-E-A-F (SEQ ID NO:68), E-W-L-K-A-F-Y-E-R-V-A-E-R-L-K-E-A-F (SEQ ID NO:69), D-W-L-R-A-F-Y-D-K-V-A-E-K-L-R-E-A-F (SEQ ID NO:70), E-W-L-R-A-F-Y-E-K-V-A-E-K-L-R-E-A-F (SEQ ID NO:71), D-W-L-R-A-F-Y-D-R-V-A-E-K-L-K-E-A-F (SEQ ID NO:72), E-W-L-R-A-F-Y-E-R-V-A-E-K-L-K-E-A-F (SEQ ID NO:73), D-W-L-K-A-F-Y-D-K-V-A-E-R-L-R-E-A-F (SEQ ID NO:74), E-W-L-K-A-F-Y-E-K-V-A-E-R-L-R-E-A-F (SEQ ID NO:75), D-W-L-R-A-F-Y-D-K-V-A-E-R-L-K-E-A-F (SEQ ID NO:76), E-W-L-R-A-F-Y-E-K-V-A-E-R-L-K-E-A-F (SEQ ID NO:77), D-W-L-K-A-F-Y-D-K-V-A-E-K-L-K-E-A-F-P-D-W-L-K-A-F-Y-D-K-V-A-E-K-L-K-E-A-F (SEQ ID NO:78), D-W-L-K-A-F-Y-D-K-V-A-E-K-L-K-E-F-F-P-D-W-L-K-A-F-Y-D-K-V-A-E-K-L-K-E-F-F (SEQ ID NO:79), D-W-F-K-A-F-Y-D-K-V-A-E-K-L-K-E-A-F-P-D-W-F-K-A-F-Y-D-K-V-A-E-K-L-K-E-A-F (SEQ ID NO:80), D-K-L-K-A-F-Y-D-K-V-F-E-W-A-K-E-A-F-P-D-K-L-K-A-F-Y-D-K-V-F-E-W-L-K-E-A-F (SEQ ID NO:81), D-K-W-K-A-V-Y-D-K-F-A-E-A-F-K-E-F-L-P-D-K-W-K-A-V-Y-D-K-F-A-E-A-F-K-E-F-L (SEQ ID NO:82), D-W-F-K-A-F-Y-D-K-V-A-E-K-F-K-E-A-F-P-D-W-F-K-A-F-Y-D-K-V-A-E-K-F-K-E-A-F (SEQ ID NO:83), D-W-L-K-A-F-V-Y-D-K-V-F-K-L-K-E-F-F-P-D-W-L-K-A-F-V-Y-D-K-V-F-K-L-K-E-F-F (SEQ ID NO:84), D-W-L-K-A-F-Y-D-K-F-A-E-K-F-K-E-F-F-P-D-W-L-K-A-F-Y-D-K-F-A-E-K-F-K-E-F-F (SEQ ID NO:85), truncations of the above sequences, multimeric combinations (e.g. preferably ranging from dimers to trimers, tetramers, 5 mers, 8 mers, or 10 mers) of the above sequences, conservative substitutions of the above sequences, and/or the above sequences comprising amino acid analogs. The enantiomeric amino acids of such sequences preferably comprise at least one "D" amino acid. In certain preferred embodiments, at least 50%, more preferably at lease 75%, and most preferably at least 90% and even 100% of the enantiomeric amino acids are "D" amino acids as described herein. Such peptides can also include a protecting group (e.g., amide, acetyl, propeonyl, and a 3 to 20 carbon alkyl, etc.) coupled to the amino or carboxyl terminus. In certain embodiments, the protecting group coupled to the carboxyl terminus is an amide. In certain embodiments, the protecting group coupled to the amino terminus is an acetyl, a propeonyl, or a 3 to 20 carbon alkyl. Certain peptides comprise both a carboxyl- and an amino-terminus protecting group. In one such embodiment, the amino terminus protecting group is a protecting group selected from the group consisting of acetyl, propeonyl, and a 3 to 20 carbon alkyl; and the carboxyl terminal protecting group is an amide.

In certain embodiments, the peptide is one that protects a phospholipid against oxidation by an oxidizing agent selected from the group consisting of lipids such as hydrogen peroxide, 13(S)-HPODE, 15(S)-HPETE, HPODE, HPETE, HODE, and HETE. The phospholipid can be a phospholipid selected from the group consisting of 1-palmitoyl-2-arachidonoyl-sn-glycero-3-phos- phorylcholine (PAPC), 1-stearoyl-2-arachidonoyl-sn-glycero-3-phosphorylcholine (SAPC)), 1-stearoyl-2-arachidonyl-sn-glycero-3-phosphorylethanolamine (SAPE). Thus the peptide prevents the formation of lipids such as oxidized 1-palmitoyl-2-arachidonoyl-sn-glycero-3-phosphorylcholine (Ox-PAPC), 1-palmitoyl-2-oxovaleroyl-sn-glycero-3-phosphorylcholine (POVPC), 1-palmitoyl-2-glutaroyl-sn-glycero-3-phosphorylcholine (PGPC), 1-palmitoyl-2-epoxyisoprostane-sn-glycero-3-phosphorylcholine (PEIPC), oxidized 1-stearoyl-2-arachidonoyl-sn-glycero-3-phosphorylcholine (Ox-SAPC), 1-stearoyl-2-oxovaleroyl-sn-glycero-3-phosphorylcholine (SOVPC), 1-stearoyl-2-glutaroyl-sn-glycero-3-phosphorylcholine (SGPC), 1-stearoyl-2-epoxyisoprostane-sn-glycero-3-phosphorylcholine (SEIPC), oxidized 1-stearoyl-2-arachidonyl-sn-glycero-3-phosphorylethanolamine (Ox-SAPE), 1-stearoyl-2-oxovaleroyl-sn-glycero-3-phosphorylethanolamine (SOVPE), 1-stearoyl-2-glutaroyl-sn-glycero-3-phosphorylethanolamine (SGPE), and 1-stearoyl-2-epoxyisoprostane-sn-glycero-3-phosphorylethanolamine(SEI PE).

In another embodiment, this invention provides a composition, suitable for oral administration, that ameliorates a symptom of atherosclerosis. The composition comprises a peptide that is a human apo A-I peptide or fragment thereof comprising a class A amphipathic helix, or an analogue of a human apo A-I peptide wherein said peptide has a first protecting group attached to an amino terminal and a second protecting group attached to a carboxyl terminal and further wherein said peptide comprises a plurality of D amino acid residues. The protecting groups include, but are not limited to the protecting groups described herein. In certain embodiments, more than half, more preferably more than 80%, and most preferably more than 90% or even all of the enantiomeric amino acids comprising the peptide are D amino acids. The composition can further comprise a pharmaceutically acceptable excipient (e.g., an excipient suitable for oral administration or an excipient suitable for injection). Preferred peptides are capable of protecting a phospholipid [e.g., 1-palmitoyl-2-arachidonoyl-sn-glycero-3-phosphorycholine (PAPC), 1-stearoyl-2-arachidonoyl-sn-glycero-3- phosphorylcholine (SAPC)), 1- stearoyl-2-arachidonyl-sn-glycero-3-phosphorylethanolamine (SAPE)] from oxidization by an oxidizing agent (e.g. hydrogen peroxide, 13(S)-HPODE, 15(S)-HPETE, HPODE, HPETE, HODE, and HETE). Thus the peptide prevents the formation of oxidized 1-palmitoyl-2-arachidonoyl-sn-glycero-3-phosphorylcholine (Ox-PAPC), 1-palmitoyl-2-oxovaleroyl-sn-glycero-3-phosphorylcholine (POVPC), 1-palmitoyl-2-glutaroyl-sn-glycero-3-phosphorylcholine (PGPC), 1-palmitoyl-2-epoxyisoprostane-sn-glycero-3-phosphorylcholine (PEIPC), oxidized 1-stearoyl-2-arachidonoyl-sn-glycero-3-phosphorylcholine (Ox-SAPC), 1-stearoyl-2-oxovaleroyl-sn-glycero-3-phosphorylcholine (SOVPC), 1-stearoyl-2-glutaroyl-sn-glycero-3-phosphorylcholine (SGPC), 1-stearoyl-2-epoxyisoprostane-sn-glycero-3-phosphorylcholine (SEIPC), oxidized 1-stearoyl-2-arachidonyl-sn-glycero-3-phosphorylethanolamine (Ox-SAPE), 1-stearoyl-2-oxovaleroyl-sn-glycero-3-phosphorylethanolamine (SOVPE), 1-stearoyl-2-glutaroyl-sn-glycero-3-phosphorylethanolamine (SGPE), and 1-stearoyl-2-epoxyisoprostane-sn-glycero-3-phosphorylethanolamine(SEI PE).

This invention also provides methods of ameliorating a symptom of atherosclerosis. The methods comprise administering to an organism (e.g. human or non-human mammal) one or more of the peptides described herein. In particularly preferred embodiments, such peptides comprise a plurality of "D" amino acids and/or are protected as described herein. The peptide is preferably orally administered to the organism and the organism is preferably an organism diagnosed as having or as at risk for one or more symptoms of atherosclerosis. In certain embodiments, the peptide can be provided as an isolated peptide or combined with a pharmacological excipient as described herein. The administration is preferably at a dosage sufficient to ameliorate one or more symptoms of atherosclerosis and/or to significantly reduce the likelihood of occurrence of one or more symptoms of atherosclerosis.

In still another embodiment, this invention provides a kit for ameliorating a symptom of atherosclerosis. Preferred kits include a container containing one or more of the peptides described herein. The peptides preferably comprise a plurality of "D" amino acids and/or are protected as described herein. In certain embodiments, the kit can optionally further include a pharmaceutically acceptable excipient and/or the peptide is provided combined with a with a pharmaceutically acceptable excipient (e.g. in a unit dosage formulation). Preferred kits provided the peptide(s) as a unit dosage formulation is for oral administration. The kits also, optionally, include instructional materials teaching the use of said peptide for ameliorating one or more symptoms of atherosclerosis and/or for reducing the likelihood of occurrence of one or more symptoms of atherosclerosis.

In certain embodiments, this invention excludes any one or more peptides disclosed in U.S. Pat. No. 3,767,040 and/or in Garber et al. (1992) *Arteriosclerosis and Thrombosis*, 12: 886–894. In preferred embodiments, this invention excludes peptides having the formula $A_1$-$B_1$-$B_2$-$C_1$-D-$B_3$-$B_4$-$A_2$-$C_2$-$B_5$-$B_6$-$A_3$-$C_3$-$B_7$-$C_4$-$A_4$-$B_8$-$B_9$ (SEQ ID NO:86) wherein $A_1$, $A_2$, $A_3$ and $A_4$ are independently aspartic acid or glutainic acid, or homologues or analogues thereof; $B_1$, $B_2$, $B_3$, $B_4$, $B_5$, $B_6$, $B_7$, $B_8$ and $B_9$ are independently tryptophan, phenylalanine, alanine, leucine, tyrosine, isoleucine, valine or α-naphthylalanine, or homologues or analogues thereof; $C_1$, $C_2$, $C_3$ and $C_4$ are independently lysine or arginine, and D is serine, threonine, alanine, glycine, histidine, or homologues or analogues thereof; provided that, when $A_1$ and $A_2$ are aspartic acid, $A_3$ and $A_4$ are glutamic acid, $B_2$ and $B_9$ are leucine, $B_3$ and $B_7$ are phenylalanine, $B_4$ is tyrosine, $B_5$ is valine, $B_6$, $B_8$, and D are alanine, and $C_1$, $C_2$, $C_3$ and $C_4$ are lysine, $B_1$ is not tryptophan.

Definitions

The terms "polypeptide", "peptide" and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers.

The term "class A amphipathic helix" refers to a protein structure that forms an Δ-helix producing a segregation of a polar and nonpolar faces with the positively charged residues residing at the polar-nonpolar interface and the negatively charged residues residing at the center of the polar face (see, e.g., " Segrest et al. (1990) *Proteins: Structure, Function, and Genetics* 8: 103–117).

The term "ameliorating" when used with respect to "ameliorating one or more symptoms of atherosclerosis" refers to a reduction, prevention, or elimination of one or more symptoms characteristic of atherosclerosis and/or associated pathologies. Such a reduction includes, but is not limited to a reduction or elimination of oxidized phospholipids, a reduction in atherosclerotic plaque formation and rupture, a reduction in clinical events such as heart attack, angina, or stroke, a decrease in hypertension, a decrease in inflammatory protein biosynthesis, reduction in plasma cholesterol, and the like.

The term "enantiomeric amino acids" refers to amino acids that can exist in at least two forms that are nonsuperimposable mirror images of each other. Most amino acids (except glycine) are enantiomeric and exist in a so-called L-form (L amino acid) or D-form (D amino acid). Most naturally occurring amino acids are "L" amino acids. The terms "D amino acid" and "L amino acid" are used to refer to absolute configuration of the amino acid, rather than a particular direction of rotation of plane-polarized light. The usage herein is consistent with standard usage by those of skill in the art.

The term "protecting group" refers to a chemical group that, when attached to a functional group in an amino acid (e.g. a side chain, an alpha amino group, an alpha carboxyl group, etc.) blocks or masks the properties of that functional group. Preferred amino-terminal protecting groups include, but are not limited to acetyl, or amino groups. Other amino-terminal protecting groups include, but are not limited to alkyl chains as in fatty acids, propeonyl, formyl and others. Preferred carboxyl terminal protecting groups include, but are not limited to groups that form amides or esters.

The phrase "protect a phospholipid from oxidation by an oxidizing agent" refers to the ability of a compound to reduce the rate of oxidation of a phospholipid (or the amount of oxidized phospholipid produced) when that phospholipid is contacted with an oxidizing agent (e.g. hydrogen peroxide, 13-(S)-HPODE, 15-(S)-HPETE, HPODE, HPETE, HODE, HETE, etc.).

The terms "low density lipoprotein" or "LDL" is defined in accordance with common usage of those of skill in the art. Generally, LDL refers to the lipid-protein complex which when isolated by ultracentrifugation is found in the density range d=1.019 to d=1.063.

The terms "high density lipoprotein" or "HDL" is defined in accordance with common usage of those of skill in the art. Generally "HDL" refers to a lipid-protein complex which when isolated by ultracentrifugation is found in the density range of d=1.063 to d=1.21.

The term "Group I HDL" refers to a high density lipoprotein or components thereof (e.g. apo A-I, paraoxonase, platelet activating factor acetylhydrolase, etc.) that reduce oxidized lipids (e.g. in low density lipoproteins) or that protect oxidized lipids from oxidation by oxidizing agents.

The term "Group II HDL" refers to an HDL that offers reduced activity or no activity in protecting lipids from oxidation or in repairing (e.g. reducing) oxidized lipids.

The term "HDL component" refers to a component (e.g. molecules) that comprises a high density lipoprotein (HDL). Assays for HDL that protect lipids from oxidation or that repair (e.g. reduce oxidized lipids) also include assays for components of HDL (e.g. apo A-I, paraoxonase, platelet activating factor acetylhydrolase, etc.) that display such activity.

The term "human apo A-I peptide" refers to a full-length human apo A-I peptide or to a fragment or domain thereof comprising a class A amphipathic helix.

A "monocytic reaction" as used herein refers to monocyte activity characteristic of the "inflammatory response" associated with atherosclerotic plaque formation. The monocytic reaction is characterized by monocyte adhesion to cells of the vascular wall (e.g. cells of the vascular endothelium), and/or chemotaxis into the subendothelial space, and/or differentiation of monocytes into macrophages.

The term "absence of change" when referring to the amount of oxidized phospholipid refers to the lack of a detectable change, more preferably the lack of a statistically significant change (e.g. at least at the 85%, preferably at least at the 90%, more preferably at least at the 95%, and most preferably at least at the 98% or 99% confidence level). The absence of a detectable change can also refer to assays in which oxidized phospholipid level changes, but not as much as in the absence of the protein(s) described herein or with reference to other positive or negative controls.

The following abbreviations are used herein: PAPC: L-Δ-1-palmitoyl-2-arachidonoyl-sn-glycero-3-phosphocholine; POVPC:1-palmitoyl-2-(5-oxovaleryl)-sn-glycero-3-phosphocholine; PGPC:1-palmitoyl-2-glutaryl-sn-glycero-3-phosphocholine; PEIPC: 1-palmitoyl-2-(5,6-epoxyisoprostane $E_2$)-sn-glycero-3-phsophocholine; ChC 18:2: cholesteryl linoleate; ChC18:2-OOH: cholesteryl linoleate hydroperoxide; DMPC: 1,2-ditetradecanoyl-rac-glycerol-3-phosphocholine; PON: paraoxonase; HPF: Standardized high power field; PAPC: L-Δ-1-palmitoyl-2-arachidonoyl-sn-glycero-3-phosphocholine; POVPC: 1-palmitoyl-2-(5-oxovaleryl)-sn-glycero-3-phosphocholine; PGPC:1-palmitoyl-2-glutaryl-sn-glycero-3-phosphocholine; PEIPC: 1-palmitoyl-2-(5,6-epoxyisoprostane $E_2$)-sn-glycero-3-phosphocholine; PON: paraoxonase; BL/6: C57BL/6J; C3H:C3H/HeJ.

The term "conservative substitution" is used in reference to proteins or peptides to reflect amino acid substitutions that do not substantially alter the activity (specificity (e.g. for lipoproteins))or binding affinity (e.g. for lipids or lipoproteins)) of the molecule. Typically conservative amino acid substitutions involve substitution one amino acid for another amino acid with similar chemical properties (e.g. charge or hydrophobicity). The following six groups each contain amino acids that are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. With respect to the peptides of this invention sequence identity is determined over the full length of the peptide.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman (1988) *Proc. Natl. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle (1987) *J. Mol. Evol.* 35:351–360. The method used is similar to the method described by Higgins & Sharp (1989) *CABIOS* 5: 151–153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al. (1990) *J. Mol. Biol.* 215: 403–410. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=-4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul (1993) *Proc. Natl. Acad. Sci. USA*, 90: 5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

The term "D-18A peptide" refers to a peptide having the sequence: D-W-L-K-A-F-Y-D-K-V-A-E-K-L-K-E-A-F (SEQ ID NO: 1) where all of the enantiomeric amino acids are D form amino acids.

BRIEF DESCRIPTION OF THE DRAWINGS

FIGS. 3A and 3B show the plasma concentration of D vs L peptide after gavage. ApoA-I mimetic peptides D-4F (FIG. 3B) and L-4F (FIG. 3B) were labeled with $^{125}$I and administered by oral gavage to LDL receptor null mice (n=4). Blood was collected after 3 hrs, plasma fractionated by FPLC and radioactivity determined in the eluted fractions. Less than 15% of the L peptide eluted as intact 18 mer whereas more than 70% of the D-4F was intact. These studies demonstrate that the D peptide is dramatically more resistant to degradation in vivo compared with the L peptide.

FIG. 14A: SDS PAGE (18%) of 2F. Lane 1 shows the molecular weight standard and lane 2 shows the band corresponding to 2F (molecular weight is 2242) moving slightly lower than the lowest molecular weight standard (3.5–2.5 kDa). FIG. 14B: Non-denaturing PAGE (4–12%) showing the mobilities of 100 Πg/ml (lane 2) and 250 Πg/ml (lane 1) of 2F indicating self-association in solution. Lane 3 shows the mobility of the high molecular weight standard.

DETAILED DESCRIPTION

I. Mitigation of a Symptom of Atherosclerosis.

This invention pertains to the discovery that synthetic peptides designed to mimic the class A amphipathic helical motif (Segrest et al. (1990) *Proteins: Structure, Function, and Genetics* 8: 103–117) are able to associate with phospholipids and exhibit many biological properties similar to human apo-A-I. In particular, it was a discovery of this invention that when such peptides are formulated using D amino acids, the peptides show dramatically elevated serum half-lives and, particularly when the amino and/or carboxy termini are blocked, can even be orally administered.

Moreover, it was a surprising discovery of this invention that such D-form peptides retain the biological activity of the corresponding L-form peptide. In vivo animal studies using such D-form peptides showed effective oral delivery, elevated serum half-life, and the ability to mitigate or prevent/inhibit one or more symptoms of atherosclerosis.

We discovered that normal HDL inhibits three steps in the formation of mildly oxidized LDL. In those studies (see, copending application U.S. Ser. No. 09/541,468, filed on Mar. 31, 2000) we demonstrated that treating human LDL in vitro with apo A-I or an apo A-I mimetic peptide (37pA) removed seeding molecules from the LDL that included HPODE and HPETE. These seeding molecules were required for cocultures of human artery wall cells to be able to oxidize LDL and for the LDL to induce the artery wall cells to produce monocyte chemotactic activity. We also demonstrated that after injection of apo A-I into mice or infusion into humans, the LDL isolated from the mice or human volunteers after injection/infusion of apo A-I was resistant to oxidation by human artery wall cells and did not induce monocyte chemotactic activity in the artery wall cell cocultures.

Figure 1:
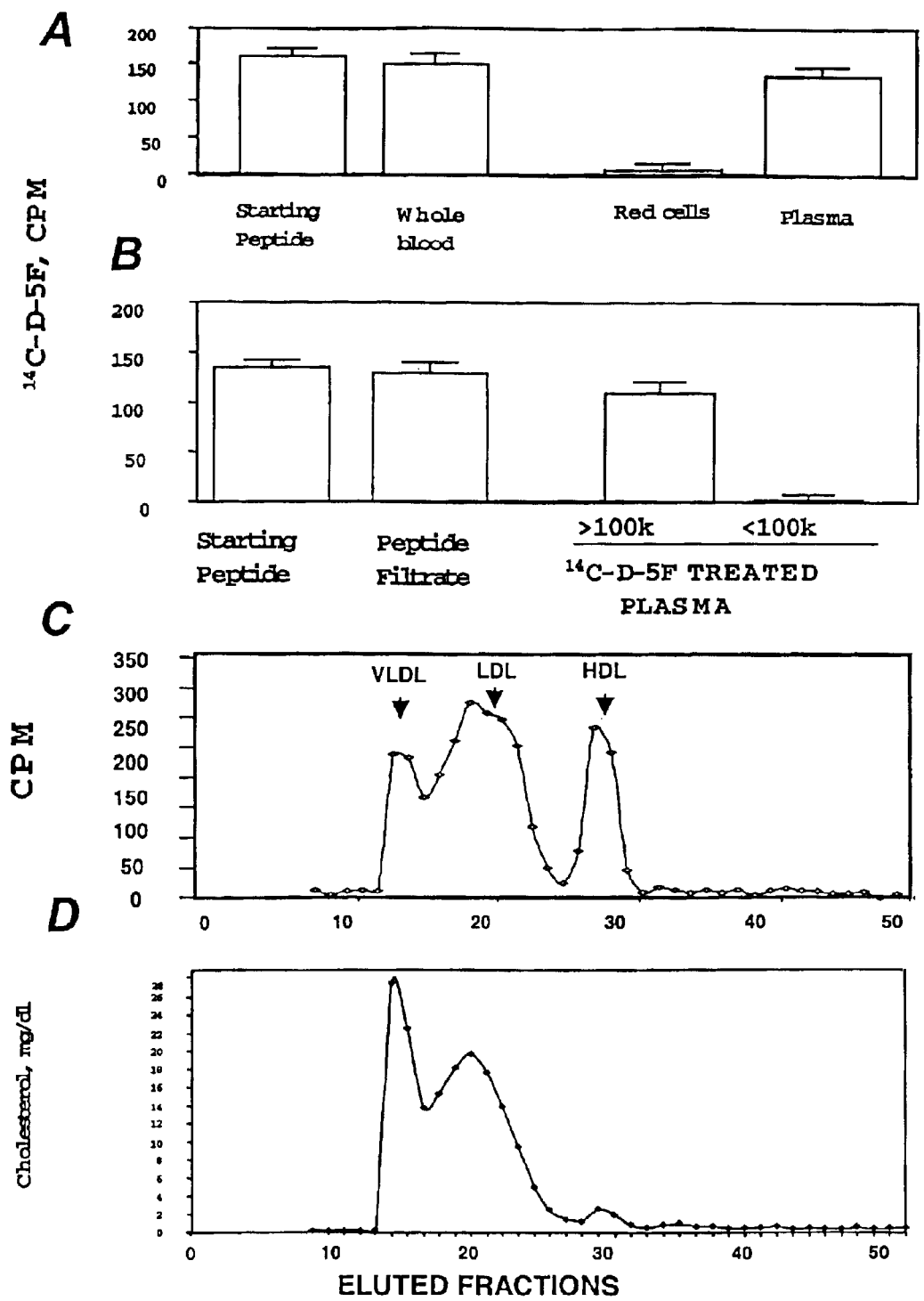
FIG. 1, panels A, B, C, and D show the association of $^{14}$C-D-5F with blood components in an ApoE null mouse. ApoA-I mimetic peptide D-5F labeled with $^{14}$C amino acids was administered by oral gavage to apo E deficient mice (n=5) or incubated with their plasma in vitro. Fasting blood was collected 6 hrs after gavage and $^{14}$C association with blood, plasma, and lipoproteins determined.
Figure 2A:
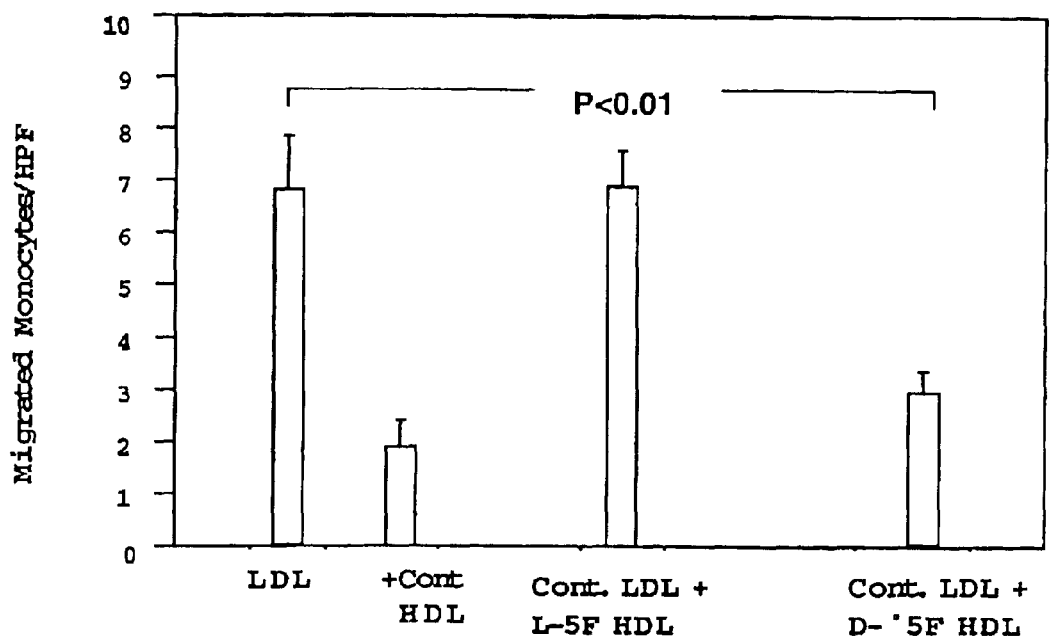
FIGS. 2A and 2B illustrate that orally administered d peptide is active. ApoA-I mimetic peptides D-5F and L-5F (100 µg per animal) were administered to LDL receptor null mice (n=5) by oral gavage. Blood was collected after 6 hrs, LDL and HDL were isolated by gel filtration (FPLC) and examined in the artery wall model system for HDL protective capacity (FIG. 2A) and LDL resistance (FIG. 2B) to oxidation by determining monocyte chemotactic activity generated. As seen, D-5F but not L-5F rendered the HDL markedly more protective and LDL after D-5F became highly resistant to oxidation.
Figure 2B:
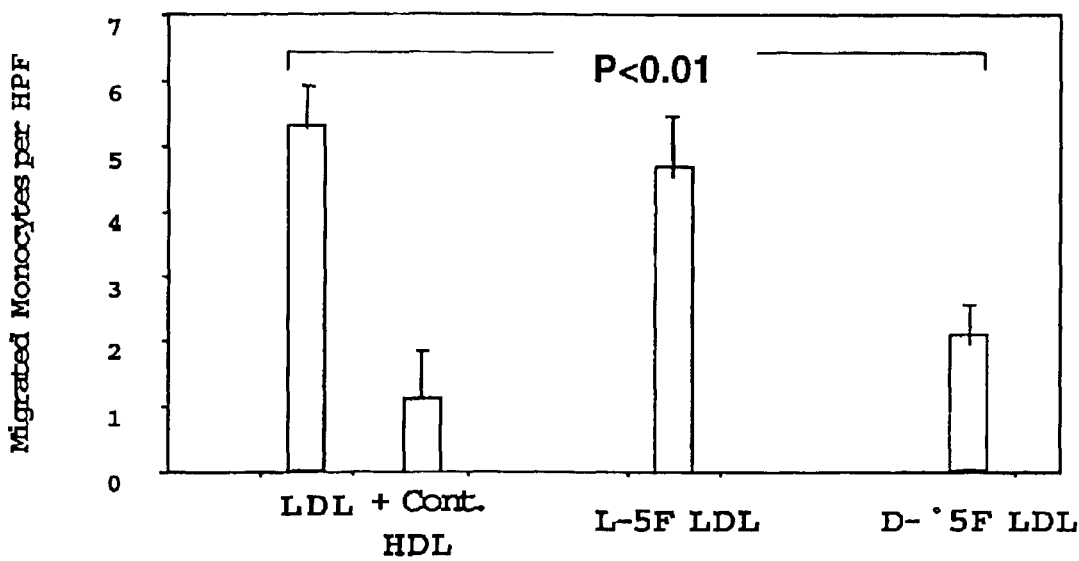
Figure 4:
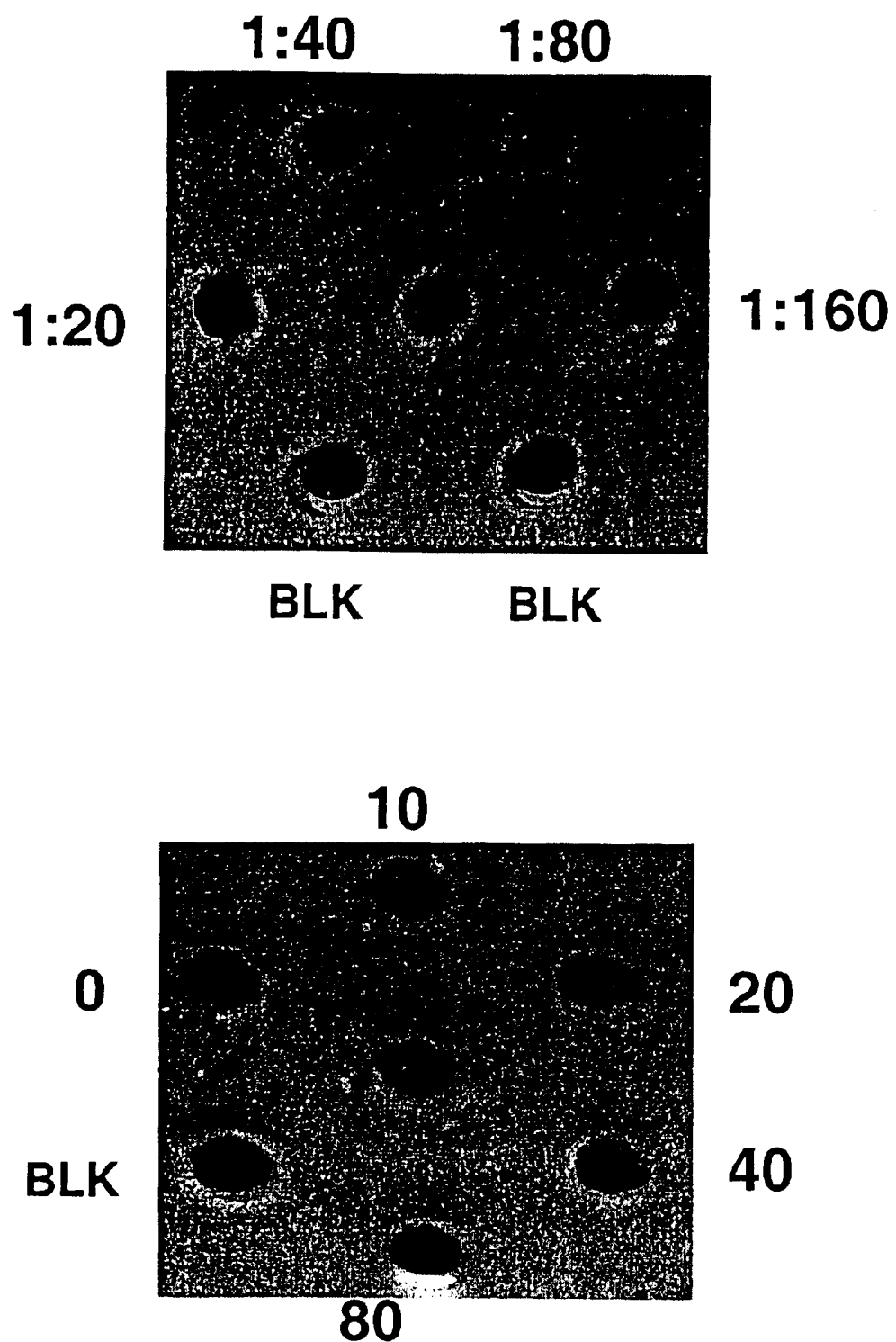
FIG. 4 illustrates the absence of antibody to D-4F in treated mice. No antibody (white precipitation line) to D-4F was detected in LDL receptor null mouse plasma following 6 weeks of treatment with peptide at 5 mg per day (lower panel). The positive control (upper panel) shows the presence of a precipitation line for apoA-I in mouse plasma. Upper panel: Center: rabbit anti ApoA-I and periphery: plasma from D-4F mice. Lower panel: Center: Plasma from LDL R−/− mice treated with D 4F, and Periphery: Pure D-4F peptide at 0 to 80 µg.

The protective function of the D peptides of this invention is illustrated in FIGS. 1 through 5. FIG. 1, panels A, B, C, and D show the association of 14C-D-5F with blood components in an ApoE null mouse. It is also demonstrated herein, that HDL from mice that were fed an atherogenic diet and injected with PBS failed to inhibit the oxidation of human LDL and failed to inhibit LDL-induced monocyte chemotactic activity in human artery wall cocultures. In contrast, HDL from mice fed an atherogenic diet and injected daily with peptides described herein was as effective in inhibiting human LDL oxidation and preventing LDL-induced monocyte chemotactic activity in the cocultures as was normal human HDL (FIGS. 2A and 2B). In addition, LDL taken from mice fed the atherogenic diet and injected daily with PBS was more readily oxidized and more readily induced monocyte chemotactic activity than LDL taken from mice fed the same diet but injected with 20 Πg daily of peptide 5F. The D peptide did not appear to be immunogenic (FIG. 4).

Figure 5:
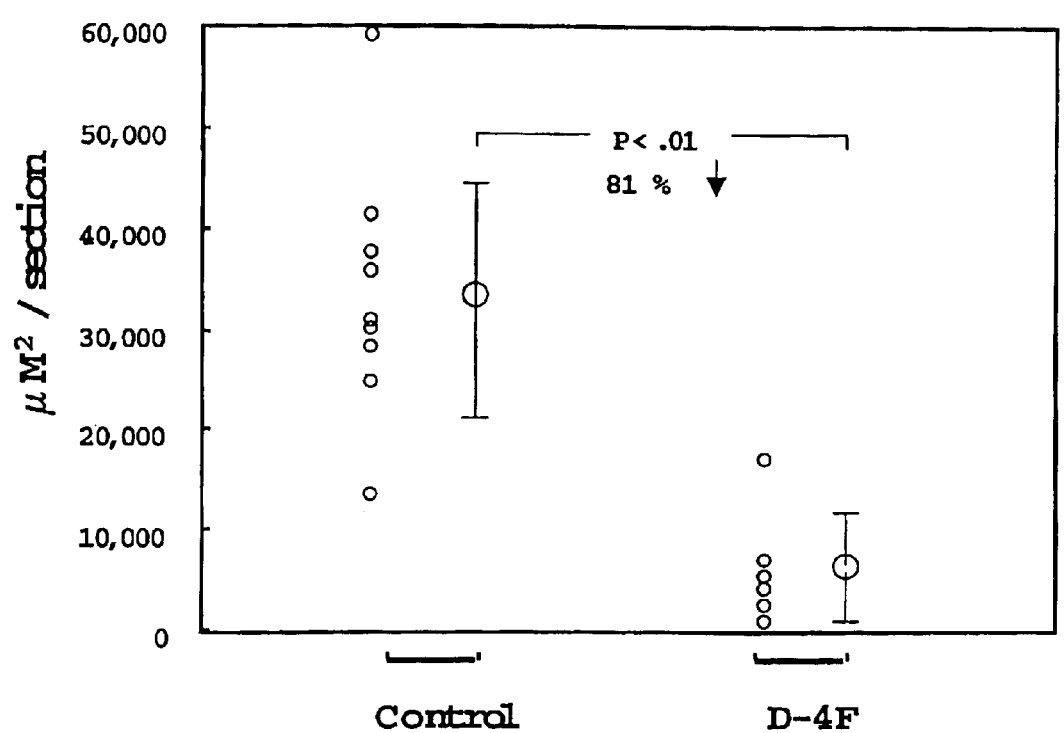
FIG. 5 shows the incidence of fatty streak lesions in the aortic root of LDL receptor null mice on a Western Diet. Groups of LDL receptor null mice were placed on a Western type diet and were given orally, vehicle (Control) (n=9) or peptide D-4F (n=6), twice daily for 6 weeks. The mice were subsequently sacrificed, aortic arch fixed and sectioned and fatty streak lesions quantified. The mice receiving D-4F had an 81% reduction in lesion area (p<0.01).

The in vitro responses of human artery wall cells to HDL and LDL from mice fed the atherogenic diet and injected with a peptide according to this invention are consistent with the protective action of shown by such peptides in vivo. Despite, similar levels of total cholesterol, LDL-cholesterol, IDL+VLDL-cholesterol, and lower HDL-cholesterol as a percent of total cholesterol, the animals fed the atherogenic diet and injected with the peptide had significantly lower lesion scores (FIG. 5). The peptides of this invention thus prevented progression of atherosclerotic lesions in mice fed an atherogenic diet.

Thus, in one embodiment, this invention provides methods for ameliorating and/or preventing one or more symptoms of atherosclerosis. The methods preferably involve administering to an organism, preferably a mammal, more preferably a human one or more of the peptides of this invention (or mimetics of such peptides). The peptide(s) can be administered, as described herein, according to any of a number of standard methods including, but not limited to injection, suppository, nasal spray, time-release implant, transdermal patch, and the like. In one particularly preferred embodiment, the peptide(s) are administered orally (e.g. as a syrup, capsule, or tablet).

The methods involve the administration of a single polypeptide of this invention or the administration of two or more different polypeptides. The polypeptides can be provided as monomers or in dimeric, oligomeric or polymeric forms. In certain embodiments, the multimeric forms may comprise associated monomers (e.g. ionically or hydrophobically linked) while certain other multimeric forms comprise covalently linked monomers (directly linked or through a linker).

While the invention is described with respect to use in humans, it is also suitable for animal, e.g. veterinary use. Thus preferred organisms include, but are not limited to humans, non-human primates, canines, equines, felines, porcines, ungulates, largomorphs, and the like.

The methods of this invention are not limited to humans or non-human animals showing one or more symptom(s) of atherosclerosis (e.g. hypertension, , plaque formation and rupture, reduction in clinical events such as heart attack, angina, or stroke, high levels of plasma cholesterol, high levels of low density lipoprotein, high levels of very low density lipoprotein, or inflammatory proteins, etc.), but are useful in a prophylactic context. Thus, the peptides of this invention (or mimetics thereof) may be administered to organisms to prevent the onset/development of one or more symptoms of atherosclerosis. Particularly preferred subjects in this context are subjects showing one or more risk factors for atherosclerosis (e.g. family history, hypertension, obesity, high alcohol consumption, smoking, high blood cholesterol, high blood triglycerides, elevated blood LDL, VLDL, IDL, or low HDL, diabetes, or a family history of diabetes, high blood lipids, heart attack, angina or stroke, etc.).

In addition to methods of use of the atherosclerosis-inhibiting peptides of this invention, this invention also provides the peptides themselves, the peptides formulated as pharmaceuticals, particularly for oral delivery, and kits for the treatment and/or prevention of one or more symptoms of atherosclerosis.

II. Mitigation of a Symptom of Atheroscloerosis Associated with an Acute Inflammatory Response.

The atherosclerosis-inhibiting peptides of this invention are also useful in a number of other contexts. In particular, we have observed that cardiovascular complications (e.g. atherosclerosis, stroke, etc.) frequently accompany or follow the onset of an acute phase inflammatory response. Such an acute state inflammatory response is often associated with a recurrent inflammatory disease (e.g., leprosy, tuberculosis, systemic lupus erythematosus, and rheumatoid arthritis), a viral infection (e.g. influenza), a bacterial infection, a fungal infection, an organ transplant, a wound or other trauma, an implanted prosthesis, a biofilm, and the like.

It was a surprising discovery of this invention that administration of one or more of the peptide described herein, can reduce or prevent the formation of oxidized phospholipids during or following an acute phase response and thereby mitigate or eliminate cardiovascular complications associated with such a condition.

Thus, for example, we have demonstrated that a consequence of influenza infection is the dimunition in paraoxonase and platelet activating acetylhydrolase activity in the HDL. Without being bound by a particular theory, we believe that, as a result of the loss of these HDL enzymatic activities and also as a result of the association of pro-oxidant proteins with HDL during the acute phase response, HDL is no longer able to prevent LDL oxidation and was no longer able to prevent the LDL-induced production of monocyte chemotactic activity by endothelial cells.

We observed that in a subject injected with very low dosages of the polypeptides of this invention (e.g. 20 micrograms for mice) daily after infection with the influenza A virus paraoxonase levels did not fall and the biologically active oxidized phospholipids were not generated beyond background. This indicates that D-4F (and/or other peptides of this invention) can be administered (e.g. orally or by injection) to patients with known coronary artery disease during influenza infection or other events that can generate an acute phase inflammatory response (e.g. due to viral infection, bacterial infection, trauma, transplant, various autoimmune conditions, etc.) and thus we can prevent by this short term treatment the increased incidence of heart attack and stroke associated with pathologies that generate such inflammatory states.

Thus, in certain embodiments, this invention contemplates administering one or more of the peptides of this invention to a subject at risk for, or incurring, an acute inflammatory response and/or at risk for or incurring a symptom of atherosclerosis.

Thus, for example, a person having or at risk for coronary disease may prophylactically be administered a polypeptide of this invention during flu season. A person (or animal) subject to a recurrent inflammatory condition, e.g. rheumatoid arthritis, various autoimmune diseases, etc., can be treated with a polypeptide of this invention to mitigate or prevent the development of atherosclerosis or stroke. A person (or animal) subject to trauma, e.g. acute injury, tissue transplant, etc. can be treated with a polypeptide of this invention to mitigate the development of atherosclerosis or stroke.

In certain instances such methods will entail a diagnosis of the occurrence or risk of an acute inflammatory response. The acute inflammatory response typically involves alterations in metabolism and gene regulation in the liver. It is a dynamic homeostatic process that involves all of the major systems of the body, in addition to the immune, cardiovascular and central nervous system. Normally, the acute phase response lasts only a few days; however, in cases of chronic or recurring inflammation, an aberrant continuation of some aspects of the acute phase response may contribute to the underlying tissue damage that accompanies the disease, and may also lead to further complications, for example cardiovascular diseases or protein deposition diseases such as amyloidosis.

An important aspect of the acute phase response is the radically altered biosynthetic profile of the liver. Under normal circumstances, the liver synthesizes a characteristic range of plasma proteins at steady state concentrations. Many of these proteins have important functions and higher plasma levels of these acute phase reactants (APRs) or acute phase proteins (APPs) are required during the acute phase response following an inflammatory stimulus. Although most APRs are synthesized by hepatocytes, some are produced by other cell types, including monocytes, endothelial cells, fibroblasts and adipocytes. Most APRs are induced between 50% and several-fold over normal levels. In contrast, the major APRs can increase to 1000-fold over normal levels. This group includes serum amyloid A (SAA) and either C-reactive protein (CRP) in humans or its homologue in mice, serum amyloid P component (SAP). So-called negative APRs are decreased in plasma concentration during the acute phase response to allow an increase in the capacity of the liver to synthesize the induced APRs.

In certain embodiments, the acute phase response, or risk therefore is evaluated by measuring one or more APPs. Measuring such markers is well known to those of skill in the art, and commercial companies exist that provide such measurement (e.g. AGP measured by Cardiotech Services, Louisville, Ky.).

III. Mitigation of a Symptom or Condition Associated with Coronary Calcification and Osteoporosis.

We have also identified oxidized lipids as a cause of coronary calcification and osteoporosis. Moreover, without being bound to a particularly theory, we believe the same mechanisms are involved in the pathogenesis of calcific aortic stenosis.

Thus, in certain embodiments, this invention contemplates the use of the peptides described herein to inhibit or prevent a symptom of a disease such as polymyalgia rheumatica, polyarteritis nodosa, scleroderma, idiopathic pulmonary fibrosis, chronic obstructive pulmonary disease, Alzheimers Disease, AIDS, coronary calcification, calcific aortic stenosis, osteoporosis, and the like.

III. Preferred Peptides and Their Preparation.

Preferred Peptides.

It was a discovery of this invention that class A peptides, are capable of mitigating one or more symptoms of atherosclerosis. Class A peptides are characterized by formation of an α-helix that produces a segregation of polar and nonpolar residues thereby forming a polar and a nonpolar face with the positively charged residues residing at the polar-nonpolar interface and the negatively charged residues residing at the center of the polar face (see, e.g., Anantharamaiah (1986) *Meth. Enzymol,* 128: 626–668). It is noted that the fourth exon of apo A-I, when folded into 3.667 residues/turn produces a class A amphipathic helical structure.

One particularly preferred class A peptide, designated 18A (see, Table 1, and also Anantharamaiah (1986) *Meth. Enzymol,* 128: 626–668) was modified as described herein to produce peptides orally administratable and highly effective at inhibiting or preventing one or more symptoms of atherosclerosis. Without being bound by a particular theory, it is believed that the peptides of this invention act in vivo may by picking up seeding molecule(s) that mitigate oxidation of LDL.

We determined that increasing the number of Phe residues on the hydrophobic face of 18A would theoretically increase lipid affinity as determined by the computation described by Palgunachari et al. (1996) *Arteriosclerosis, Thrombosis, & Vascular Biology* 16: 328–338. Theoretically, a systematic substitution of residues in the nonpolar face of 18A with Phe could yield six peptides. Peptides with an additional 2, 3 and 4 Phe would have theoretical lipid affinity (O) values of 13, 14 and 15 units, respectively. However, the 1 values jumped four units if the additional Phe were increased from 4 to 5 (to 19 O units). Increasing to 6 or 7 Phe would produce a less dramatic increase (to 20 and 21 O units, respectively). Therefore, we chose 5 additional Phe (and hence the peptides designation as 5F). In one particularly preferred embodiment, the 5F peptide was blocked in that the amino terminal residue was acetylated and the carboxyl terminal residue was amidated.

The new class A peptide analog, 5F inhibited, lesion development in atherosclerosis-susceptible mice. The new peptide analog, 5F, was compared with mouse apo A-I (MoA-I) for efficacy in inhibiting diet-induced atherosclerosis in these mice using peptide dosages based on the study by Levine et al. (Levine et al. (1993) *Proc. Natl. Acad. Sci. USA* 90:12040–12044).

A number of other class A peptides were also produced and showed varying, but significant degrees of efficacy in mitigating one or more symptoms of atherosclerosis. A number of such peptides are illustrated in Table 1.

TABLE 1

Preferred peptides for use in this invention.

| Peptide Name | Amino Acid Sequence | SEQ ID NO. |
|---|---|---|
| 18A | D-W-L-K-A-F-Y-D-K-V-A-E-K-L-K-E-A-F | 1 |
| 2F | Ac-D-W-L-K-A-F-Y-D-K-V-A-E-K-L-K-E-A-F-NH$_2$ | 2 |
| 3F | Ac-D-W-F-K-A-F-Y-D-K-V-A-E-K-L-K-E-A-F-NH$_2$ | 3 |
| 3F14 | Ac-D-W-L-K-A-F-Y-D-K-V-A-E-K-F-K-E-A-F-NH$_2$ | 4 |
| 5F | Ac-D-W-F-K-A-F-Y-D-K-V-A-E-K-F-K-E-A-F-NH$_2$ | 5 |
| 6F | Ac-D-W-L-K-A-F-Y-D-K-F-F-E-K-F-K-E-F-F-NH$_2$ | 6 |
| 7F | Ac-D-W-F-K-A-F-Y-D-K-F-F-E-K-F-K-E-F-F-NH$_2$ | 7 |
|  | Ac-D-W-L-K-A-F-Y-D-K-V-A-E-K-F-K-E-A-F-NH$_2$ | 8 |
| 3F-14 | Ac-D-W-L-K-A-F-Y-D-K-V-A-E-K-L-K-E-F-NH$_2$ | 9 |
|  | Ac-D-W-L-K-A-F-Y-D-K-V-F-E-K-F-K-E-A-F-NH$_2$ | 10 |
|  | Ac-D-W-L-K-A-F-Y-D-K-V-F-E-K-L-K-E-F-F-NH$_2$ | 11 |
|  | Ac-D-W-L-K-A-F-Y-D-K-V-A-E-K-F-K-E-F-F-NH$_2$ | 12 |
| 5Fnew | Ac-D-W-L-K-A-F-Y-D-K-V-F-E-K-F-K-E-F-F-NH$_2$ | 13 |
|  | Ac-E-W-L-K-L-F-Y-E-K-V-L-E-K-F-K-E-A-F-NH$_2$ | 14 |
|  | Ac-E-W-L-K-A-F-Y-D-K-V-A-E-K-F-K-E-A-F-NH$_2$ | 15 |
|  | Ac-E-W-L-K-A-F-Y-D-K-V-A-E-K-L-K-E-F-F-NH$_2$ | 16 |
|  | Ac-E-W-L-K-A-F-Y-D-K-V-F-E-K-F-K-E-A-F-NH$_2$ | 17 |
|  | Ac-E-W-L-K-A-F-Y-D-K-V-F-E-K-L-K-E-F-F-NH$_2$ | 18 |
|  | Ac-E-W-L-K-A-F-Y-D-K-V-A-E-K-F-K-E-F-F-NH$_2$ | 19 |
|  | Ac-E-W-L-K-A-F-Y-D-K-V-F-E-K-F-K-E-F-F-NH$_2$ | 20 |
|  | Ac-A-F-Y-D-K-V-A-E-K-L-K-E-A-F-NH$_2$ | 21 |
|  | Ac-A-F-Y-D-K-V-A-E-K-F-K-E-A-F-NH$_2$ | 22 |
|  | Ac-A-F-Y-D-K-V-A-E-K-F-K-E-A-F-NH$_2$ | 23 |
|  | Ac-A-F-Y-D-K-F-F-E-K-F-K-E-F-F-NH$_2$ | 24 |
|  | Ac-A-F-Y-D-K-F-F-E-K-F-K-E-F-F-NH$_2$ | 25 |
|  | Ac-A-F-Y-D-K-V-A-E-K-F-K-E-A-F-NH$_2$ | 26 |
|  | Ac-A-F-Y-D-K-V-A-E-K-L-K-E-F-F-NH$_2$ | 27 |
|  | Ac-A-F-Y-D-K-V-F-E-K-F-K-E-A-F-NH$_2$ | 28 |
|  | Ac-A-F-Y-D-K-V-F-E-K-L-K-E-F-F-NH$_2$ | 29 |
|  | Ac-A-F-Y-D-K-V-A-E-K-F-K-E-F-F-NH$_2$ | 30 |
|  | Ac-K-A-F-Y-D-K-V-F-E-K-F-K-E-F-NH$_2$ | 31 |
|  | Ac-L-F-Y-E-K-V-L-E-K-F-K-E-A-F-NH$_2$ | 32 |
|  | Ac-A-F-Y-D-K-V-A-E-K-F-K-E-A-F-NH$_2$ | 33 |
|  | Ac-A-F-Y-D-K-V-A-E-K-L-K-E-F-F-NH$_2$ | 34 |
|  | Ac-A-F-Y-D-K-V-F-E-K-F-K-E-A-F-NH$_2$ | 35 |
|  | Ac-A-F-Y-D-K-V-F-E-K-L-K-E-F-F-NH$_2$ | 36 |
|  | Ac-A-F-Y-D-K-V-A-E-K-F-K-E-F-F-NH$_2$ | 37 |

TABLE 1-continued

Preferred peptides for use in this invention.

| Peptide Name | Amino Acid Sequence | SEQ ID NO. |
|---|---|---|
| | Ac-A-F-Y-D-K-V-F-E-K-F-K-E-F-F-NH$_2$ | 38 |
| | Ac-D-W-L-K-A-L-Y-D-K-V-A-E-K-L-K-E-A-L-NH$_2$ | 39 |
| 4F | Ac-D-W-F-K-A-F-Y-E-K-V-A-E-K-L-K-E-F-F-NH$_2$ | 40 |
| 7F | Ac-D-W-F-K-A-F-Y-E-K-F-F-E-K-F-K-E-F-F-NH$_2$ | 41 |
| | Ac-E-W-L-K-A-L-Y-E-K-V-A-E-K-L-K-E-A-L-NH$_2$ | 42 |
| 2F analog | Ac-E-W-L-K-A-F-Y-E-K-V-A-E-K-L-K-E-A-F-NH$_2$ | 43 |
| 4F analog | Ac-E-W-F-K-A-F-Y-E-K-V-A-E-K-L-K-E-F-F-NH$_2$ | 44 |
| 5F analog | Ac-E-W-L-K-A-F-Y-E-K-V-F-E-K-F-K-E-F-F-NH$_2$ | 45 |
| 6F analog | Ac-E-W-L-K-A-F-Y-E-K-F-F-E-K-F-K-E-F-F-NH$_2$ | 46 |
| 7F analog | Ac-E-W-F-K-A-F-Y-E-K-F-F-E-K-F-K-E-F-F-NH$_2$ | 47 |
| | Ac-D-F-L-K-A-W-Y-D-K-V-A-E-K-L-K-E-A-W-NH$_2$ | 48 |
| | Ac-E-F-L-K-A-W-Y-E-K-V-A-E-K-L-K-E-A-W-NH$_2$ | 49 |
| | Ac-D-F-W-K-A-W-Y-D-K-V-A-E-K-L-K-E-W-W-NH$_2$ | 50 |
| | Ac-E-F-W-K-A-W-Y-E-K-V-A-E-K-L-K-E-W-W-NH$_2$ | 51 |
| | Ac-D-K-L-K-A-F-Y-D-K-V-F-E-W-A-K-E-A-F-NH$_2$ | 52 |
| | Ac-D-K-W-K-A-V-Y-D-K-F-A-E-A-F-K-E-F-L-NH$_2$ | 53 |
| | Ac-E-K-L-K-A-F-Y-E-K-V-F-E-W-A-K-E-A-F-NH$_2$ | 54 |
| | Ac-E-K-W-K-A-V-Y-E-K-F-A-E-A-F-K-E-F-L-NH$_2$ | 55 |
| | Ac-D-W-L-K-A-F-V-D-K-F-A-E-K-F-K-E-A-Y-NH$_2$ | 56 |
| | Ac-E-K-W-K-A-V-Y-E-K-F-A-E-A-F-K-E-F-L-NH$_2$ | 57 |
| | Ac-D-W-L-K-A-F-V-Y-D-K-V-F-K-L-K-E-F-F-NH$_2$ | 58 |
| | Ac-E-W-L-K-A-F-V-Y-E-K-V-F-K-L-K-E-F-F-NH$_2$ | 59 |
| | Ac-D-W-L-R-A-F-Y-D-K-V-A-E-K-L-K-E-A-F-NH$_2$ | 60 |
| | Ac-E-W-L-R-A-F-Y-E-K-V-A-E-K-L-K-E-A-F-NH$_2$ | 61 |
| | Ac-D-W-L-K-A-F-Y-D-R-V-A-E-K-L-K-E-A-F-NH$_2$ | 62 |
| | Ac-E-W-L-K-A-F-Y-E-R-V-A-E-K-L-K-E-A-F-NH$_2$ | 63 |
| | Ac-D-W-L-K-A-F-Y-D-K-V-A-E-R-L-K-E-A-F-NH$_2$ | 64 |
| | Ac-E-W-L-K-A-F-Y-E-K-V-A-E-R-L-K-E-A-F-NH$_2$ | 65 |
| | Ac-D-W-L-K-A-F-Y-D-K-V-A-E-K-L-R-E-A-F-NH$_2$ | 66 |
| | Ac-E-W-L-K-A-F-Y-E-K-V-A-E-K-L-R-E-A-F-NH$_2$ | 67 |
| | Ac-D-W-L-K-A-F-Y-D-R-V-A-E-R-L-K-E-A-F-NH$_2$ | 68 |
| | Ac-E-W-L-K-A-F-Y-E-R-V-A-E-R-L-K-E-A-F-NH$_2$ | 69 |
| | Ac-D-W-L-R-A-F-Y-D-K-V-A-E-K-L-R-E-A-F-NH$_2$ | 70 |
| | Ac-E-W-L-R-A-F-Y-E-K-V-A-E-K-L-R-E-A-F-NH$_2$ | 71 |
| | Ac-D-W-L-R-A-F-Y-D-R-V-A-E-K-L-K-E-A-F-NH$_2$ | 72 |
| | Ac-E-W-L-R-A-F-Y-E-R-V-A-E-K-L-K-E-A-F-NH$_2$ | 73 |
| | Ac-D-W-L-K-A-F-Y-D-K-V-A-E-R-L-R-E-A-F-NH$_2$ | 74 |
| | Ac-E-W-L-K-A-F-Y-E-K-V-A-E-R-L-R-E-A-F-NH$_2$ | 75 |
| | Ac-D-W-L-R-A-F-Y-D-K-V-A-E-R-L-K-E-A-F-NH$_2$ | 76 |
| | Ac-E-W-L-R-A-F-Y-E-K-V-A-E-R-L-K-E-A-F-NH$_2$ | 77 |
| 18A-Pro-18A | D-W-L-K-A-F-Y-D-K-V-A-E-K-L-K-E-A-F-<u>P</u>-D-W-L-K-A-F-Y-D-K-V-A-E-K-L-K-E-A-F | 78 |
| 3F analogs | D-W-L-K-A-F-Y-D-K-V-A-E-K-L-K-E-F-F-<u>P</u>-D-W-L-K-A-F-Y-D-K-V-A-E-K-L-K-E-F-F | 79 |
| | D-W-F-K-A-F-Y-D-K-V-A-E-K-L-K-E-A-F-<u>P</u>-D-W-F-K-A-F-Y-D-K-V-A-E-K-L-K-E-A-F | 80 |
| | D-K-L-K-A-F-Y-D-K-V-F-E-W-A-K-E-A-F-<u>P</u>-D-K-L-K-A-F-Y-D-K-V-F-E-W-L-K-E-A-F | 81 |
| | D-K-W-K-A-V-Y-D-K-F-A-E-A-F-K-E-F-L-<u>P</u>-D-K-W-K-A-V-Y-D-K-F-A-E-A-F-K-E-F-L | 82 |
| 4F analog of 37pA | D-W-F-K-A-F-Y-D-K-V-A-E-K-F-K-E-A-F-<u>P</u>-D-W-F-K-A-F-Y-D-K-V-A-E-K-F-K-E-A-F | 83 |
| | D-W-L-K-A-F-V-Y-D-K-V-F-K-L-K-E-F-F-<u>P</u>-D-W-L-K-A-F-V-Y-D-K-V-F-K-L-K-E-F-F | 84 |
| 5F analogs of 37pA | D-W-L-K-A-F-Y-D-K-F-A-E-K-F-K-E-F-F-<u>P</u>-D-W-L-K-A-F-Y-D-K-F-A-E-K-F-K-E-F-F | 85 |

[1]Linkers are underlined.

While various peptides of Table 1, are illustrated with an acetyl group protecting the amino terminus and an amide group protecting the carboxyl terminus, either or both of these protecting groups may be eliminated and/or substituted with another protecting group as described herein. In particularly preferred embodiments, the peptides comprise one or more D-form amino acids as described herein. In certain embodiments, every amino acid (e.g. every enantiomeric amino acid) of the peptides of Table 1 is a D-form amino acid.

It is also noted that Table 1 is not fully inclusive. Using the teaching provided herein, other suitable peptides can routinely be produced (e.g. by conservative or semi-conservative substitutions (e.g. D replaced by E), extensions, deletions, and the like). Thus, for example, one embodiment utilizes truncations of any one or more of peptides identified by SEQ ID Nos:2–20 and 39–85. Thus, for example, SEQ ID NO: 21 illustrates a peptide comprising 14 amino acids from the C-terminus of 18A including one or more D amino acids, while SEQ ID NOS:22–38 illustrate other truncations. Longer peptides are also suitable. Such longer peptides may entirely form a class A amphipathic helix, or the class A amphipathic helix (helices) may form one or more domains of the peptide. In addition, this invention contemplates multimeric versions of the peptides. Thus, for example, the peptides illustrated in Table 1 can be coupled together (directly or through a linker (e.g. a carbon linker, or one or more amino acids) with one or more intervening amino acids). Illustrative polymeric peptides include 18A-Pro-18A and the peptides of SEQ ID NOs:79–85 preferably comprising one or more D amino acids, more preferably with every amino acid a D amino acid as described herein and/or having one or both termini protected.

It was a surprising discovery of this invention that, when the class A peptides (e.g. as illustrated in Table 1) incorporated D amino acids they retained their activity and, but could be administered orally. Moreover this oral administration resulted in relatively efficient uptake and significant serum half-life thereby providing an efficacious method of mitigating one or more symptoms of atherosclerosis.

Using the teaching provided herein, one of skill can routinely modify the illustrated class A peptides to produce other suitable class A peptides of this invention. For example, routine conservative or semi-conservative substitutions (e.g. E for D) can be made of the existing amino acids. The effect of various substitutions on lipid affinity of the resulting peptide can be predicted using the computational method described by Palgunachari et al. (1996) *Arteriosclerosis, Thrombosis, & Vascular Biology* 16: 328–338. The peptides can be lengthened or shortened as long as the class A Δ-helix structure is preserved. In addition, substitutions can be made to render the resulting peptide more similar to peptide(s) endogenously produced by the subject species.

In certain embodiments, the peptides of this invention comprise "D" forms of the peptides described in U.S. Pat. No. 4,643,988, more preferably "D" forms having one or both termini coupled to protecting groups. Such peptides include peptides having the formula $A_1$-$B_1$-$B_2$-$C_1$-D-$B_3$-$B_4$-$A_2$-$C_2$-$B_5$-$B_6$-$A_3$-$C_3$-$B_7$-$C_4$-$A_4$-$B_8$-$B_9$ (SEQ ID NO:86) wherein $A_1$, $A_2$, $A_3$ and $A_4$ are independently aspartic acid or glutamic acid, or homologues or analogues thereof; $B_1$, $B_2$, $B_3$, $B_4$, $B_5$, $B_6$, $B_7$, $B_8$ and $B_9$ are independently tryptophan, phenylalanine, alanine, leucine, tyrosine, isoleucine, valine or Δ-naphthylalanine, or homologues or analogues thereof; $C_1$, $C_2$, $C_3$ and $C_4$ are independently lysine or arginine, and D is serine, threonine, alanine, glycine, histidine, or homologues or analogues thereof; provided that, when $A_1$ and $A_2$ are aspartic acid, $A_3$ and $A_4$ are glutamic acid, $B_2$ and $B_9$ are leucine, $B_3$ and $B_7$ are phenylalanine, $B_4$ is tyrosine, $B_5$ is valine, $B_6$, $B_8$, and D are alanine, and $C_1$, $C_2$, $C_3$ and $C_4$ are lysine, $B_1$ is not Tryptophan, where at one enantiomeric amino acid is a "D" form amino acids. Preferably at least 50% of the enantiomeric amino acids are "D" form, more preferably at least 80% of the enantiomeric amino acids are "D" form, and most preferably at least 90% or even all of the enantiomeric amino acids are "D" form amino acids.

While, in preferred embodiments, the peptides of this invention utilize naturally-occurring amino acids or D forms of naturally occurring amino acids, substitutions with non-naturally occurring amino acids (e.g., methionine sulfoxide, methionine methylsulfonium, norleucine, episilon-aminocaproic acid, 4-aminobutanoic acid, tetrahydroisoquinoline-3-carboxylic acid, 8-aminocaprylic acid, 4-aminobutyric acid, Lys(N(epsilon)-trifluoroacetyl), α-aminoisobutyric acid, and the like) are also contemplated.

In addition to the class A peptides described herein, peptidomimetics are also contemplated herein. Peptide analogs are commonly used in the pharmaceutical industry as non-peptide drugs with properties analogous to those of the template peptide. These types of non-peptide compound are termed "peptide mimetics" or "peptidomimetics" (Fauchere (1986) *Adv. Drug Res.* 15: 29; Veber and Freidinger (1985) *TINS p.*392; and Evans et al. (1987) *J. Med. Chem.* 30: 1229) and are usually developed with the aid of computerized molecular modeling. Peptide mimetics that are structurally similar to therapeutically useful peptides may be used to produce an equivalent therapeutic or prophylactic effect.

Generally, peptidomimetics are structurally similar to a paradigm polypeptide (i.e., 5F described herein), but have one or more peptide linkages optionally replaced by a linkage selected from the group consisting of: —$CH_2NH$—, —$CH_2S$—, —$CH_2$—$CH_2$—, —$CH$=$CH$— (cis and trans), —$COCH_2$—, —$CH(OH)CH_2$—, —$CH_2SO$—, etc. by methods known in the art and further described in the following references: Spatola (1983) p. 267 in *Chemistry and Biochemistry of Amino Acids, Peptides, and Proteins*, B. Weinstein, eds., Marcel Dekker, New York,; Spatola (1983) *Vega Data* 1(3) *Peptide Backbone Modifications*. (general review); Morley (1980) *Trends Pharm Sci* pp. 463–468 (general review); Hudson et al. (1979) *Int J Pept Prot Res* 14:177–185 (—$CH_2NH$—, $CH_2CH_2$—); Spatola et al. (1986) *Life Sci* 38:1243–1249 (—$CH_2$—S); Hann, (1982) *J Chem Soc Perkin Trans I* 307–314 (—CH—CH—, cis and trans); Almquist et al. (1980) *J Med Chem.* 23:1392–1398 (—$COCH_2$—); Jennings-White et al.(1982) *Tetrahedron Lett.* 23:2533 (—$COCH_2$—); Szelke, M. et al., European Appln. EP 45665 (1982) CA: 97:39405 (1982) (—CH(OH) CH2-); Holladay et al. (1983) *Tetrahedron Lett* 24:4401–4404 (—$C(OH)CH_2$—); and Hruby (1982) *Life Sci.,* 31:189–199 (—$CH_2$—S—)).

A particularly preferred non-peptide linkage is —$CH_2NH$—. Such peptide mimetics may have significant advantages over polypeptide embodiments, including, for example: more economical production, greater chemical stability, enhanced pharmacological properties (half-life, absorption, potency, efficacy, etc.), reduced antigenicity, and others.

In addition, circularly permutations of the peptides described herein or constrained peptides (including cyclized peptides) comprising a consensus sequence or a substantially identical consensus sequence variation may be generated by methods known in the art (Rizo and Gierasch (1992) *Ann. Rev. Biochem.* 61: 387); for example, by adding internal cysteine residues capable of forming intramolecular disulfide bridges which cyclize the peptide.

Peptide Preparation.

The peptides used in this invention are chemically synthesized using standard chemical peptide synthesis techniques or, particularly where the peptide does not comprise "D" amino acid residues, are recombinantly expressed. In preferred embodiments the peptides are chemically synthesized by any of a number of fluid or solid phase peptide synthesis techniques known to those of skill in the art. Solid phase synthesis in which the C-terminal amino acid of the sequence is attached to an insoluble support followed by sequential addition of the remaining amino acids in the sequence is a preferred method for the chemical synthesis of the polypeptides of this invention. Techniques for solid phase synthesis are well known to those of skill in the art and are described, for example, by Barany and Merrifield (1963) *Solid-Phase Peptide Synthesis;* pp. 3–284 in *The Peptides: Analysis, Synthesis, Biology. Vol. 2: Special Methods in Peptide Synthesis, Part A.;* Merrifield et al. (1963) *J. Am. Chem. Soc.,* 85: 2149–2156, and Stewart et al. (1984) *Solid Phase Peptide Synthesis,* 2nd ed. Pierce Chem. Co., Rockford, Ill.

In a most preferred embodiment, the peptides are synthesized by the solid phase peptide synthesis procedure using a benzhyderylamine resin (Beckman Bioproducts, 0.59 mmol of $NH_2$/g of resin) as the solid support. The COOH terminal amino acid (e.g., t-butylcarbonyl-Phe) is attached to the solid support through a 4-(oxymethyl)phenacetyl group. This is a more stable linkage than the conventional benzyl ester linkage, yet the finished peptide can still be cleaved by hydrogenation. Transfer hydrogenation using formic acid as the hydrogen donor is used for this purpose. Detailed protocols used for peptide synthesis and analysis of synthesized peptides are describe in a miniprint supplement accompanying Anantharamaiah et al. (1985) *J. Biol. Chem.,* 260(16): 10248–10255.

It is noted that in the chemical synthesis of peptides, particularly peptides comprising D amino acids, the synthesis usually produces a number of truncated peptides in addition to the desired full-length product. The purification process (e.g. HPLC) typically results in the loss of a significant amount of the full-length product.

It was a discovery of this invention that, in the synthesis of a D peptide (e.g. D-4), in order to prevent loss in purifying the longest form one can dialyze and use the mixture and thereby eliminate the last HPLC purification. Such a mixture loses about 50% of the potency of the highly purified product (e.g. per wt of protein product), but the mixture contains about 6 times more peptide and thus greater total activity.

D-form Amino Acids.

D-amino acids are incorporated at one or more positions in the peptide simply by using a D-form derivatized amino acid residue in the chemical synthesis. D-form residues for solid phase peptide synthesis are commercially available from a number of suppliers (see, e.g., Advanced Chem Tech, Louisville; Nova Biochem, San Diego; Sigma, St Louis; Bachem California Inc., Torrance, etc.). The D-form amino acids can be incorporated at any position in the peptide as desired. Thus, for example, in one embodiment, the peptide can comprise a single D-amino acid, while in other embodiments, the peptide comprises at least two, generally at least three, more generally at least four, most generally at least five, preferably at least six, more preferably at least seven and most preferably at least eight D amino acids. In particularly preferred embodiments, essentially every other (enantiomeric) amino acid is a D-form amino acid. In certain embodiments at least 90%, preferably at least 90%, more preferably at least 95% of the enantiomeric amino acids are D-form amino acids. In one particularly preferred embodiment, essentially every enantiomeric amino acid is a D-form amino acid.

Protecting Groups.

In certain embodiments, the one or more R-groups on the constituent amino acids and/or the terminal amino acids are blocked with a protecting group. Without being bound by a particular theory, it was a discovery of this invention that blockage, particularly of the amino and/or carboxyl termini of the subject peptides of this invention greatly improves oral delivery and significantly increases serum half-life.

A wide number of protecting groups are suitable for this purpose. Such groups include, but are not limited to acetyl, amide, and alkyl groups with acetyl and alkyl groups being particularly preferred for N-terminal protection and amide groups being preferred for carboxyl terminal protection. In certain particularly preferred embodiments, the protecting groups include, but are not limited to alkyl chains as in fatty acids, propeonyl, formyl, and others. Particularly preferred carboxyl protecting groups include amides, esters, and ether-forming protecting groups. In one preferred embodiment, an acetyl group is used to protect the amino terminus and an amide group is used to protect the carboxyl terminus. These blocking groups enhance the helix-forming tendencies of the peptides. Certain particularly preferred blocking groups include alkyl groups of various lengths, e.g. groups having the formula: $CH_3$—$(CH_2)_n$—$CO$— where n ranges from about 1 to about 20, preferably from about 1 to about 16 or 18, more preferably from about 3 to about 13, and most preferably from about 3 to about 10.

In certain particularly preferred embodiments, the protecting groups include, but are not limited to alkyl chains as in fatty acids, propeonyl, formyl, and others. Particularly preferred carboxyl protecting groups include amides, esters, and ether-forming protecting groups. In one preferred embodiment, an acetyl group is used to protect the amino terminus and an amide group is used to protect the carboxyl terminus. These blocking groups enhance the helix-forming tendencies of the peptides. Certain particularly preferred blocking groups include alkyl groups of various lengths, e.g groups having the formula: $CH_3$—$(CH_2)_nCO$— where n ranges from about 3 to about 20, preferably from about 3 to about 16, more preferably from about 3 to about 13, and most preferably from about 3 to about 10.

Other protecting groups include, but are not limited to Fmoc, t-butoxycarbonyl (t-BOC), 9-fluoreneacetyl group, 1-fluorenecarboxylic group, 9-florenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethylbenzenesulphonyl (Mtr), Mesitylene-2-sulphonyl (Mts), 4,4-dimethoxybenzhydryl (Mbh),Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), Benzyloxymethyl (Bom), cyclohexyloxy (cHxO), t-butoxymethyl (Bum), t-butoxy (tBuO), t-Butyl (tBu), Acetyl (Ac), and Trifluoroacetyl (TFA).

Protecting/blocking groups are well known to those of skill as are methods of coupling such groups to the appropriate residue(s) comprising the peptides of this invention (see, e.g., Greene et al., (1991) *Protective Groups in Organic Synthesis,* 2nd ed., John Wiley & Sons, Inc. Somerset, N.J.). In one preferred embodiment, for example, acetylation is accomplished during the synthesis when the peptide is on the resin using acetic anhydride. Amide protection can be achieved by the selection of a proper resin for the synthesis. During the synthesis of the peptides described herein in the examples, rink amide resin was used. After the completion of the synthesis, the semipermanent protecting groups on acidic bifunctional amino acids such as Asp and Glu and basic amino acid Lys, hydroxyl of Tyr are all simultaneously removed. The peptides released from such a resin using acidic treatment comes out with the n-terminal protected as acetyl and the carboxyl protected as $NH_2$ and with the simultaneous removal of all of the other protecting groups.

IV. Enhancing Peptide Uptake.

It was also a surprising discovery of this invention that when an all L amino acid peptide (e.g. otherwise having the sequence of the peptides of this invention) is administered in conjunction with the D-form (i.e. a peptide of this invention) the uptake of the D-form peptide is increased. Thus, in certain embodiments, this invention contemplates the use of combinations of D-form and L-form peptides in the methods of this invention. The D-form peptide and the L-form peptide can have different amino acid sequences, however, in preferred embodiments, they both have amino acid sequences of peptides described herein, and in still more preferred embodiments, they have the same amino acid sequence.

It was also a discovery of this invention that concatamers of the class A amphipathic helix peptides of this invention are also effective in mitigating one or more symptoms of atherosclerosis. The monomers comprising the concatamers can be coupled directly together or joined by a linker. In certain embodiments, the linker is an amino acid linker (e.g. a proline), or a peptide linker (e.g. $Gly_4Ser_3$). In certain embodiments, the concatamer is a 2 mer, more preferably a 3 mer, still more preferably a 4 mer, and most preferably 5 mer, 8 mer or 10 mer.

V. Pharmaceutical Formulations.

In order to carry out the methods of the invention, one or more peptides or peptide mimetics of this invention are administered to an individual diagnosed as having one or more symptoms of atherosclerosis, or as being at risk for atherosclerosis. The peptides or peptide mimetics can be administered in the "native" form or, if desired, in the form of salts, esters, amides, prodrugs, derivatives, and the like, provided the salt, ester, amide, prodrug or derivative is suitable pharmacologically, i.e., effective in the present method. Salts, esters, amides, prodrugs and other derivatives of the active agents may be prepared using standard procedures known to those skilled in the art of synthetic organic chemistry and described, for example, by March (1992) *Advanced Organic Chemistry; Reactions, Mechanisms and Structure,* 4th Ed. N.Y. Wiley-Interscience.

For example, acid addition salts are prepared from the free base using conventional methodology, that typically involves reaction with a suitable acid. Generally, the base form of the drug is dissolved in a polar organic solvent such as methanol or ethanol and the acid is added thereto. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Particularly preferred acid addition salts of the active agents herein are halide salts, such as may be prepared using hydrochloric or hydrobromic acids. Conversely, preparation of basic salts of the peptides or mimetics are prepared in a similar manner using a pharmaceutically acceptable base such as sodium hydroxide, potassium hydroxide, ammonium hydroxide, calcium hydroxide, trimethylamine, or the like. Particularly preferred basic salts include alkali metal salts, e.g., the sodium salt, and copper salts.

Preparation of esters typically involves functionalization of hydroxyl and/or carboxyl groups which may be present within the molecular structure of the drug. The esters are typically acyl-substituted derivatives of free alcohol groups, i.e., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides and prodrugs may also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety which results in a compound that is therapeutically inactive until modified by an individual's metabolic system.

The peptides or mimetics identified herein are useful for parenteral, topical, oral, or local administration, such as by aerosol or transdermally, for prophylactic and/or therapeutic treatment of atherosclerosis and/or symptoms thereof. The pharmaceutical compositions can be administered in a variety of unit dosage forms depending upon the method of administration. Suitable unit dosage forms, include, but are not limited to powders, tablets, pills, capsules, lozenges, suppositories, patches, nasal sprays, injectibles, implantable sustained-release formulations, etc.

The peptides and/or peptide mimetics of this invention are typically combined with a pharmaceutically acceptable carrier (excipient) to form a pharmacological composition. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the active agents, or excipients or other stabilizers and/or buffers.

Other physiologically acceptable compounds include wetting agents, emulsifying agents, dispersing agents or preservatives which are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the active agent(s) and on the particular physio-chemical characteristics of the active agent(s).

The excipients are preferably sterile and generally free of undesirable matter. These compositions may be sterilized by conventional, well known sterilization techniques.

In therapeutic applications, the compositions of this invention are administered to a patient suffering from one or more symptoms of atherosclerosis or at risk for atherosclerosis in an amount sufficient to cure or at least partially prevent or arrest the disease and/or its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the active agents of the formulations of this invention to effectively treat (ameliorate one or more symptoms) the patient.

The concentration of peptide or mimetic can vary widely, and will be selected primarily based on fluid volumes, viscosities, body weight and the like in accordance with the particular mode of administration selected and the patient's needs. Concentrations, however, will typically be selected to provide dosages ranging from about 0.1 or 1 mg/kg/day to about 50 mg/kg/day and sometimes higher. Typical dosages range from about 3 mg/kg/day to about 3.5 mg/kg/day, preferably from about 3.5 mg/kg/day to about 7.2 mg/kg/day, more preferably from about 7.2 mg/kg/day to about 11.0 mg/kg/day, and most preferably from about 11.0 mg/kg/day to about 15.0 mg/kg/day. It will be appreciated that such dosages may be varied to optimize a therapeutic regimen in a particular subject or group of subjects.

In certain preferred embodiments, the peptides or peptide mimetics of this invention are administered orally (e.g. via a tablet) or as an injectable in accordance with standard methods well known to those of skill in the art. In other preferred embodiments, the peptides, may also be delivered through the skin using conventional transdermal drug delivery systems, i.e., transdermal "patches" wherein the active agent(s) are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the active agent(s) and any other materials that are present.

Other preferred formulations for topical drug delivery include, but are not limited to, ointments and creams. Ointments are semisolid preparations which are typically based on petrolatum or other petroleum derivatives. Creams containing the selected active agent, are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing.

Unlike typical peptide formulations, the peptides of this invention comprising D-form amino acids can be administered, even orally, without protection against proteolysis by stomach acid, etc. Nevertheless, in certain embodiments, peptide delivery can be enhanced by the use of protective excipients. This is typically accomplished either by complexing the polypeptide with a composition to render it resistant to acidic and enzymatic hydrolysis or by packaging the polypeptide in an appropriately resistant carrier such as a liposome. Means of protecting polypeptides for oral delivery are well known in the art (see, e.g., U.S. Pat. No. 5,391,377 describing lipid compositions for oral delivery of therapeutic agents).

Elevated serum half-life can be maintained by the use of sustained-release protein "packaging" systems. Such sustained release systems are well known to those of skill in the art. In one preferred embodiment, the ProLease biodegradable microsphere delivery system for proteins and peptides (Tracy (1998) Biotechnol. Prog. 14: 108; Johnson et al. (1996), Nature Med. 2: 795; Herbert et al. (1998), Pharmaceut. Res. 15, 357) a dry powder composed of biodegradable polymeric microspheres containing the protein in a polymer matrix that can be compounded as a dry formulation with or without other agents.

The ProLease microsphere fabrication process was specifically designed to achieve a high protein encapsulation efficiency while maintaining protein integrity. The process consists of (i) preparation of freeze-dried protein particles from bulk protein by spray freeze-drying the drug solution with stabilizing excipients, (ii) preparation of a drug-polymer suspension followed by sonication or homogenization to reduce the drug particle size, (iii) production of frozen drug-polymer microspheres by atomization into liquid nitrogen, (iv) extraction of the polymer solvent with ethanol, and (v) filtration and vacuum drying to produce the final dry-powder product. The resulting powder contains the solid form of the protein, which is homogeneously and rigidly dispersed within porous polymer particles. The polymer most commonly used in the process, poly(lactide-co-glycolide) (PLG), is both biocompatible and biodegradable.

Encapsulation can be achieved at low temperatures (e.g., −40° C.). During encapsulation, the protein is maintained in the solid state in the absence of water, thus minimizing water-induced conformational mobility of the protein, preventing protein degradation reactions that include water as a reactant, and avoiding organic-aqueous interfaces where proteins may undergo denaturation. A preferred process uses solvents in which most proteins are insoluble, thus yielding high encapsulation efficiencies (e.g., greater than 95%).

In another embodiment, one or more components of the solution can be provided as a "concentrate", e.g., in a storage container (e.g., in a premeasured volume) ready for dilution, or in a soluble capsule ready for addition to a volume of water.

The foregoing formulations and administration methods are intended to be illustrative and not limiting. It will be appreciated that, using the teaching provided herein, other suitable formulations and modes of administration can be readily devised.

VI. Additional Pharmacologically Active Agents.

Additional pharmacologically active agents may be delivered along with the primary active agents, e.g., the peptides of this invention. In one embodiment, such agents include, but are not limited to agents that reduce the risk of atherosclerotic events and/or complications thereof. Such agents include, but are not limited to beta blockers, beta blockers and thiazide diuretic combinations, statins, aspirin, ace inhibitors, ace receptor inhibitors (ARBs), and the like.

Suitable beta blockers include, but are not limited to cardioselective (selective beta 1 blockers), e.g., acebutolol (Sectral™), atenolol (Tenormin™), betaxolol (Kerlone™), bisoprolol (Zebeta™), metoprolol (Lopressor™), and the like. Suitable non-selective blockers (block beta 1 and beta 2 equally) include, but are not limited to carteolol (Cartrol™), nadolol (Corgard™), penbutolol (Levatol™), pindolol (Visken™), propranolol (Inderal™), timolol (Blockadren™), labetalol (Normodyne™, Trandate™), and the like.

Suitable beta blocker thiazide diuretic combinations include, but are not limited to Lopressor HCT, ZIAC, Tenoretic, Corzide, Timolide, Inderal LA 40/25, Inderide, Normozide, and the like.

Suitable statins include, but are not limited to pravastatin (Pravachol/Bristol-Myers Squibb), simvastatin (Zocor/Merck), lovastatin (Mevacor/Merck), and the like.

Suitable ace inhibitors include, but are not limited to captopril (e.g. Capoten™ by Squibb), benazepril (e.g., Lotensin™ by Novartis), enalapril (e.g., Vasotec™ by Merck), fosinopril (e.g., Monopril™ by Bristol-Myers), lisinopril (e.g. Prinivil™ by Merck or Zestril™ by Astra-Zeneca), quinapril (e.g. Accupril™ by Parke-Davis), ramipril (e.g., Altace™ by Hoechst Marion Roussel, King Pharmaceuticals), imidapril, perindopril erbumine (e.g., Aceon™ by Rhone-Polenc Rorer), trandolapril (e.g., Mavik™ by Knoll Pharmaceutical), and the like. Suitable ARBS (Ace Receptor Blockers) include but are not limited to losartan (e.g. Cozaar™ by Merck), irbesartan (e.g., Avapro™ by Sanofi), candesartan (e.g., Atacand™ by Astra Merck), valsartan (e.g., Diovan™ by Novartis), and the like.

VII. Kits for the Amelioration of One or More Symptoms of Atherosclerosis.

In another embodiment this invention provides kits for amelioration of one or more symptoms of atherosclerosis or for the prophylactic treatment of a subject (human or animal) at risk for atherosclerosis. The kits preferably comprise a container containing one or more of the peptides or peptide mimetics of this invention. The peptide or peptide mimetic may be provided in a unit dosage formulation (e.g. suppository, tablet, caplet, patch, etc.) and/or may be optionally combined with one or more pharmaceutically acceptable excipients.

The kit can, optionally, further comprise one or more other agents used in the treatment of heart disease and/or atherosclerosis. Such agents include, but are not limited to, beta blockers, vasodilators, aspirin, statins, ace inhibitors or ace receptor inhibitors (ARBs) and the like, e.g. as described above.

In addition, the kits optionally include labeling and/or instructional materials providing directions (i.e., protocols) for the practice of the methods or use of the "therapeutics" or "prophylactics" of this invention. Preferred instructional materials describe the use of one or more polypeptides of this invention to mitigate one or more symptoms of atherosclerosis and/or to prevent the onset or increase of one or more of such symptoms in an individual at risk for atherosclerosis. The instructional materials may also, optionally, teach preferred dosages/therapeutic regiment, counter indications and the like.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Several synthetic class A peptide analogs have been shown to mimic many of the properties of human apo A-I in vitro. In this example, a new peptide (5F) with increased amphipathicity, was given by intraperitoneal injection, 20 IIg/daily, for 16 weeks to C57BL/6J mice fed an atherogenic diet. Mouse apo A-I (MoAI) (50 IIg/daily) or phosphate buffer saline (PBS) injections were given to other mice as controls. Total plasma cholesterol levels and lipoprotein profiles were not significantly different among the treated group and the control groups except that the mice receiving 5F or MoAI had lower high density lipoprotein (HDL)-cholesterol when calculated as a percent of total cholesterol. No toxicity or production of antibodies to the injected materials was observed. When LDL was taken from animals injected with 5F and presented to human artery wall cells in vitro it produced less lipid hydrodroperoxides and less LDL-induced chemotactic activity than LDL taken from controls. Additionally, when HDL was taken from mice injected with 5F and presented to human artery wall cells in vitro together with human LDL, there were substantially less lipid hydroperoxides formed and substantially less LDL-induced monocyte chemotactic activity. Mice receiving peptide 5F had significantly less aortic atherosclerotic lesion area compared to mice receiving PBS. Lesion area in mice receiving MoAI was similar to that of the PBS-injected animals. We conclude that 5F may have potential in the prevention and treatment of atherosclerosis.

Materials and Methods

Peptides

Peptide 5F (Ac-18A[Asp Trp Leu Lys Ala Phe Tyr Asp Lys Val Phe Glu Lys Phe Lys Glu Phe Phe]-$NH_2$, SEQ ID NO:13) was synthesized by solid-phase peptide synthesis (see, e.g., Anantharamaiah and Garber (1996) Meth. Enzymol. 263: 267–282; Palgunachari et al. (1996) Arteriosclerosis, Thrombosis, & Vascular Biology 16: 328–338). The purity of the synthetic peptide was established by analytical HPLC and ion-spray mass spectrometry. The peptide was dialyzed against distilled water and lyophilized before using.

MoAI was isolated from the plasma of C57BL/6J mice (EDTA plasma was purchased from Harlan Bioproducts for Science, Indianapolis, Ind.). MoAI was isolated using a combination of size-exclusion and reversed-phase column chromatography. Briefly, plasma density was adjusted to 1.21 g/ml by addition of KBr, and centrifuged at 50,000 rpm for 24 hours at 4° C. (Ti70 rotor; Beckman, Fullerton, Calif.). The top fraction was collected, dialyzed against water to remove KBr, lyophilized, and delipidated. The pellet was dissolved in Gn:DTT:Tris solution (3 M guanidine HCl, 1 mM dithiothreitol, and 10 mM Tris; pH=8.0), then dialyzed against the same solution using 12,000 MW-cutoff dialysis tubing in order to remove much of the apo A-II and C apolipoproteins from the sample. The sample was then dialyzed against water and lyophilized. The pellet was dissolved in fresh Gn:DTT:Tris solution, and proteins were separated by size-exclusion column chromatography, using an XK26/1 00 column (2.6×100 cm) packed with bulk-phase Superose 12 (Pharmacia Biotech, Piscataway, N.J.) equilibrated with Gn:DTT:Tris solution. The flow rate was 0.5 ml/min, and 2.5 ml fractions were collected. Fractions corresponding to the apo A-I peak were analyzed by SDS-PAGE, and further purified by preparative C-18 reverse-phase HPLC (Anantharamaiah and Garber (1996) *Meth. Enzymol.* 263: 267–282).

Mice

All experiments were performed using female C57BL/6J mice (Jackson Laboratory, Bar Harbor, Me.). Mice were purchased at six weeks of age, and the diet studies were begun with mice at eight weeks of age. Mice weighing 20 to 22 grams were used in the turnover studies. All animal studies were prospectively reviewed and approved by the Institutional Animal Care and Use Committee of the University of Alabama at Birmingham.

Kinetic Studies

The 5F peptide, MoAI, and human apo A-I were labeled with $^{125}$I by the method of Bilheimer et al. (1972) *Biochim. Biophys. Acta* 260: 212–221. Mice were placed on a modified Thomas-Hartroft atherogenic diet (#TD88051; Teklad, Madison, Wis.) for four weeks at which time daily intraperitoneal injections of peptide or protein dissolved in 200 μl phosphate-buffered saline (PBS) were begun. Animals injected with MoAI or human apo A-I received 50 μg per animal; those injected with 5F received 20 μg. Animals were not fasted for the kinetic studies and blood samples were taken under xylazine:ketamine anesthesia from the retro-orbital sinus at 15, 30, and 45 minutes, and 1, 1.5, 2, 3, 4, 6, 8, 12, and 24 hours following injection. Each animal provided three blood samples at different time points (all retro-orbital and alternating eyes), and at least three samples were collected (from different animals) at each time point. Samples were collected into heparinized capillary tubes, then placed in microcentrifuge tubes; the plasma was separated by centrifugation. Duplicate 10 μl aliquots of each sample were taken for radioactivity determination, using gamma counting (Cobra; Packard Instruments, Downers Grove, Ill.) for 10 minutes per sample. Total plasma volume was calculated as 4.2% body weight. Each sample was expressed as percent of injected CPM in total plasma. Free $^{125}$I was determined by trichloroacetic acid (TCA) precipitation (1 ml of 10% TCA per 10 μl plasma sample). Fitting to the kinetic model was done using all data points, rather than averages at each time point (PKAnalyst, MicroMath Scientific Software, Salt Lake City, Utah).

Injection Protocol and Sample Collection for Lesion Studies

Mice were acquired at six weeks of age, and randomized into groups of 20, except that a negative control group of 10 received no treatments and was given standard rodent chow. At eight weeks of age, the treatment groups were placed on a modified Thomas-Hartroft atherogenic diet (#TD88051; Teklad, Madison, Wis.), and injections were begun. The diet was stored at 4° C. and was used for no longer than three months after the manufacture date in order to minimize lipid oxidation. Animals were injected intraperitoneally daily for 16 weeks, including weekends and holidays. Twenty mice in each group received daily injections of 200 ΠPBS (as positive controls), or 20 Πg 5F in 200 Π PBS, or 50 Πg MoAI in 200 Π PBS.

Lyophilized 5F peptide was prepared in vials, with each bottle containing sufficient peptide for one day's injection. The 5F peptide was lyophilized in PBS, and was dissolved in autoclaved Milli-Q water (Millipore Corp., Bedford, Mass.) on the day of injection. The injection volume for all groups was maintained at 200 μl/mouse per day.

Blood samples were taken under anesthesia by retro-orbital bleeding at study entry (pre-diet) and at the time of organ harvesting. At the end of the study (week 16), at the last bleeding, the heart and the liver were excised. The hearts were kept in 0.9% saline solution for about 1 hour to eliminate blood and to permit the heart muscle to relax. They were then fixed in phosphate-buffered 4% formaldehyde for at least one week until sectioned. The livers were removed and weighed.

Histological Evaluation

Histological evaluations were performed according to the method of Paigen et al. (Paigen et al. (1990) *Arteriosclerosis* 10: 316–323) with some modifications. Briefly, hearts were fixed for at least one week in the phosphate-buffered formaldehyde solution. After removing the lower ⅔ of the hearts, the remaining tissue was frozen in OCT medium (Tissue-Tek, Miles Inc., Elkhart, Ind.) and sectioned in a cryostat at −20° C. Alternate 20 μm sections were saved on slides, and observed for the beginning of the aortic root. Sections were then collected for an additional 600 μm, or until the aortic cross-section was rounded and the valve cusps were no longer evident. Slides were stained with Oil Red O, and counterstained with hematoxylin. Stained lesion cross-sectional areas were measured in consecutive slides 80 μm apart by image analysis (SigmaScan Pro, SPSS Scientific, Chicago, Ill.), and the average lesion area was determined for each aortic sinus over the 400 μm length (five slides) providing the greatest mean lesion area.

Cocultures, Monocyte Isolation, Isolation of Lipoproteins, Determination of Lipid Hydroperoxides, and Monocyte Chemotactic Activity Cocultures of human artery wall cells, monocyte isolation, isolation of lipoproteins by ultracentrifugation from the plasma of normal human donors or from mouse plasma by FPLC, and determination of lipid hydroperoxides and monocyte chemotactic activity were performed according to standard methods. All human subject participation was with informed consent approved by the UCLA Human Subjects Protection Committee. The protocol for testing mouse lipoproteins in the coculture was also performed as follows: Briefly, LDL and HDL were isolated by FPLC from mouse plasma from mice fed the atherogenic diet and injected with vehicle (PBS), or with peptide 5F at 20 μg/mouse/day. The cocultures were treated with human LDL at 200 μg/ml LDL protein, or mouse LDL at 200 μg/ml or with 200 μg/ml human LDL+human HDL at 350 μg/ml of HDL protein or mouse HDL at 300 μg/ml or with mouse HDL alone at 300 Πg/ml. The cocultures were incubated with or without the above additions for 8 hrs at 37° C. in the presence of 10% lipoprotein deficient serum (LPDS). The supernatants were collected and analyzed for Auerbach lipid hydroperoxide equivalents. The cocultures were then washed and incubated with fresh culture medium without serum or LPDS for an additional 8 hrs. The conditioned medium was collected and analyzed for monocyte chemotactic activity.

Chemical and Analytical Methods-Column Cholesterol Lipoprotein Profiles (CLiP)

Plasma cholesterol lipoprotein profiles were measured using our recently-developed CLiP method (Garber et al. (2000) *J. Lipid Res.* 41:1020–1026). Briefly, 5 to 10 µl of plasma were analyzed using a single Superose 6 (Pharmacia, Piscataway N.J.) column. Immediately following the column, cholesterol reagent was introduced through a mixing tee, and the eluent:reagent mixture entered a post-column reaction coil. Cholesterol content of the eluent mixture was spectrophotometrically detected at 500 nm, and data points were collected into a computer. The resulting profiles were decomposed into component peaks and analyzed for relative area using PeakFit (SPSS Science, Chicago, Ill.); absolute cholesterol values for total cholesterol and each component peak were determined by comparison with a control sample of known values. In some cases fractions were collected to determine distribution of radioactivity. The CLiP method allowed analysis of individual mouse samples, avoiding the use of pooled samples.

Antibody Detection

To determine whether daily injections of peptides elicited any immune response in mice, indirect ELISA titration (Engvall (1980) *Meth. Enzymol.* 70:419–439) was carried out with plasma taken from mice at the time of organ collection (following sixteen weeks of daily injection). Plates were coated with the injected peptides or MoAI (10 Ilg/ml). Plates were incubated overnight. After thorough washing with borate buffered saline (pH 8.2) containing 0.05% Tween 20, and blocking with buffer (0.1% gelatin and 0.1% BSA in borate buffer) for 1 h, 200 µl of the diluted mouse plasma (1:100 dilution) samples were serially diluted 1:1 with borate-buffered saline. Biotinylated goat antibody to mouse IgG (0.1 Ilg/ml) was then added to the wells and the plates were treated with SA-HRP (Streptavidin-horseradish peroxidase) for an hour and developed with ABTS and peroxide as substrate. The plates were incubated overnight at room temperature after every addition of antigen/antibody and washed thoroughly with borate buffered saline (pH 8.2) containing 0.05% Tween 20, and blocked with buffer (0.1% gelatin and 0.1% BSA in borate buffer) for 1 h before the next addition.

Statistical Methods

Treatment groups were compared by two-tailed t-tests or one way analysis of variance (where the data were normally distributed), or by one way analysis of variance on ranks (SigmaStat; SPSS Science, Chicago, Ill.). Kinetics of peptide or protein turnover were analyzed by fitting to a first order one-compartment kinetic model assuming non-equal input and output rates (PKAnalyst; MicroMath Scientific Software, Salt Lake City, Utah).

Results

Kinetic Studies

The kinetics of the clearance of peptide 5F and human and mouse apo A-I from mouse plasma following intraperitoneal injection are summarized in Table 2.

TABLE 2

Summary of fitted data from kinetic experiments

| Injected Material | T½ (h) | Time (h) to max. CPM | Max. % in plasma | $r^2$ |
|---|---|---|---|---|
| Human apo A-I (50 µg/mouse) | 15.6 | 3.61 | 23.7 | 0.947 |
| Mouse apo A-I (50 µg) | 15.7 | 1.74 | 13.5 | 0.928 |
| 5F (20 µg) | 6.22 | 2.36 | 14.29 | 0.895 |

Data shown represent results of fitting data to a first order one-compartment kinetic model assuming unequal input and output rates (PKAnalyst; MicroMath Scientific Software, Salt Lake City, UT). Abbreviations: T½: half time of clearance from plasma; Max. % in plasma: percent of injected dose found in total plasma at peak levels; $r^2$: goodness of fit statistic of the kinetic model.

Figure 6A:
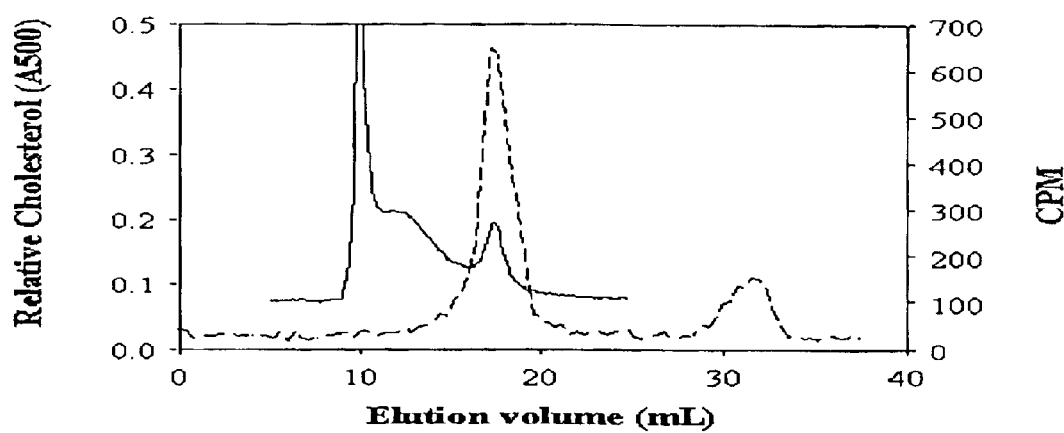
FIG. 6 illustrates the plasma distributions of peptide 5F or apo A-I following intraperitoneal injection. Human apo A-I, mouse apo A-I, and peptide 5F were labeled with $^{125}$I and injected intraperitoneally into C57BL/6 mice that had been fed the atherogenic diet for at least three weeks. Samples were taken during the kinetic studies described in Table 2. Representative samples were analyzed by the CLiP method, and fractions were collected for determination of radioactivity. The elution volume was based on the column pump rate only; the volume contributed by the enzymatic reagent pump was neglected. Data shown are cholesterol (as absorbance at 500 nm in arbitrary units; solid lines) and radioactivity (in counts per minute; dashed lines). Panels are A: human apo A-I (one hour following injection); B: mouse apo A-I (one hour), C: 5F (1.5 hours).
Figure 6B:
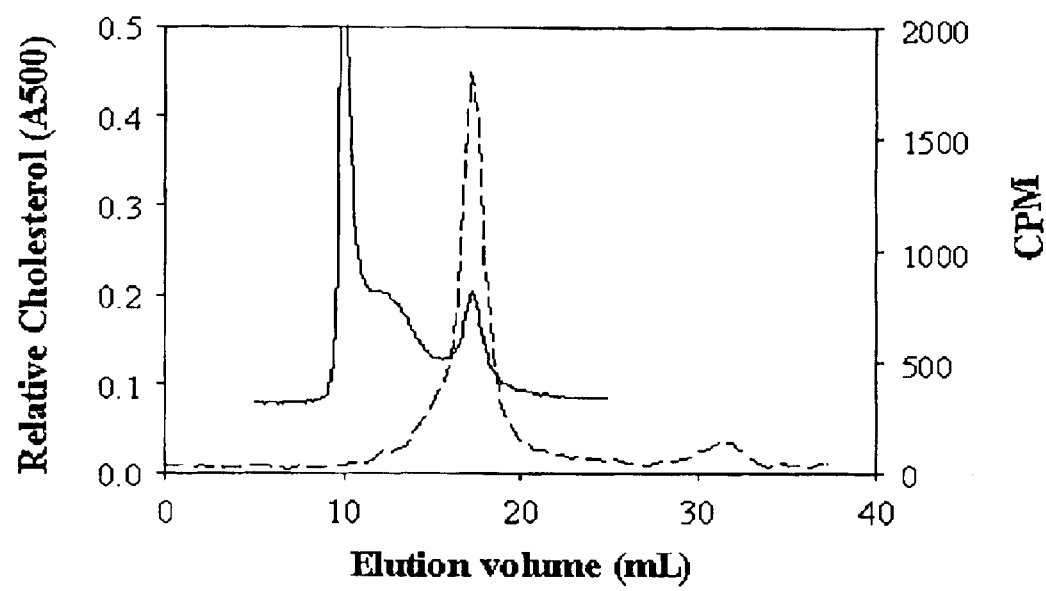
Figure 6C:
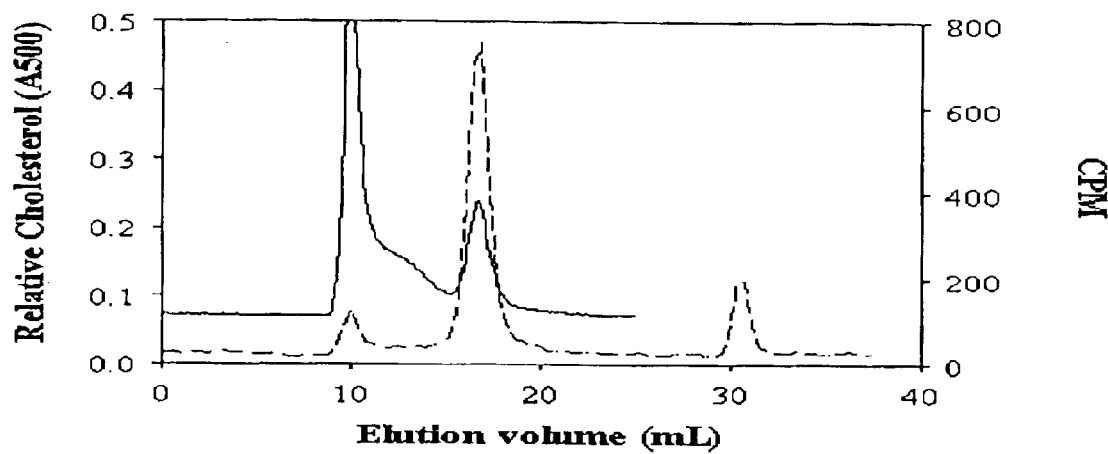

Human and mouse apo A-I had greatly prolonged clearance compared with the 5F peptide. Human apo A-I and 5F had longer times to peak plasma levels than did mouse apo A-I, although peak levels achieved were generally similar (human apo A-I reached higher peak levels than did the other materials). Analysis of plasma samples by column chromatography demonstrated that peptide 5F and apo A-I (both human and mouse) associated with plasma lipoproteins, especially with particles in the HDL-sized region (FIG. 6). The HDL:VLDL ratio of peptide radioactivity 1.5 h following injection of 5F was 4.19±0.58 (n=3, p<0.05). Similar results were found 5 h following injection of 5F (6.44±1.10, p<0.02). The injected peptide initially had less than 3% free $^{125}I$ by TCA precipitation. However, 1.5 hours after injection, free $^{125}I$ radioactivity in the plasma as a percent of total eluted radioactivity was substantially greater for 5F being 26.9±9.4% and at 5 hours 34.4±4.8%, reflecting the expected clearance of lipoproteins and lipoprotein-associated peptides. The rate of increase in the radioactivity due to free iodine from 1.5 to 5 hours was less than that from injection to 1.5 hours, possibly suggesting considerable initial degradation of the peptide in the peritoneal cavity.

Survival and Gross Morphology on the Chow or Atherogenic Diets

Only three mice died from unexplained causes during the course of the prolonged diet studies. Two of the animals had been receiving MoAI, and one was receiving 5F peptide. At the time of organ collection, no gross morphological differences were observed between the groups. Livers were enlarged in all animals fed the atherogenic diet, but neither liver weights nor liver weight as a percent of body weight were different between groups (Table 3). All animals on the atherogenic diet (including PBS-injected animals) had lower body weights than the chow-fed controls (Table 3).

TABLE 3

Body and liver weights following treatment.

| Diet & Subgroup | Body Weight (g) | Liver Weight (g) | Liver:Body (percentage) |
|---|---|---|---|
| Chow | 23.38 ± 0.52 | 0.99 ± 0.02 | 4.24 ± 0.04% |
| Atherogenic | | | |
| PBS (n = 14) | 20.55 ± 0.32* | 1.60 ± 0.04 | 7.84 ± 0.26% |
| 5F (n = 15) | 21.60 ± 0.28 | 1.61 ± 0.04 | 7.46 ± 0.23% |
| MoAI (n = 14) | 21.16 ± 0.34 | 1.72 ± 0.04 | 8.15 ± 0.23%* |

Data shown are mean ± SEM of weights taken at the time of organ harvesting (after 16 weeks of treatment). The chow-fed animals received no injections. The other mice were maintained on the atherogenic diet as described in Methods. The PBS group received intraperitoneal injections of 200 Il phosphate-buffered saline daily. The 5F group received intraperitoneal injections of 20 Ilg 5F in 200 l PBS daily and the MoAI group received 50 Ilg MoAI in 200 Il PBS daily.
*p < 0.005 vs 5F; two-tailed t-test Antigenicity Blood samples taken at the conclusion of the 16-week injection period were tested for the presence of antibodies against the peptides. No antibodies were detected against peptide 5F or against MoAI (data not shown). Cross experiments, where the ELISA plates were coated with peptides or protein which was not injected into the series of animals, produced results essentially identical to those in the direct determination of the presence of antibodies (data not shown).

Lipoprotein and Apolipoprotein Characterization

Figures 7A, 7B:
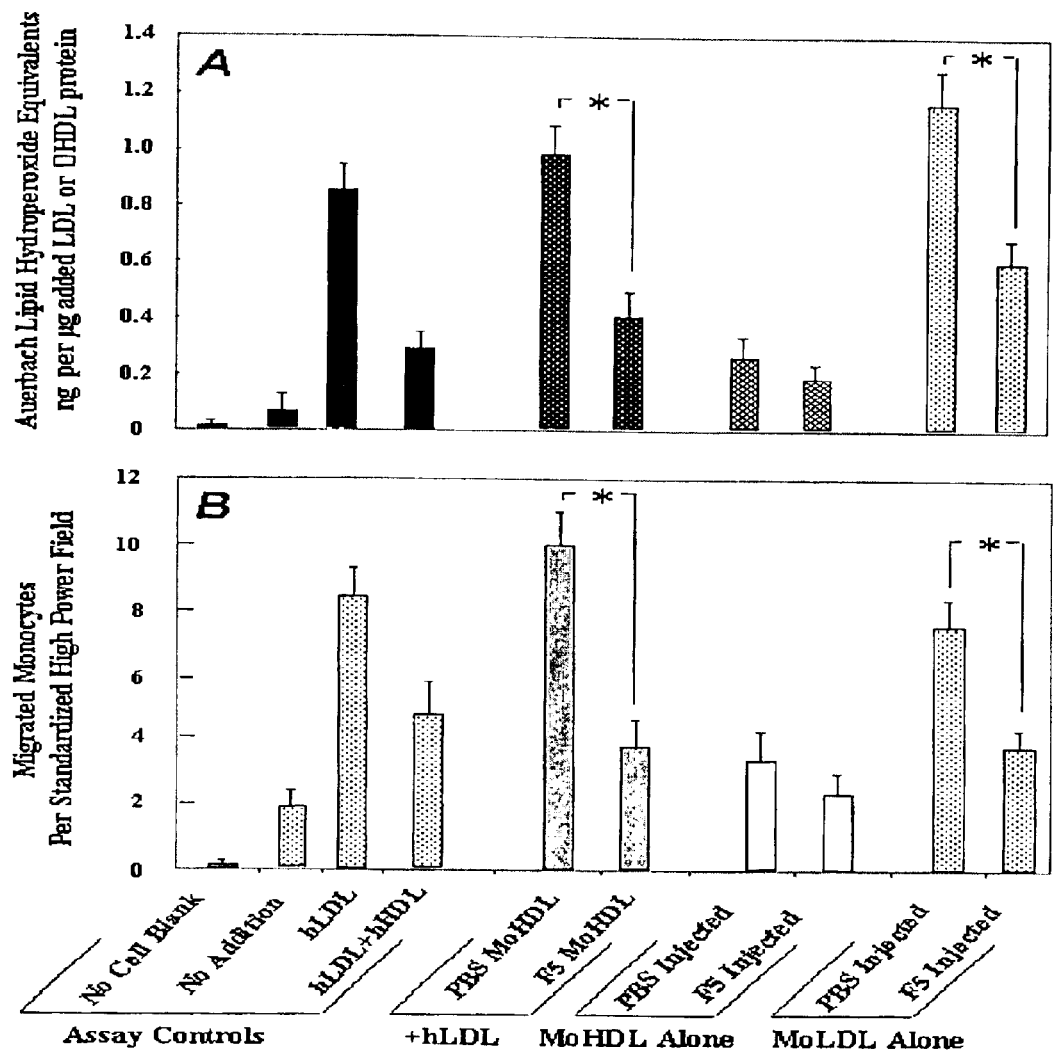
FIGS. 7A and FIG. 7B illustrate the interaction of mouse lipoproteins with human artery wall cells. LDL and HDL were isolated by FPLC from the plasma of mice fed the atherogenic diet and injected with vehicle (PBS), or with peptide 5F at 20 µg/mouse/day. The cocultures were treated without (No Addition) or with human LDL (HLDL) at 200 µg/ml LDL protein, or mouse LDL (MOLDL) at 200 µg/ml or with 200 µg/ml human LDL+ human HDL (hHDL) at 350 µg/ml of HDL protein or mouse HDL (MOHDL) at 300 µg/ml. The cocultures were incubated with the above additions for 8 hrs at 37° C. in the presence of 10% lipoprotein deficient serum (LPDS). The supernatants were collected and analyzed for Auerbach lipid hydroperoxide equivalents (FIG. 7A). The cocultures were then washed and incubated with fresh culture medium without serum or LPDS for an additional 8 hrs. The conditioned medium was collected and analyzed for monocyte chemotactic activity (FIG. 7B). A no cell blank (No Cell Blank) is included in both panels for comparison.

Total and lipoprotein cholesterol values as determined by the CLiP method are presented in Table 3. Accuracy of total cholesterol values was confirmed by a manual cholesterol assay (Cholesterol 1000; Sigma, St. Louis, Mo.) (data not shown). No significant differences in total or lipoprotein-fraction cholesterol levels were seen between the treatment groups. However, when lipoprotein fractions were expressed as a percent of total cholesterol (Table 4), HDL-cholesterol comprised a significantly lower percentage in the 5F and MoAI groups compared with the PBS group.

the present study that were fed the atherogenic diet and injected with PBS failed to inhibit the oxidation of human LDL (FIG. 7A) and failed to inhibit LDL-induced monocyte chemotactic activity (FIG. 7B) in human artery wall cocultures. In contrast, HDL from mice fed the atherogenic diet and injected daily with peptide 5F was as effective in inhibiting human LDL oxidation and preventing LDL-induced monocyte chemotactic activity in the cocultures as was normal human HDL. FIG. 7 also shows that LDL taken from mice fed the atherogenic diet and injected daily with PBS was more readily oxidized and more readily induced monocyte chemotactic activity than LDL taken from mice fed the same diet but injected with 20 Πg daily of peptide 5F. No cytotoxicity was noted in the artery wall cells treated with any of the lipoproteins (data not shown). Similar results were obtained in three of three separate experiments (data not shown).

Lesion Formation

Figure 8:
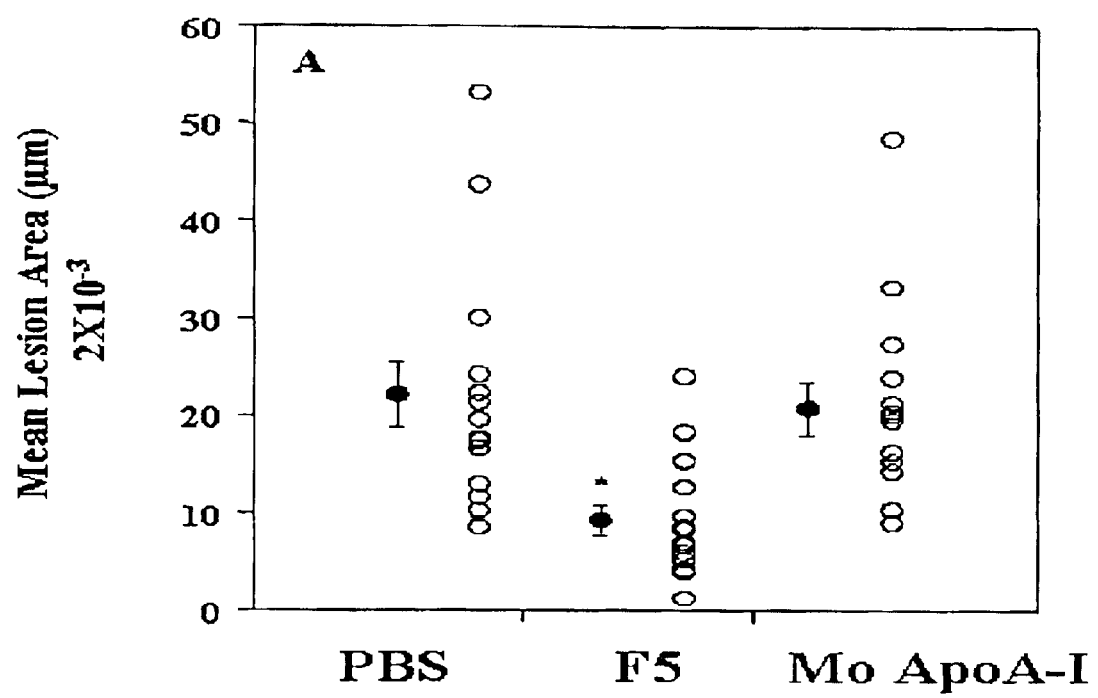
FIG. 8 shows mean lesion cross-sectional areas. Data shown represent the mean lesion cross-sectional area for each animal (○ and the mean±SEM of all animals in each group (●) with error bars. Abbreviations: PBS, mice fed the atherogenic diet and injected daily with 200 Π phosphate-buffered saline; 5F, mice fed the atherogenic diet and injected daily with 20 µg of 5F in 200 Π PBS; MoAI, mice fed the atherogenic diet and injected daily with 50 µg of mouse apo A-I in 200 Π PBS. *=p<0.002 as determined by two-tailed t-test. A significant difference was also shown using one way analysis of variance on ranks (p<0.001).

Mean lesion cross-sectional areas are presented in FIG. 8. As expected, no lesions were observed in the group given normal mouse chow (data not shown). As previously

TABLE 4

Total and lipoprotein cholesterol levels (mg/dl and percent of total cholesterol) after 16 weeks of chow or atherogenic diet.

|  | VLDL | IDL + LDL | HDL | TC |
|---|---|---|---|---|
| Chow Diet | 11.66 ± 2.34 (16.61 ± 3.55%) | 23.68 ± 3.51 (31.66 ± 3.61%) | 37.30 ± 2.52 (51.73 ± 1.75%) | 72.64 ± 5.58 |
| Atherogenic Diet |  |  |  |  |
| PBS | 88.36 ± 5.48 (47.26 ± 1.37%) | 75.82 ± 7.64 (39.83 ± 1.34%) | 24.36 ± 2.19 (12.91 ± 0.68%) | 188.54 ± 14.22 |
| 5F | 100.34 ± 15.72 (47.96 ± 3.26%) | 83.37 ± 8.15 (42.80 ± 2.51%) | 17.92 ± 2.91 (9.24 ± 1.18%*) | 201.63 ± 25.21 |
| MoAI | 100.08 ± 9.73 (48.23 ± 2.75%) | 87.86 ± 8.34 (42.44 ± 2.46%) | 19.50 ± 3.07 (9.34 ± 1.19%*) | 207.45 ± 16.94 |

Data are expressed as mean mg/dl ± SEM and, in parentheses, as percent of total cholesterol. Abbreviations: VLDL, very low density lipoprotein; IDL, intermediate density lipoprotein; LDL, low density lipoprotein; HDL, high density lipoprotein; TC, total cholesterol; MoAI, mouse apo A-I; PBS, Phosphate buffered saline. The chow-fed animals received no injections. The other mice were maintained on the atherogenic diet as described in Methods. The PBS group received intraperitoneal injections of 200 Π PBS daily. The 5F group received intraperitoneal injections of 20 Πg 5F in 200 Π PBS daily and the MoAI group received 50 Πg MoA-I in 200 Π PBS daily. Numbers of animals are as shown in Table 3.
*$p < 0.05$ or less compared with PBS by two-tailed t-test.

Interaction of Mouse Lipoproteins with Human Artery Wall Cells

We recently discovered that normal HDL inhibits three steps in the formation of mildly oxidized LDL. In those studies (see, copending application U.S. Ser. No. 09/541,468, filed on Mar. 31, 2000) we demonstrated that treating human LDL in vitro with apo A-I or an apo A-I mimetic peptide (37pA) removed seeding molecules from the LDL that included HPODE and HPETE. These seeding molecules were required for cocultures of human artery wall cells to be able to oxidize LDL and for the LDL to induce the artery wall cells to produce monocyte chemotactic activity. We also demonstrated that after injection of apo A-I into mice or infusion into humans, the LDL isolated from the mice or human volunteers after injection/infusion of apo A-I was resistant to oxidation by human artery wall cells and did not induce monocyte chemotactic activity in the artery wall cell cocultures. FIG. 7 demonstrates that HDL from the mice in reported (Paigen et al. (1990) *Arteriosclerosis* 10: 316–323), considerable variations in lesion area were observed in all groups receiving the atherogenic diet. However, the 5F-injected animals had significantly lower mean lesion area than PBS-injected animals, whether analyzed by two-tailed t-test ($p<0.002$) or by one-way analysis of variance on ranks ($p<0.001$; determined due to the non-normal distribution of mean lesion areas). MoAI injection produced no difference in lesion area compared with PBS injection, and lesion area was significantly greater than in 5F-injected animals, both by t-test ($p<0.002$) and by one way analysis of variance on ranks ($p<0.001$).

Discussion

We previously demonstrated that synthetic peptides that were designed to mimic the class A amphipathic helical motif were able to associate with phospholipids, and exhibited many biological properties similar to human apo A-I (3,8,10,14,15, 20). We also have shown that when these peptides are administered intravenously in animals, they are found to be associated with plasma lipoproteins (11). This study was designed to address the hypothesis that a new peptide, 5F, with increased theoretical lipid affinity, would possess anti-atherogenic properties.

The studies presented here demonstrated that this peptide 5F entered the plasma after interperitoneal injection and achieved plasma levels that were roughly comparable to MoAI, but less than human apo A-I (Table 2 and FIG. 6). The plasma clearance half-time of 5F was shorter than either mouse or human apo A-I after peritoneal injection. After injection the majority of 5F was found in the region of HDL (FIG. 6), despite the fact that the preponderance of circulating cholesterol was in the VLDL-, IDL-, and LDL-sized regions on the atherogenic diet.

Plasma cholesterol levels and distributions were not significantly different among the injected groups on the atherogenic diet (Table 4). However, when the lipoprotein fractions were expressed as a percent of total cholesterol (Table 4), HDL-cholesterol comprised a significantly lower percentage in the 5F and MoAI groups compared with the PBS group.

Normal HDL inhibits three steps in the formation of mildly oxidized LDL. We demonstrated that treating human LDL in vitro with apo A-I or an apo A-I mimetic peptide removed seeding molecules from the LDL that included HPODE and HPETE. These seeding molecules were required for cocultures of human artery wall cells to be able to oxidize LDL and for the LDL to induce the artery wall cells to produce monocyte chemotactic activity (see copending copending application U.S. Ser. No. 09/541,468, filed on Mar. 31, 2000). We also demonstrated that after injection of apo A-I into mice or infusion into humans, the LDL isolated from the mice or human volunteers after injection/infusion of apo A-I was resistant to oxidation by human artery wall cells and did not induce monocyte chemotactic activity in the artery wall cell cocultures. In the present studies, HDL from mice that were fed the atherogenic diet and injected with PBS failed to inhibit the oxidation of human LDL (FIG. 7A) and failed to inhibit LDL-induced monocyte chemotactic activity (FIG. 7B) in the human artery wall cocultures. In stark contrast, HDL from mice fed the same atherogenic diet but injected with peptide 5F was found to be as effective in inhibiting human LDL oxidation and preventing LDL-induced monocyte chemotactic activity in the cocultures as was normal human HDL (FIG. 7). LDL taken from mice fed the atherogenic diet and injected with 5F was less readily oxidized and induced less monocyte chemotactic activity than LDL taken from mice fed the same diet but injected with PBS (FIG. 7). It is possible that 5F interacted with LDL in the circulation (either before or after associating with HDL) and removed seeding molecules necessary for LDL oxidation and LDL-induced monocyte chemotactic activity in a manner similar to that described in vitro for a related peptide, 37pA (copending copending application U.S. Ser. No. 09/541,468, filed on Mar. 31, 2000).

The in vitro responses of human artery wall cells to HDL and LDL from mice fed the atherogenic diet and injected with peptide 5F are consistent with the protective action of 5F in vivo. Despite, similar levels of total cholesterol, LDL-cholesterol, IDL+VLDL-cholesterol, and lower HDL-cholesterol as a percent of total cholesterol, the animals fed the atherogenic diet and injected with 5F had significantly lower lesion scores (FIG. 8). These results are somewhat analogous to those of Shah et al. (Shah et al. (1998) *Circulation* 97:780–785) who found that, despite persistence of hypercholesterolemia, apo A-I$_{Milano}$ prevented progression of atherosclerotic lesions in apo E-deficient mice.

The reason that human apo A-I has been used successfully to prevent/reduce atherosclerosis in animals (Wilson et al. (1988) *Arteriosclerosis* 8: 737–741; Rubin et al. (1991) *Nature* 353:265–267; Paszty et al. (1994) *J. Clin. Invest.* 94:899–903; Plump et al. (1994) *Proc. Natl. Acad. Sci. USA* 91:9607–9611; Shah et al. (1998) *Circulation* 97:780–785) but injection of MoAI at a dose of 50 IIg daily in these studies did not is not clear. It has been shown that MoAI does not form protein:lipid complexes as stable as does human apo A-I (Gong et al. (1994) *Biochim. Biophys. Acta* 1213:335–342). Mouse HDL has also been shown to be more easily denatured by guanidine hydrochloride than human HDL (Gong et al. (1994) *Biochim. Biophys. Acta* 1213:335–342) suggesting that amphipathic helical peptides might displace MoAI more easily from mouse HDL than human apo A-I from human HDL. These differences may or may not explain why MoAI did not significantly reduce lesions in this study. It may also be that a higher dose of MoAI is required under the conditions that we employed. In any event, the 5F peptide was highly effective under these conditions and MoAI was not.

The ELISA analysis of plasma at the conclusion of the injection protocol indicated that antibodies were not formed against the 5F peptide. This was not surprising in that lipid-associating peptides have been shown not to produce antibodies, presumably because these peptides bind lipids in such a way as to prevent the exposure of epitopes necessary to elicit an immune response (Muranishi (1997) *J. Pharm. Soc. Japan* 117:394–404; Fricker and Drewer (1996) *J Peptide Sci.* 2:195–211).

A preliminary study by us suggested that transgenic mice expressing a class A amphipathic helical peptide (37pA) with theoretically less lipid affinity than the peptide used in this study may have been resistant to atherosclerosis (Garber et al. (1997) *Circulation* 96:1–490). The current study suggests that peptide 5F likely has great potential for elucidating the mechanisms involved in atherogenesis and also has therapeutic potential.

Example 2

Efficacy of D Peptides

This example demonstrates the efficacy of D peptides of this invention. Human aortic wall cocultures were incubated with medium alone (LDL, NO CELLS or CELLS, NO LDL), control LDL from normal subjects at 250 μg/ml (LDL) and LDL plus control HDL from normal subjects at 350 μg/ml (+HDL). Other cocultures were incubated with the control LDL together with varying amounts (micrograms shown on the abscissa) of either D-2F, or L-2F (third panel from the left, 2F) or D-37-pA or L-37pA (last panel on the right, 37pA). The data represent mean p SD of values obtained from quadruplicate cocultures. Values for HDL or added peptides were all significantly different from LDL alone (first panel on the left) at the level of $p<0.01$.

Figure 9:
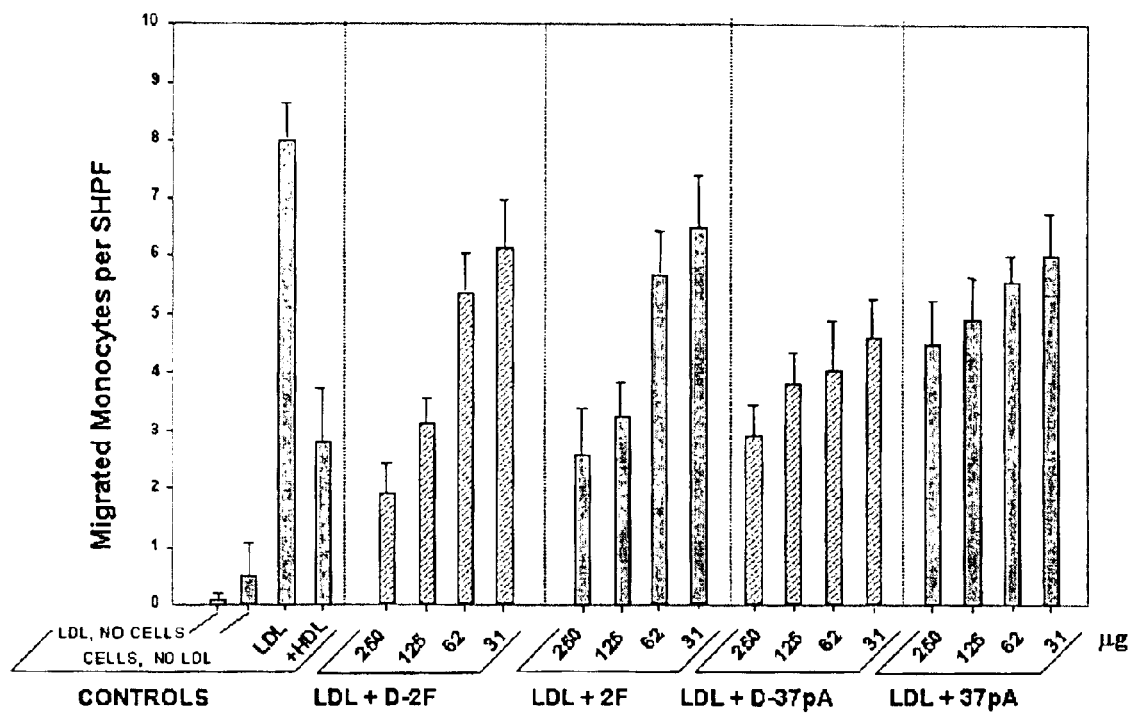
FIG. 9 shows that both the D and L isomers of apo A-I peptide mimetics prevent monocyte chemotactic activity induced by mildly oxidized LDL in vitro. Medium alone (LDL, NO CELLS or CELLS, NO LDL), control LDL from normal subjects at 250 µg/ml (LDL), and LDL plus control HDL from normal subjects at 350 µg/ml (+HDL). Other cocultures were incubated with the control LDL together with varying amounts (micrograms shown on the abscissa) of either D-2F, or L-2F (third panel from the left, 2F) or D-37-pA or L-37pA (last panel on the right, 37pA). The data represent mean ρ SD of values obtained from quadruplicate cocultures. Values for HDL or added peptides were all significantly different from LDL alone (first panel on the left) at the level of p<0.01.

The cocultures were incubated for 4 hrs at 37° C. in the presence of 10% LPDS to produce mildly oxidized LDL. The supernatants were then discarded, the cocultures were washed and incubated with culture medium without serum or LPDS for an additional 4 hrs. This conditioned medium was collected and analyzed for monocyte chemotactic activity. As shown in FIG. 9, treating LDL with the D peptides in vitro prevents their oxidation by artery wall cells.

Figure 10A:
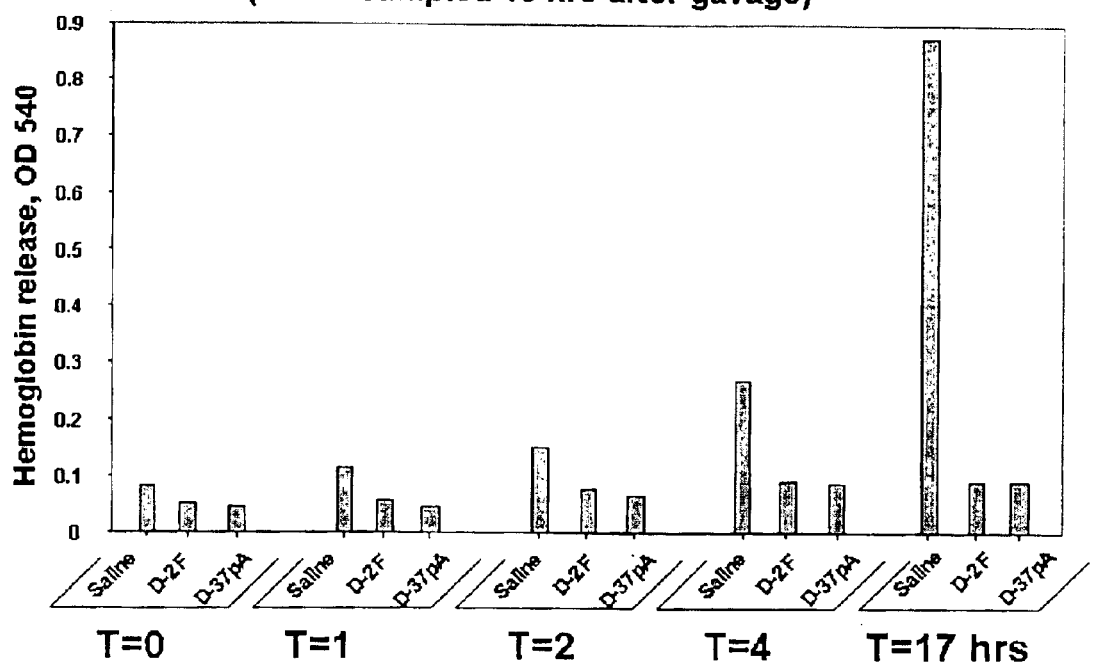
FIGS. 10A and 10B illustrate the results of in vitro red cell lysis assay at 18 hours (FIG. 10A) and at 48 hours (FIG. 10B). The asterisks reflect the presence of a significant difference (p<0001) between the red cell lysis for animals that received the vehicle vs those that received the peptides.
Figure 10B:
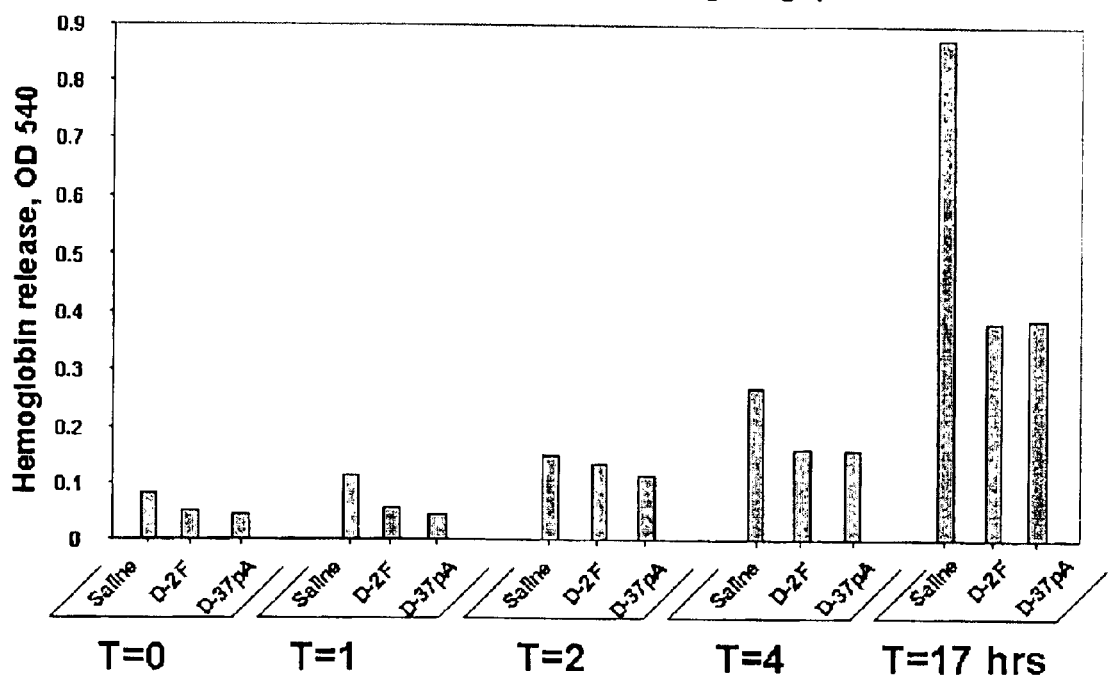

FIG. 10 demonstrates that giving the D peptides to mice renders their red blood cells resistant to hemolysis (a phenomenon due to oxidation as it can be prevented with Vitamin E, data not shown). Groups of LDL receptor deficient mice (n=3) commonly used as an animal model of atherosclerotic lesion formation were administered the D-peptides or the saline vehicle by gavage. Each animal was administered 100 μl of saline, 100 μg/100 μl of peptide D-2F or peptide D-37pA. Blood was collected from retroorbital sinus under mild anesthesia 17n and 48 hrs later. Red cells were separated by centrifugation, were diluted to 10% hematocrit with PBS and incubated at 37° C. with gentle mixing. Aliquots were removed at time points t=0, 2, 6 and 18 hrs, cell pellets spun down and the optical density due to the released hemoglobin determined.

Figure 11:
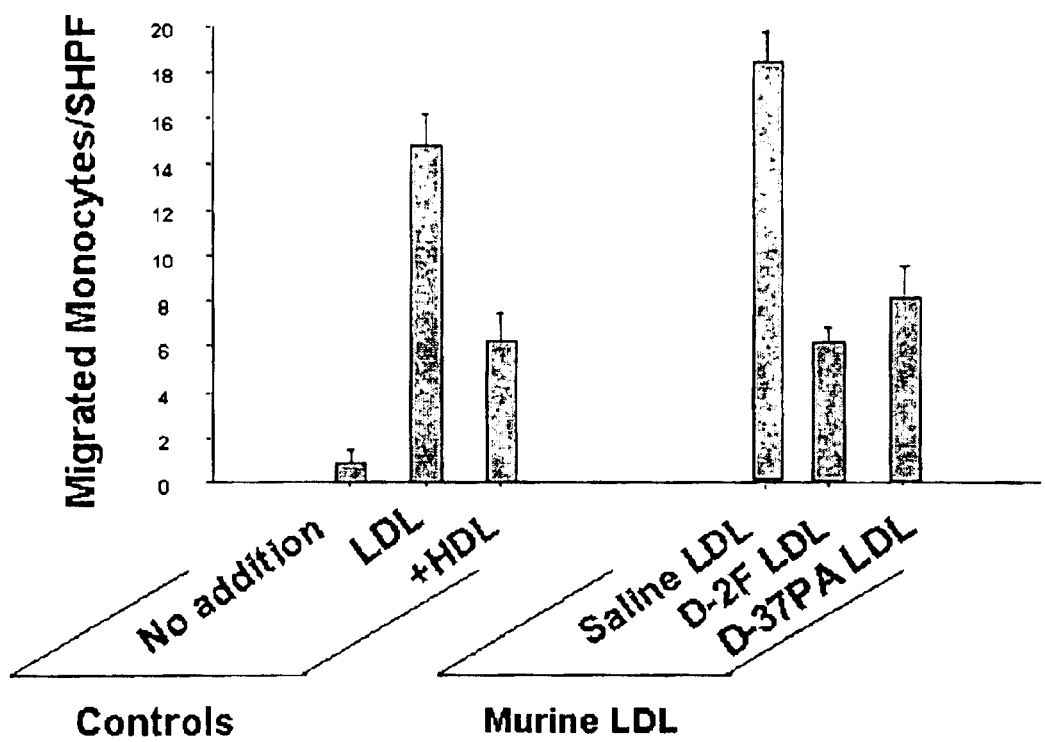
FIG. 11 illustrates the resistance of circulating LDL to oxidation following feeding of D-peptides. Groups of LDL receptor-deficient mice (n=3) were administered the D-peptides or the saline vehicle by gavage. Each animal was given 100 µl of saline, 100 µg/100 µl of peptide D-2F or peptide D-37pA. Blood was collected from retroorbital sinus under mild anesthesia 17 hrs later. LDL was isolated from plasma by FPLC. Cocultures of artery wall cells were incubated with medium alone (NO ADDITION), control LDL from normal subjects (LDL), LDL plus control HDL from normal subjects (+HDL). Other cocultures were incubated with murine LDL following gavage with saline (SALINE LDL), with D-2F (D-2F LDL) or with D-37pA peptide (D-37pA LDL). The cocultures were incubated for 4 hrs at 37° C. in the presence of 10% LPDS. The supernatants were then discarded, the cocultures were washed and incubated with culture medium without serum or LPDS for an additional 4 hrs. This conditioned medium was collected and analyzed for monocyte chemotactic activity. The values are mean±SD of quadruplicate cocultures. The asterisks indicate p<0.001.

FIG. 11 demonstrates that administering the D peptides to mice by gavage and then isolating their LDL renders the LDL resistant to artery wall cell oxidation as measured by the monocyte chemotaxis bioassay.

Figure 12:
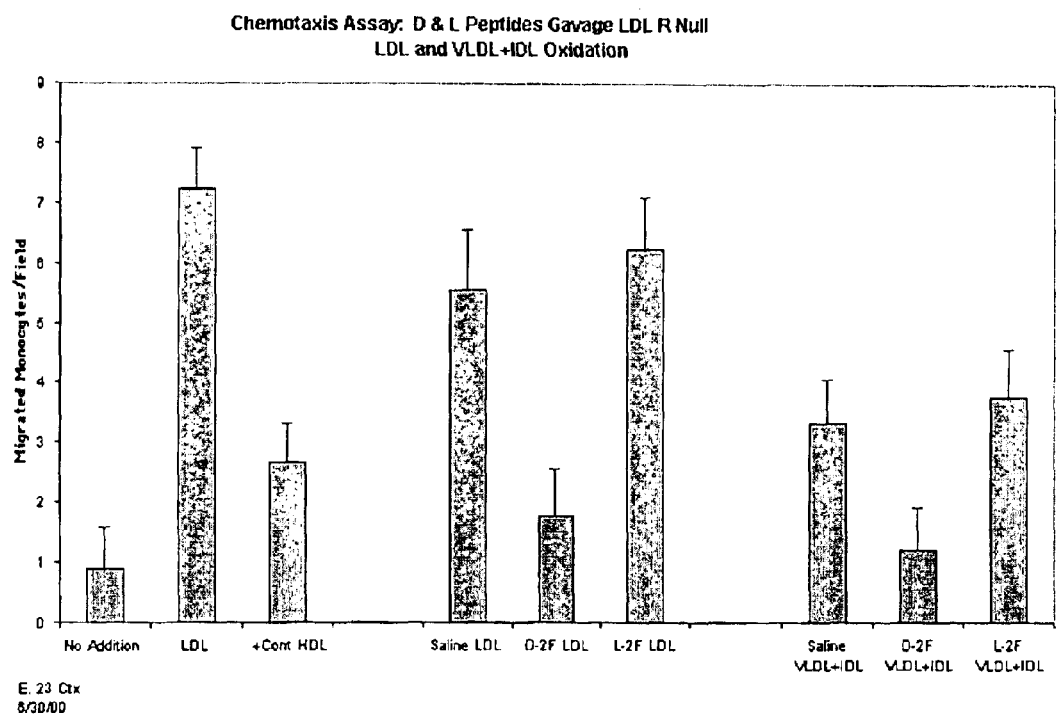
FIG. 12 illustrates the results of a chemotaxis assay comparing lipoproteins from mice given the D-form and or L-form peptides by gavage.

Another experiment demonstrated that the D-peptide was absorbed from the stomach and rendered LDL unable to induce monocyte chemotactic activity in our human artery wall cell coculture model while the L-peptide of 2F did not have this property. Either saline or 2F synthesized from D amino acids or from L amino acids was instilled in the stomachs of mice by gavage (instillation in the stomach by tube). After gavage the mice were bled and their LDL isolated and added to the human artery wall cell cocultures. The D-peptide when given by gavage protected the LDL as evidenced by the reduced monocyte chemotaxis induced by the LDL taken from the mice that received the D-2F peptide (D2FLDL) (synthesized from D amino acids), while the LDL taken from mice that received the L-2F (synthesized from the natural L amino acids) (L2FLDL) readily induced monocyte chemotaxis (see FIG. 12).

2F synthesized from L amino acids when presented to LDL in vitro was as effective as the 2F synthesized from the D amino acids (see FIG. 9). Thus, the difference in the results with this experiment where the peptides were given in vivo by gavage indicate that the 2F synthesized from D amino acids must have been absorbed intact from the stomach while the 2F peptide synthesized from the natural L amino acids must have been degraded in the stomach in the process of digestion and/or in the plasma as we hypothesized would be the case. In other studies we have not seen evidence of antibody formation against the D-2F peptide.

Figure 13A:
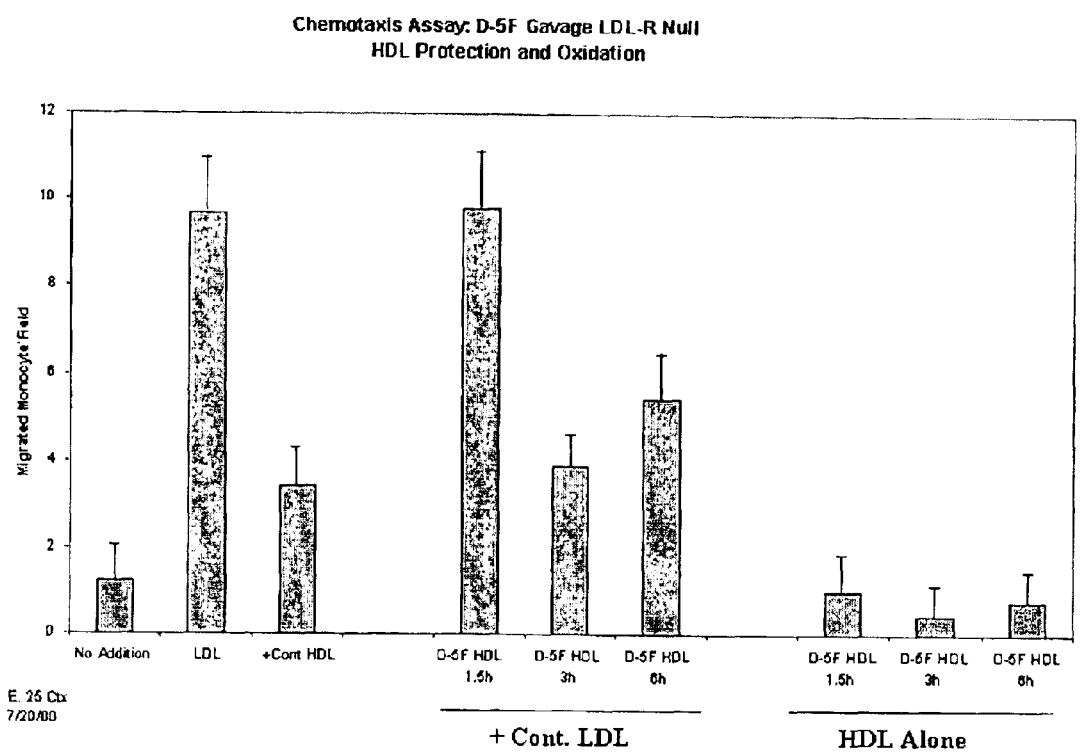
FIG. 13A illustrates the results of a chemotaxis assay comparing control HDL and HDL from mice given the D-peptide by gavage.
Figure 13B:
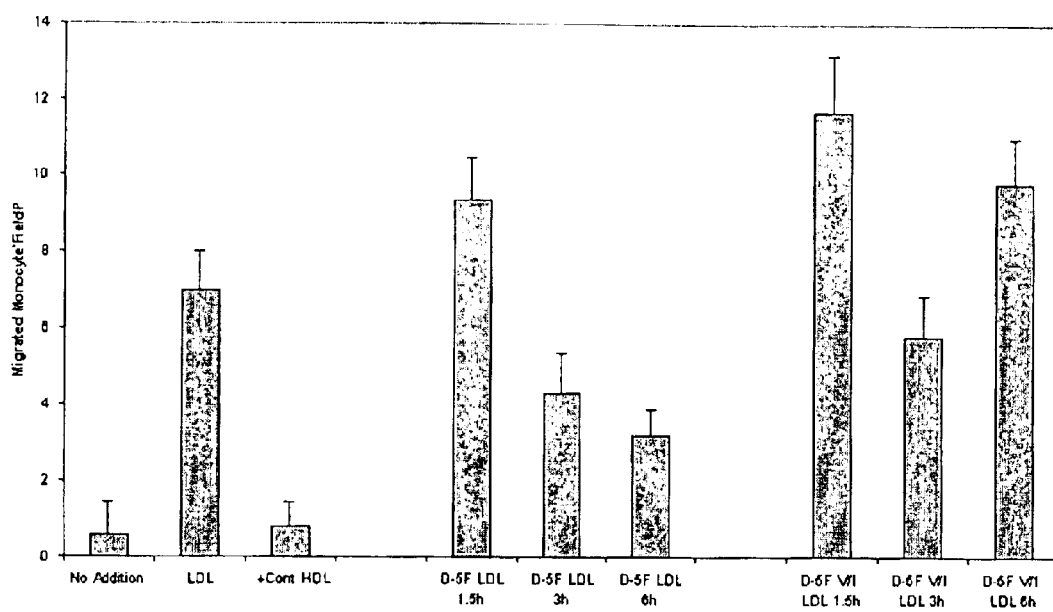
FIG. 13B illustrates the results of a chemotaxis assay comparing LDL and VLDL/IDL from mice given the D-peptide by gavage.

FIG. 13A and FIG. 13B are two graphs from experiments in which LDL receptor knockout mice were given 50 micrograms of D-5F by gavage. The animals were bled 1.5, 3 or 6 hours later and their HDL, LDL, and VLDL/IDL isolated. As indicated in the graph, HDL taken 1.5 hours after gavage did not protect control (cont.) LDL from modification but the HDL taken after 3 hours and slightly less after 6 hours following gavage were as protective against LDL-induced monocyte chemotactic activity production by human artery wall cells as a control HDL (FIG. 13A). In the other graph (FIG. 13B), 1.5, 3, or 6 h after administration of 50 micrograms of D-5F by gavage mouse LDL and VLDL/IDL were isolated. In the left panel a control LDL was added to the human artery wall cells without or with a control HDL and monocyte chemotactic activity produced by the artery wall cells was measured. In the middle panel the mouse LDL taken after 1.5, 3, or 6 hours after gavage of 50 micrograms of D-5F were added to the artery wall cells. The results indicate that after 3 h and 6 h the LDL induced significantly less monocyte chemotactic activity. On the right side of the graph the VLDL/IDL fraction of lipoproteins (V/I LDL) were added and as shown the 3 hour time point induced significantly less monocyte chemotactic activity.

Example 3

Effects of Increasing Hydrophobicity on the Physical-Chemical and Biological Properties of a Class A Amphipathic Helical Peptide List of Abbreviations $Ac_2O$, acetic anhydride; apo A-I, apolipoprotein A-I; BSA, Bovine serum albumin; CAD, coronary artery disease; CD, circular dichroism; DMPC, dimyristoyl phosphatidylcholine; DiPoPE, Di (16:1) palmitoleoyl phosphatidylethanolamine; DSC, Differential Scanning Calorimetry; EDTA, ethylene diamine tetraacetic acid; EPC, Egg phosphatidylcholine; FMOC, Fluorinylmethyloxycarbonyl; Gdn HCl, Guanidine Hydrochloride; HAEC, human aortic endothelial cells; HASMC, human aortic smooth muscle cells; HBTU, 2-(H-benzotriazole-1-yl)-1,1,3,3-tetramethyluronium hexafluorophosphate; HDL, high density lipoprotein; HPLC, High Performance Liquid Chromatography; LCAT, lecithin cholesterol acyl transferase; MCP-1, monocyte chemotactic protein-1; M-CSF, macrophage colony-stimulating factor; MLV multilamellar vesicles; NMM, N-methylmorpholine; PBS, phosphate buffered saline; PIPES, piperazine-N,N'-bis[2-ethanesulfonic acid]; RP-HPLC, reverse phase high performance liquid chromatography; TFA, trifloroacetic acid.

Abstract

We have recently shown that a class A amphipathic peptide 5F with increased amphipathicity protected mice from diet-induced atherosclerosis. We have now examined the effects of increasing the hydrophobicity of a series of homologous class A amphipathic peptides, including 5F, on physical and functional properties related to atherosclerosis inhibition by systematically replacing existing nonpolar amino acids with phenylalanine. The peptides, based on the sequence Ac-D-W-L-K-A-F-Y-D-K-V-A-E-K-L-K-E-A-F-$NH_2$ (SEQ ID NO:1, Ac-18A-$NH_2$or 2F) were: $3F^3$(Ac-$F^3$18A-$NH_2$), $3F^{14}$(Ac-$F^{14}$18A-$NH_2$), 4F(Ac-$F^{3,14}$18A-$NH_2$), 5F(Ac-$F^{11,14,17}$18A-$NH_2$), 6F(Ac-$F^{10,11,14,17}$18A-$NH_2$) and 7F(Ac-$F^{3,10,11,14,17}$18A-$NH_2$). Measurements of aqueous solubility, HPLC retention time, exclusion pressure for penetration into an egg PC monolayer, and rates of egg PC solubilization revealed an abrupt increase in the hydrophobicity between peptides 4F and 5F; this was accompanied by increased ability to associate with phospholipids. The peptides 6F and 7F were less effective, indicating a limit to increased hydrophobicity for promoting lipid interaction in these peptides. Despite this marked increase in lipid affinity, these peptides were less effective than apoA-I in activating the plasma enzyme, lecithin: cholesterol acyl transferase (LCAT), with 5F activating LCAT the best (80% of apoA-I). Peptides 4F, 5F and 6F were equally potent in inhibiting LDL-induced monocyte chemotactic activity. These studies suggest that an appropriate balance between peptide-peptide and peptide-lipid interactions is required for optimal biological activity of amphipathic peptides. These studies provide a rationale for the design of small apoA-I-mimetics with increased potency for atherosclerosis inhibition.

Introduction.

Plasma levels of high density lipoproteins (HDL) and apolipoprotein A-I (apo A-I), the major protein constituent of HDL, are inversely correlated to coronary artery disease (CAD) (Sprecher et al. (1993) *Arterioscler. Thromb.* 13: 495–504; Philips et al (1993) *Circulation* 88: 2762–2770). Human apo A-I is a 243 residue protein, containing eight 22-mer amphipathic helical repeats, the majority of which have been shown to possess the Class A motif (Segrest et al. (1990) *Proteins* 8: 103–117; Anantharamaiah et al. (1993) pp. 109–142 In: *The Amphipathic Helix (Epand, R. M., ed), CRC Press, Boca Raton, Fla.)*. Class A amphipathic helices have a characteristic charge distribution; they have a cluster of positively charged amino acids at the polar/nonpolar boundary of the Δ helix and negatively charged residues at the center of the polar face (Segrest et al. (1990) *Proteins* 8: 103–117; Anantharamaiah et al. (1993) pp. 109–142 In: *The Amphipathic Helix* (Epand, R. M., ed), CRC Press, BocaRaton, Fla.; Segrest et al. (1992) *J. Lipid Res.* 33: 141–166). This unique secondary structural motif has been postulated to be responsible for the lipid-associating property of apo A-I (Segrest et al. (1990) *Proteins* 8: 103–117). Many studies with synthetic analogues of Class A amphipathic helices have supported this concept (Segrest et al. (1994)*Adv. Prot. Chem.,* 45: 303–369; Brouillette and Anantharamaiah (1995) *Biochim. Biophys. Acta* 1256: 103–129). Recently, we have synthesized each of the putative 22 mer helices present in human apo A-I as monomers and tandem dimers and shown that the N- and C-terminal amphipathic helices possess the maximum lipid-associating ability (Mishra et al. (1998) *Biochemistry* 37: 10313–10324). X-ray crystal structure and molecular modeling studies of the exon 4 (44–243 residues) of apo A-I suggests that a self-associated state of the entire apo A-I is necessary for lipid association (Borhani et al. (1999) *Proc. Natl. Acad. Sci. USA.* 94:12291–12296; Segrest et al. (2000) *Current Opin. Lipidol.* 11:105–115). In this model, two molecules of apo A-I are arranged in the form of a head-to-tail dimer with the monomers interacting with each other to stabilize the lipid-associated structure of apo A-I.

Experimental evidence suggests that the protective effect of apo A-I and HDL against coronary artery disease could be due to their role in "reverse cholesterol transport" (Fielding and Fielding (1995) *J. Lipid Res.* 36: 211–228; Glomset (1968) *J. Lipid Res.* 9:155–167). Reverse cholesterol transport is the sum of three steps involving HDL/apo A-I, a) efflux of cholesterol from xx cells (Johnson et al. (1991) *Biochim. Biophys. Acta.* 1085: 273–298; Oram and Yokoyama (1996) *J. Lipid Res.* 37: 2473–2491), b) esterification by LCAT of HDL-associated cholesterol (Fielding et al. (1972) *Biochem. Biophys. Res. Comm.* 46: 1493–1498; Jonas (1991) *Biochim. Biophys. Acta* 1084: 205–220) and c) receptor-mediated delivery of cholesterol ester to the liver (Kreiger (1999) *Ann Rev. Biochem.* 68: 523–558). In vivo studies have shown that both human apo A-I and a class A synthetic amphipathic helical peptide inhibit atherosclerosis without altering plasma cholesterol levels by a mechanism that is independent of reverse cholesterol transport (Shah et al. (1998) *Circulation* 97: 780–785). Recently, we have suggested that inhibition of LDL-induced monocyte chemotaxis into artery wall cells has been suggested to be another major role played by apo A-I and HDL in preventing atherosclerosis (Navab et al. (2000) *J. Lipid Res.* 41: 1481–1494; Navab et al. (2000) *J. Lipid Res.* 41: 1495–1508).

A peptide that has been shown to mimic the properties of human apo A-I, 18A, has also been shown to possess LCAT activating (Anantharamaiah et al. (1990) *Arteriosclerosis* 10: 95–105; Epand et al. (1987) *J. Biol Chem.* 262: 9389–9396) and cholesterol effluxing abilities (Davidson et al. (1994) *J. Biol. Chem.* 269: 22975–22982; Yancey et al. (1995) *Biochemistry,* 34: 7955–7965). Neutralizing the terminal charges of 18A to form Ac-18A-NH$_2$ was shown to increase its lipid affinity, and biological activities (Yancey et al. (1995) *Biochemistry,* 34: 7955–7965; Venkatachalapathi et al. (1993) *Proteins: Structure, Function and Genetics.* 15: 349–359). Several modifications of the amino acid sequence of this 'parent' molecule, 18A, have been made in an attempt to improve its apo A-I mimicking properties (Brouillette and Anantharamaiah (1995) *Biochim. Biophys. Acta* 1256: 103–1291; Mishra et al. (1994) *J. Biol. Chem.* 269: 7185–7191; Mishra et al. (1995) *J. Biol. Chem.* 270: 1602–161 ). Our earlier studies (Brouillette and Anantharamaiah (1995) *Biochim. Biophys. Acta* 1256: 103–1291; Epand et al. (1987) *J. Biol. Chem.* 262: 9389–9396) have shown that an increase in the hydrophobicity of this peptide increases its lipid affinity and apo A-I-mimicking properties. A synthetic peptide 5F, an analog of Ac-18A-NH$_2$ with increased amphipathicity has been shown to inhibit diet-induced atherosclerosis in mice (see, e.g., Examples 1 and 2). However, the peptide 2F did not significantly inhibit diet-induced lesion formation in C57 BL6 mice (Garber et al. (1999) *Circulation* 100: 1538). A study of 18A dimer peptides indicated that increased peptide-peptide association decreased peptide:lipid association (Mishra et al. (1995) *J. Biol. Chem.* 270: 1602–1611). To determine the maximum extent to which the lipid affinity of the 18A peptide can be increased with a positive effect on lipid-associating and apo A-I-mimicking properties, we designed a homologous series of peptides in which Phe residues were systematically increased by substituting hydrophobic amino acids such as, Leu and Ala on the nonpolar face with Phe. According to the experimentally determined hydrophobicity scale of Wimley and White (Wimley and White (1996) *Nature Struc. Biol.* 3: 842–848), Trp and Phe are the most hydrophobic amino acids in the sense that they exhibit the greatest partitioning into the membrane from the aqueous phase. We elected to use Phe to increase the hydrophobicity of the peptide because it is the most acid-resistant hydrophobic amino acid in membrane active peptides and Phe-containing peptides can be synthesized more easily than Trp-containing peptides. The effects of this increase in hydrophobicity on the physical and lipid associating properties, and apo A-I-mimicking biological properties such as LCAT activation and inhibition of LDL-induced chemotactic activities, were studied.

Experimental Procedures.
Peptide Synthesis.

The peptides were synthesized by the solid phase method using an automated solid phase synthesizer (PS3 Protein Technologies, Woburn, Mass.). FMOC-amino acids were coupled to a rink amide resin [0.536 mEq/g], (Peninsula Laboratories, Inc. Belmont, Calif.) in the presence of HBTU and NMM, and acetylated with acetic anhydride at the N-terminus. The peptides were cleaved from the solid support using 70% TFA in dichloromethane in presence of anisole (1%), mercaptoeathanol (0.1%) and tryptophan (20% by weight of the peptide resin) and purified on a VYDAC C-4 (22 mm×25 cm, particle size 10 IIm) reversed phase HPLC (RP-HPLC) column using a gradient of 25% to 58% acetonitrile in water containing 0.1% TFA in 66 min. with a flow rate of 4.8 ml/min. The purity of the peptides was verified by analytical RP-HPLC using a C$_{18}$ column (VYDAC, 4.6 mm×25 cm, 5 IIm) and a linear acetonitrile-water (in presence of 0.1% TFA) gradient of 25% to 58% in 33 min., and by the mass spectral analysis.

Circular Dichroism

CD spectra were recorded on an AVIV 62DS spectropolarimeter as described by Mishra et al. (1994) *J. Biol. Chem.* 269: 7185–7191. Briefly, spectra were obtained using a cell with a 0.1 cm path length and measurements were taken every nm from 260 nm to 190 nm at 25° C. All the CD spectra were signal averaged by adding four scans, base line corrected and smoothed. Peptide solutions in PBS, pH 7.4, were used at a concentration of 11 μM. Peptide-DMPC complexes (1:20 mol:mol) were used to determine the effect of lipid binding on the helicity of these peptides. These complexes were prepared by adding the appropriate volume of peptide solution to DMPC multilamellar vesicles. DMPC multilamellar vesicles were prepared as follows: A known amount of lipid was dissolved in ethanol and the solvent was removed by evaporating slowly under a thin stream of nitrogen. Residual solvent was removed by storing the lipid film under vacuum overnight. An appropriate volume of PBS, pH 7.4 was added to the thin lipid film to give the required final concentration of DMPC. The lipid-peptide complexes were prepared by adding the required volume of peptide solutions to give a lipid to peptide molar ratio of 20:1. Due to the poor solubility of these peptides, a peptide concentration of 11 μM was used. The mean residue ellipticity, $[T]_{MRE}$ (deg. cm$^2$. dmol$^{-1}$) at 222 nm was calculated using the following equation:

$$[T]_{MRE} = MRW[T]/10cl$$

where, MRW is mean residue weight of the peptide, T is the observed ellipticity in degrees, c is the concentration of the peptide in g/ml, and 1 is the path length of the cell in centimeters. The percent helicity of the peptide was estimated from the following equation as described by Morrisett et al. (1973) Biochemistry, 12: 1290–1299:

$$\% \text{ }\Delta\text{helicity} = ([T]_{222} + 3{,}000)/(36{,}000 + 3{,}000)$$

where, $[T]_{222}$ is the mean residue ellipticity at 222 nm.
Differential Scanning Calorimetry.

DSC studies were carried out using a Microcal MC-2 scanning calorimeter (MicroCal, Inc., Amherst, Mass.) at a scan rate of 200° h$^{-1}$ for DMPC, and 37° C. h$^{-1}$ for DiPoPE, using the procedure described by Mishra et al. (1994) J. Biol. Chem. 269: 7185–7191. A known amount of phospholipid was dissolved in chloroform. For one set of samples, peptide was dissolved in methanol and added to a solution of DiPoPE in chloroform/methanol (2:1, v:v). For both, pure lipid samples and the organic solutions of lipid and peptide, solvent was removed under a slow stream of nitrogen. Residual solvent was removed under vacuum. Buffer (PBS, pH 7.4, for DMPC or 20 mM PIPES, 1 mM EDTA, 150 mM NaCl and 0.002% NaN$_3$, pH 7.4, for DiPoPE) alone or a known concentration of peptide solution in buffer to give a specific lipid/peptide molar ratio was added to the dried film and hydrated by vortexing at room temperature for 30 min. For DMPC, four consecutive scans with a 60 min. equilibration time between scans were taken. DSC thermograms were analyzed using the software provided by MicroCal Inc., Amherst, Mass., and Origin, version 5.0.
Surface Pressure Measurements.

Monolayer exclusion pressure measurements give the affinity of the peptides for a lipid-water interface; the procedure of Phillips and Krebs (Phillips and Krebs (1986) Methods Enzymol. 128: 387–403; Ibdah et al. (1989) Biochim. Biophys. Acta 1004: 300–308) was followed. An insoluble monolayer of egg phosphatidylcholine (EPC) was spread at the air-water interface in a Teflon dish at room temperature to give an initial surface pressure ($\Sigma_i$) in the range of 5–45 dyn/cm. A solution of peptides in PBS containing 1.5M Gdn. HCl was carefully injected in to the subphase to give a final concentration of 50 μg/dL. The Gdn. HCl was diluted in the subphase to a final concentration of δ1 mM to allow the peptides to renature. The subphase was stirred continuously and the increase in EPC monolayer surface pressure ($\Delta\Sigma$) was recorded until a steady state value was obtained. The value of the initial surface pressure ($\Sigma_i$) at which the peptides no longer penetrate the EYPC monolayer i.e. the exclusion pressure ($\Sigma_e$), was calculated by extrapolating the $\Sigma_i$ vs $\Delta\Sigma$ linear regression fit to $\Delta\Sigma=0$ dyn/cm.
Right Angle Light Scattering Measurements.

Association of these peptides with egg phosphatidylcholine was determined by following the dissolution of EPC multilamellar vesicles (MLV) by right angle light scattering using a SLM 8000C photon counting spectrofluorometer as described in (Mishra et al. (1994) J. Biol. Chem. 269: 7185–7191). EPC MLVs were prepared by evaporating a solution of EPC (Avanti Polar, AL) under nitrogen and hydrating the lipid film with phosphate-buffered saline (pH 7.4). The sample containing 105 μM EPC and an equimolar amount of peptide was maintained at 25° C. and continuously stirred. Turbidity clarification was monitored for 30 min. Complete dissolution of EPC vesicles was achieved by addition of Triton X-100 to a final concentration of 1 mM.
Lecithin:Cholesterol Acyltransferase (LCAT) Purification.

LCAT was isolated from fresh nonnolipidemic plasma by the method of Albers et al. (1986) Methods Enzymol. 129: 763–783, with some modifications. The density of the plasma was adjusted to 1.21 g/ml and it was centrifuged at 175,000 g for 24 h. The LCAT containing fraction was subjected to Affi-Gel Blue chromatography followed by DE-52-chromatography. LCAT was eluted from the DE-52 column using a 75 to 200 mM NaCl gradient in Tris buffer (10 mM, pH 7.6). SDS-PAGE showed greater than 90% purity of the enzyme with no human apo A-I contamination.
Assay of LCAT Activity:

The substrate was prepared by sonicating egg PC/cholesterol (90:20 mol/mol) containing trace amounts of 7Δ-$^3$H cholesterol in a Branson 250 sonifier for 12 mins to obtain small unilamellar vesicles. The substrate (50μl) was incubated with 5 μg of peptide or human apo A-I and 50μl of BSA (40 μg/ml) for 1 h at 37° C. The total volume was brought up to 150μl. After incubating for 1 h, 100μl of LCAT was added and incubated for 1 h at 37° C. and the reaction was quenched by spotting 10 μl on a silica strip. Cholesterol and cholesteryl ester were separated by thin layer chromatography of the silica strip in hexane:chloroform (2:1 v/v) mixture. Cholesterol and cholesteryl oleate standards were visualized by immersing the TLC plate in a 3% cupric acetate, 8% phosphoric acid buffer and heating it. The positions of the standards were used to cut the strip into two and the two parts were counted in scintillation fluid in a Packard Tri Carb 4530. All reactions were done in triplicate. The activation of LCAT by the peptides is expressed as a percentage of the total activation by apo A-I.
Electrophoresis:

Non-denaturing and SDS-PAGE and was carried out using the method of Laemmli (1970) Nature 227: 680–685. Premade Novex gels were used and the gel was stained with Coomassie blue to identify the protein bands.
LDL-induced Monocyte Chemotactic Activity LDL-induced Monocyte Chemotactic Activity:

Cocultures of human artery wall cells, monocyte isolation, isolation of lipoproteins by ultracentrifugation from the plasma of normal human donors or from mouse plasma by FPLC, and determination of lipid hydroperoxides and monocyte chemotactic activity were performed as as described by Navab et al. (Navab et al. (1991) J. Clin. Invest. 88: 2039–2046; Navab et al. (1977) J. Clin. Invest. 99:

2005–2019). Briefly, LDL and HDL were isolated from human plasma by the method of Havel et al. (Havel et al. (1955) *J. Clin. Invest.* 43:1345–1353). Human aortic endothelial cells (HAEC) and smooth muscle cells (HASMC) were isolated as described by Navab et al. (1991) *J. Clin. Invest.* 88: 2039–2046. Microtitre plates were treated with 0.1% gelatin at 37° C. overnight. HASMC were added at a confluent density of $1\times10^5$ cells/cm$^2$. Cells were cultured for two days, at which time they had covered the entire surface of the well and had produced a substantial amount of extracellular matrix. HAEC were subsequently added at $2\times10^5$ cells/cm$^2$ and were allowed to grow, forming a complete monolayer of confluent HAEC in two days. In all experiments, HAEC and autologous HASMC (from the same donor) were used at passage levels of four to six. Monocytes were isolated blood from normal donors as described by Fogelman et al. (1988) *J. Lipid Res.* 29: 1243–1247. The cocultures were treated with native LDL (250 IIg protein/ml) or presence of HDL (350 IIg protein/ml) or peptides for 8 h. The cocultures were then washed and incubated with medium 199 for an additional 8 h. The resulting coculture supernatants were assayed for monocyte chemotactic activity as described by Navab et al. (1997) *J. Clin Invest*, 99: 2005–2019.

Results.

Analysis of the Peptides.

Table 5 shows the sequences of the various 18A analogues that were synthesized. The peptide Ac-18A-NH$_2$, which has two Phe residues at positions 6 and 18 (close to the interfacial Lys residues) is referred to as 2F. Two 3F peptides were synthesized, 3F$^3$ or 3F$^{14}$, where Leu in position 3 and 14 (both present at the center of the nonpolar face) is replaced by Phe, respectively. Peptide 4F has two Phe residues at the center of the nonpolar face that is a result of substitution of two central Leu residues. The substitutions in the peptides (3F to 7F) are shown in Table 5. With an increase in the number of Phe residues the theoretical hydrophobicity per residue on the nonpolar face increases from 2.05 for the peptide, 2F, to 3.15 for 7F.

TABLE 5

Modifications of Ac-18A-NH$_2$ to increase hydrophobicity

| Peptide | Sequence[1] | Hydrophobicity[2] | Theoretical lipid affinity $(/)^3$ |
|---|---|---|---|
| 2F | Ac-18A-NH$_2$ | 2.05 | 13.03 |
| 3F$^3$ | Ac-[F$^3$18A]-NH$_2$ | 2.20 | 13.84 |
| 3F$^{14}$ | Ac-[F$^{14}$18A]-NH$_2$ | 2.20 | 13.79 |
| 4F | Ac-[F$^{3,14}$18A]-NH$_2$ | 2.35 | 14.59 |
| 5F | Ac-[F$^{11,14,17}$18A]-NH$_2$ | 2.81 | 19.07 |
| 6F | Ac-[F$^{10,11,14,17}$18A]-NH$_2$ | 2.96 | 19.87 |
| 7F | Ac-[F$^{3,10,11,14,17}$18A]-NH$_2$ | 3.15 | 20.78 |

[1]Baseline sequence 18A DWLKAFYDKVAEKLKEAF (SEQ ID NO:1).
[2]Hydrophobicity is expressed as the hydrophobicity per residue on the nonpolar face.
[3]Theoretical lipid affinity has been calculated as shown in (Palgunachari et al. (1996) Arterioscler. Thromb. Vasc. Biol. 16: 328–338).

The peptides were purified on a preparative Vydac C$_4$ column by reversed-phase (RP)-HPLC using water (with 0.1% trifluoroacetic acid) and acetonitrile (0.1% trifluoroacetic acid). The purity and the retention times of the peptides were determined on an analytical Vydac C$_{18}$ column using a gradient of 25%–58% acetonitrile in water containing 0.1% TFA. The purity of these peptides was also confirmed by mass spectrometry. The mass was in agreement with the calculated molecular weight. The retention times of the peptides are listed in Table 6. Although both the 3F peptides and 4F have additional Phe residues compared to 2F, the retention times of these peptides on the C$_{18}$ column are not very different (~22 min). A sudden increase in the retention time is apparent with 5F, 6F and 7F (~26 min). With increasing number of Phe residues, the solubility of these peptides in PBS decreases. As can be seen from Table 6, the solubility of 2F, 3F$^3$, 3F$^{14}$ and 4F (1.25 to 1.4 mg/ml) are significantly higher than those of 5F, 6F and 7F (0.03 to 0.1 mg/ml).

TABLE 6

Physical Properties of the F-peptides.

| Peptide | Molecular Weight[1] | Retention Time (mins)[2] | Solubility (mg/ml)[3] | Monolayer Exclusion Pressure($\Sigma_e$)[4] |
|---|---|---|---|---|
| apo A-I | 28000 | 28.0 | >2.0 | 34 |
| 18A | 2200 | 19.8 | >2.0 | 30 |
| 37pA | 4580 | 26.0 | >2.0 | 41 |
| 2F | 2242 | 22.5 | >2.0 | 38 |
| 3F$^3$ | 2276 | 21.0 | 1.25 | 38 |
| 3F$^{14}$ | 2276 | 21.2 | 1.45 | 39 |
| 4F | 2310 | 22.0 | 1.30 | 40 |
| 5F | 2429 | 26.5 | 0.10 | 45 |
| 6F | 2462 | 27.0 | 0.03 | 46 |
| 7F | 2510 | 26.0 | 0.10 | 45 |

Figures 14A, 14B:
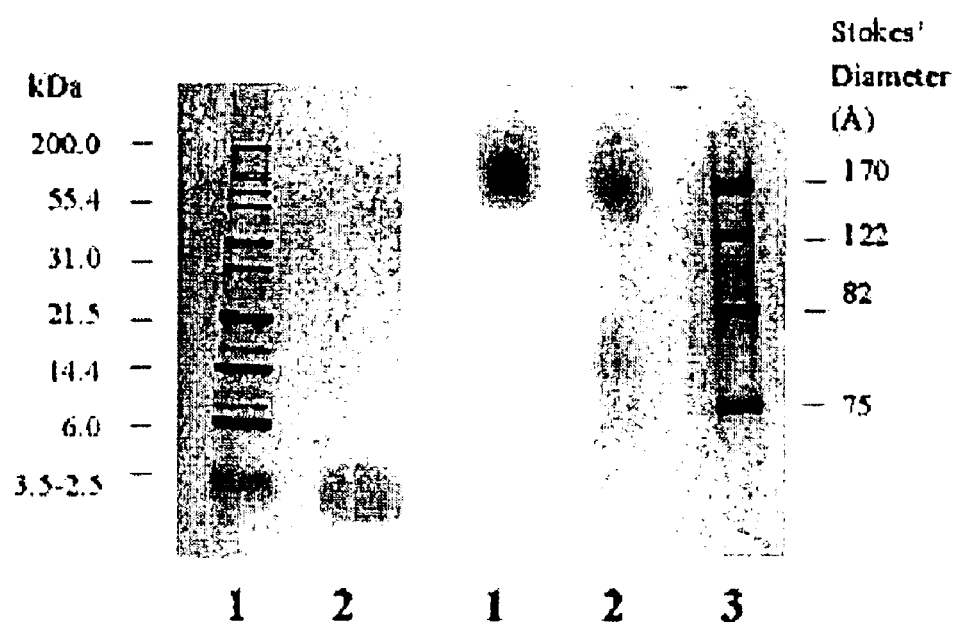
FIGS. 14A and 14B show electrophoresis of 2F indicating its self-association.

[1]The mass as determined by mass spectroscopy was very close to the theoretically calculated molecular weight.
[2]The retention time is the time taken for the peptide to elute from a Vydac C$_{18}$ column using the gradient 25%–58% of acetonitrile in water containing 0.1% TFA in 33 mins.
[3]Solubility was determined in PBS.
[4]Reproducibility of these measurements is $\rho$l dyn/cm The self-association of these amphipathic peptides was examined by non-denaturing polyacrylamide gel electrophoresis (PAGE). FIG. 14 shows the mobility of 2F on both denaturing SDS (FIG. 14A) and on non-denaturing (FIG. 14B) gels. The molecular weight of 2F is 2242 and it can be seen as a single band on the SDS gel (FIG. 14A) moving slightly lower than the lowest molecular weight standard (3.5–2.5 kDa). However, under non-denaturing conditions it forms aggregates in a concentration dependent manner as seen in FIG. 14B. At lower concentrations (100 IIg/ml) it forms aggregates of two sizes while at a higher concentration (250 IIg/ml) only the bigger aggregates are observed (FIG. 14B). All the other peptides studied also exhibited aggregation under non-denaturing conditions suggesting that the peptides possess a strong tendency to self-associate.

Circular Dichroism.

The secondary structure of the peptides was determined by circular dichroism spectroscopy. Table 7 shows the percent helicity of the peptides in PBS and in the presence of DMPC. In PBS, homologues 2F, 4F, 5F, 6F and 7F have a higher percentage helicity than 3F$^3$ and 3F$^{14}$ (Table 7). Since 5F, 6F and 7F were sparingly soluble in PBS, the CD studies were carried out using 11 IIM of the peptides (a concentration at which they were all soluble). Peptide 2F showed 55% helicity, comparable to 5F in solution. Both 6F and 7F were slightly more helical (67% and 58% respectively) while 4F was slightly less (45%). Both the 3F peptides were much less (| 20%) helical. However, binding to DMPC considerably increased the helicity of all the peptides except for 6F (Table 7). In a lipid environment, 2F, 5F and 7F showed a high helical content (68% to 76%). Although, the peptides 3F$^3$ and 3F$^{14}$ had a very small helical content in PBS, there was a significant increase in helicity in a lipid environment, from about 22% to 42% for 3F$^3$, and from 19% to 55% for 3F$^{14}$. The helicity of the peptides 6F and 4F did not change appreciably in the presence of lipid. However, these peptides were still less helical than peptides 2F and 5F. The CD results suggest that there is no systematic change in the helicities of the peptides with increasing substitution by Phe; peptides 2F and 5F exhibited maximum helicity in solution and in the presence of phospholipid.

TABLE 7

Helicities of the F-peptides in aqueous and lipid environments

| Peptides | Percent Helicity | |
|---|---|---|
| | PBS[1] | DMPC[1] |
| 2F | 55 | 72 |
| 3F[3] | 22 | 42 |
| 3F[14] | 19 | 55 |
| 4F | 45 | 44 |
| 5F | 55 | 76 |
| 6F | 67 | 50 |
| 7F | 58 | 68 |

[1]11 IIM solutions of peptide was used. Peptide:DMPC ratio used was 1:20 (mol/mol). Three measurements were made and an error of ρ 10% was obtained.

DSC Studies with DMPC and DiPoPE.

The effect of these 18A analogues on the chain melting transition of multilamellar vesicles of DMPC was studied by DSC using peptide-lipid mixtures at 100:1 lipid/peptide molar ratio. Table 8 shows the transition temperatures and enthalpies of the chain melting transition of DMPC in the presence and absence of peptides. The pure lipid undergoes a pretransition at 13θ C. and a main chain melting transition at 23θ C. The addition of the peptides to DMPC resulted in a broadening of the gel to liquid-crystalline transition and a lowering of the transition enthalpy (Table 8). The pretransition was not seen in the presence of any of the peptides. Among the peptides studied, 2F, 3F[3], 5F, and 6F reduced the transition enthalpy to the maximum extent (Table 8). None of the peptides changed the transition temperature by more than 0.2θ C.

TABLE 8

Effect of the F-peptides on the chain melting transition parameters of DMPC

| Peptide | $T_{CM}$ (θC) | $\ni H_{CM}$ (kcals/mol) | $\ni_{T1/2}$ (θC) |
|---|---|---|---|
| DMPC | 23.1 | 6.4 | 0.2 |
| 2F | 23.2 | 4.5 | 0.5 |
| 3F[3] | 23.2 | 4.9 | 0.4 |
| 3F[14] | 23.2 | 5.5 | 0.3 |
| 4F | 23.2 | 5.3 | 0.4 |
| 5F | 23.2 | 4.9 | 0.5 |
| 6F | 23.1 | 4.0 | 0.5 |
| 7F | 23.2 | 4.5 | 0.5 |

The DMPC/peptide ratio used was 100:1 (mol/mol). The concentration of the DMPC used was 1.5 mM. $T_{CM}$ is the temperature at which the chain melting transition takes place, $\ni H_{CM}$ is the enthalpy of the transition and $\ni_{T1/2}$ is the width at half maximum of the transition.

Figure 15:
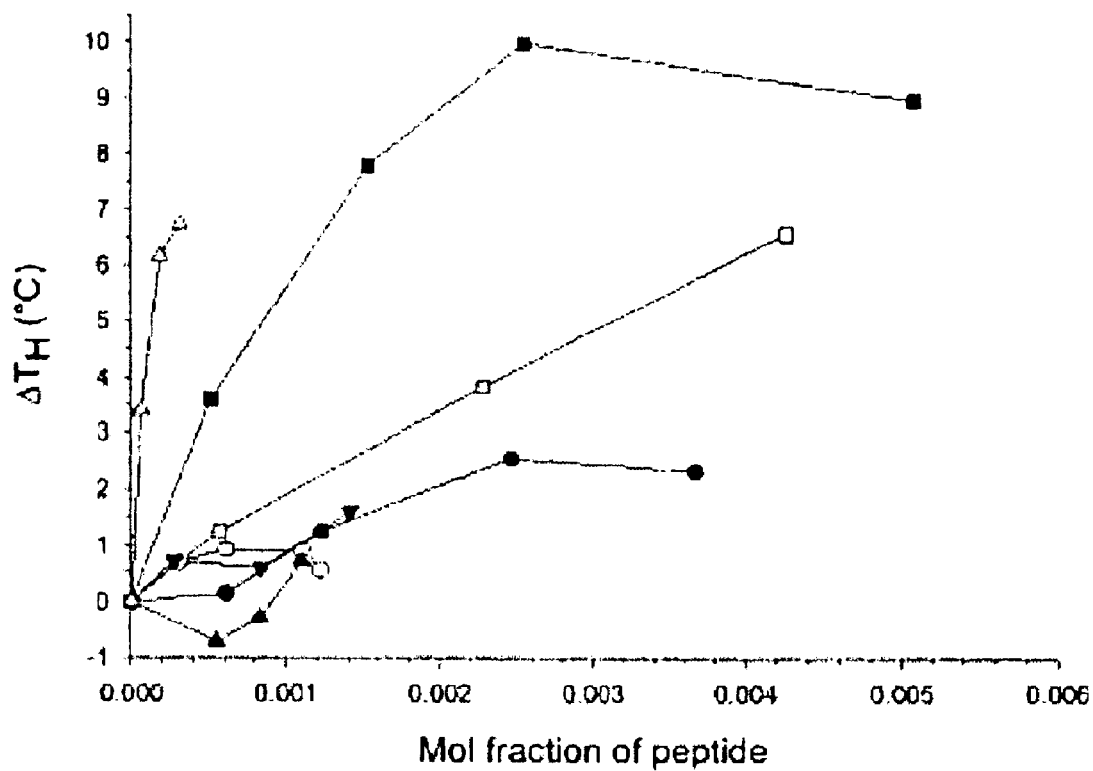
FIG. 15 shows that the homologous series of peptides stabilize the hex-phase transition of DiPoPE bilayers. Shift in $T_H$ of DiPoPE as a function of the mole fraction of added peptide. Measured by DSC at a heating scan rate of 37°/h. ● 2F; ○ 3F$^3$; ■ 4F; □ 5F;; ▼ 6F; ▲ 7F; Δ apo A-I.

The shift in the bilayer to hexagonal phase transition temperature ($T_H$) has been used to evaluate the effects of peptides on the intrinsic curvature properties of phospholipids (Epand (1998) *Biochim. Biophys. Acta*, 1376: 353–368). It was previously shown that 2F raises $T_H$ of DiPoPE (Tytler et al. (1993) *J. Biol. Chem.* 268: 22112–22118). In the current study we prepared the peptide-lipid mixtures in two ways. One was by adding the peptide in organic solvent to the lipid in organic solvent followed by depositing the material as a film and subsequently hydrating with buffer. In the other method, the peptide and lipid were mixed after each was hydrated separately. If the mixture comes to equilibrium prior to the DSC analysis, it should not matter how the peptide and lipid are originally mixed. However, membrane systems can equilibrate slowly, in which case there may be more peptide in the lipid when it was incorporated at high concentrations into the lipid film. In general the results from both methods of sample preparation are similar (not shown) but the shift in $T_H$ tends to be larger for samples in which peptide was incorporated into a film composed of lipid and peptide. The variation of the $T_H$ with mol fraction of peptide is shown for the various peptides and apo A-I (FIG. 15). A linear increase in $T_H$ is observed for 2F and 5F while 4F behaves more like apo A-I in that a more rapid increase is observed at lower peptide concentrations. On the other hand, the two 3F analogues as well as 6F and 7F do not significantly affect $T_H$.

Interaction of Peptides with Phospholipid Monolayers.

The monolayer exclusion pressure, $\Sigma_e$, is the surface pressure at which peptides are no longer able to penetrate a monolayer of EPC. The value of $\Sigma_e$, reflects the theoretical lipid affinity of the peptide. The exclusion pressure of the F peptides increased with increasing number of Phe residues (Table 6). All the peptides studied here had higher exclusion pressures than apo A-I and the parent peptide 18A. The value of $\Sigma_e$ increased gradually from 2F to 4F (38 to 40 dyn/cm). This is in the range seen for 37pA, a tandem repeat of 18A punctuated by a proline. The exclusion pressure value increases significantly for 5F, 6F and 7F (40 to 45 dyn/cm). It is apparent that the 5F, 6F and 7F homologues possess a similar ability to interact with EPC monolayers, as determined by the exclusion pressure. It is interesting that the HPLC retention times and monolayer exclusion pressures for the F-peptides listed in Table 6 show parallel trends, with an abrupt increase between 4F and 5F.

Right Angle Light Scattering.

Figure 16:
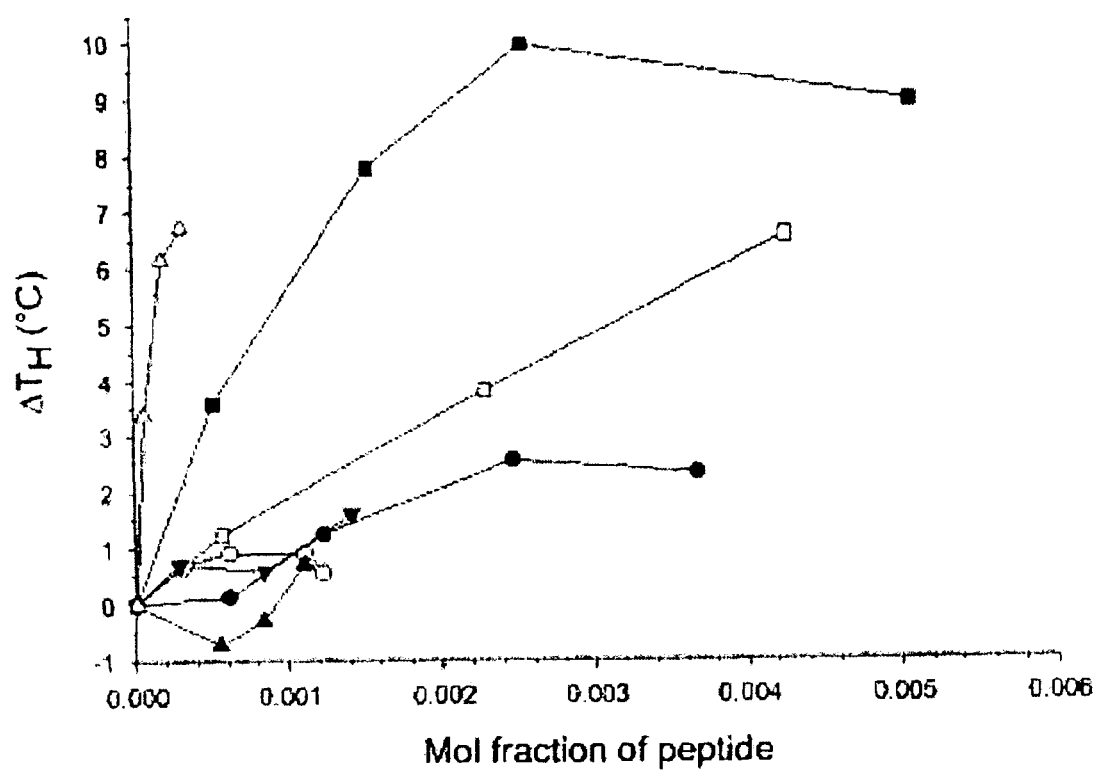
FIG. 16: Relative right angle light scattering monitoring of the dissolution of EPC MLVs by homologous series of peptides as a function of time. A representative EPC MLV clarification curve is shown for each of the homologous peptides. An equimolar concentration of peptide and EPC was used (105 ΠM). Both excitation and emission wavelengths were 400 nm. Triton X-100 achieved complete dissolution at a final concentration of 1 mM. -●-EPC;-○-2F;-■-3F$^3$;-□-3F$^{14}$;-▲-4F;-э-5F;-▼-6F; -□-7F;-◇-human apo A-I; -◆-Triton X-100.

As can be seen in FIG. 16, all the peptides were able to clarify EPC MLVs, unlike apo A-I, which does not clarify EPC MLVs. The two homologous 3F peptides were the least effective in clarifying the EPC MLVs. The homologous peptides 2F, 5F, 6F and 7F, all clarified the EPC MLVs to a similar extents. Peptide 4F was the most effective in clarifying EPC MLVs with activity similar to that of Triton X-100. The time for 50% clearance of the turbidity of EPC MLVs was also the shortest for the homologue 4F. Peptide 7F took the longest time to achieve 50% clearance; this was due to an initial lag period of α300 secs (FIG. 16). This is probably due to the requirement for self-associated 7F molecules to dissociate before they can interact with EPC MLVs and solubilize them. The slower rates of clearance exhibited by the homologues 2F, 5F and 6F may also be due to a higher self-association of these peptides.

Activation of the Plasma Enzyme LCAT.

Figure 17:
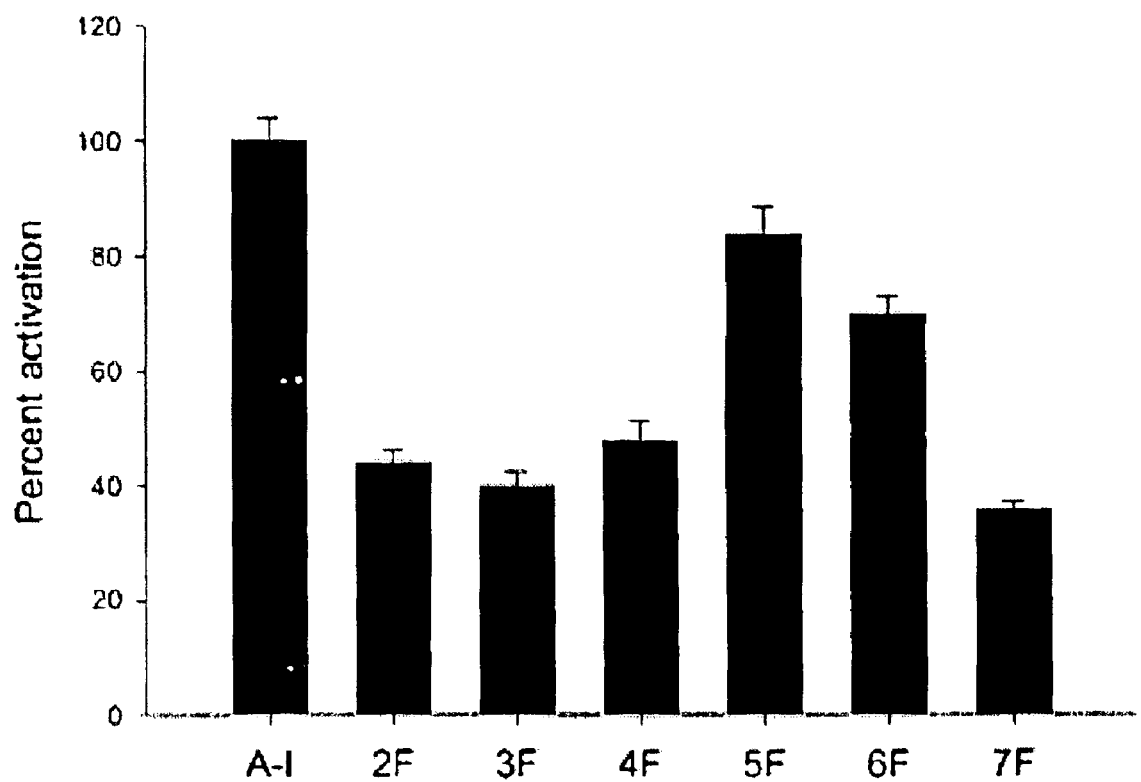
FIG. 17 illustrates LCAT activating ability of homologous peptides. Histograms representing activation of LCAT by the F-peptides. LCAT activity was measured using small unilamellar vesicles of EPC-cholesterol and the activity is represented as a percentage compared to that of apo A-I activity, where apo A-I activity is taken to be 100%. Each value represents an average value from triplicates. The peptide concentration used was 20 Πg/ml.

The ability of these peptides to activate the plasma enzyme LCAT was determined by measuring the initial velocity of the LCAT reaction with egg PC-cholesterol vesicles as substrate (FIG. 17). LCAT activation is expressed relative to that by apo A-I, which was considered to be 100%. Activation of LCAT by 20 IIg/ml of peptides and apo A-I is shown in FIG. 4. At this concentration, apo A-I activates LCAT better than any of the peptides. Among the peptides studied here, however, 5F is the best activator (80% of apo A-I). As far as LCAT activation is concerned, both 3F[3] and 3F[14] have similar activating abilities. Therefore, they have been represented as one bar (FIG. 17).

LDL-induced Monocyte Chemotactic Activity.

Figure 18:
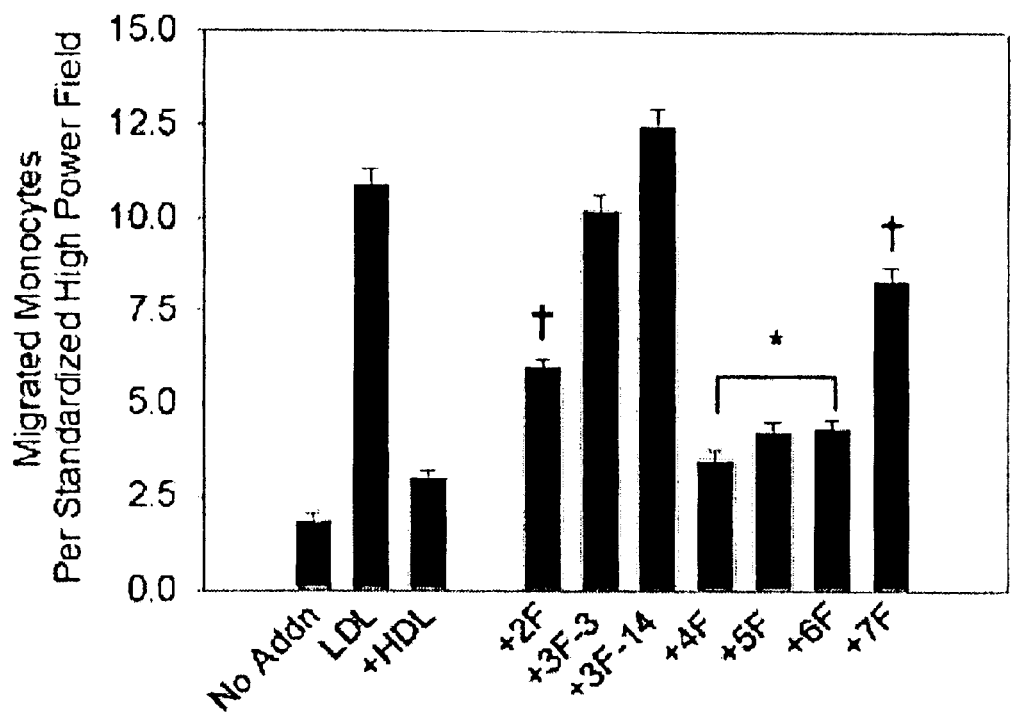
FIG. 18 shows that LDL-induced monocyte chemotaxis was inhibited by the homologous series of peptides. LDL alone or LDL incubated with either human HDL or the homologous series of peptides was added to the human artery wall cell cocultures for 8 h in the presence of 10% LPDS. The supernatants were removed and the cocultures were washed with culture medium without serum or LPDS. The conditioned medium was then collected and analyzed for monocyte chemotactic activity. The data represent mean±SEM values (n=9 in each case). By pair-wise comparisons with LDL all peptides except the 3F peptides were significantly more effective (at least p<0.001, signified by '†' and *). Comparisons between all peptides were analyzed by one-way ANOVA. The asterisk indicates that peptides 4F, 5F and 6F were significantly more effective than the homologues 2F and 7F (p<0.05 by Duckett comparison). The bracket indicates no significant difference in the ability to inhibit LDL-induced chemotaxis among these three peptides.

When LDL is incubated with the human artery wall coculture system, it is trapped in the subendothelial space and gets oxidized to produce biologically active lipids. These lipids induce monocyte chemotaxis. Thus, coculture monocyte chemotaxis is a well-established assay for the formation of biologically active lipids. It has been shown that inhibition of chemotaxis is directly correlated with the removal of "seeding molecules" that are responsible for the secretion of monocyte chemotactic protein-1 (MCP-1) (Navab et al. (2000) *J. Lipid Res.* 41: 1481–1494; Navab et al. (2000) *J. Lipid Res.* 41: 1495–1508)and differentiation factor macrophage colony-stimulating factor (M-CSF). FIG. 18 shows that LDL after incubation with peptides exhibited varied effects with homologues 4F, 5F and 6F reducing the chemotactic properties of LDL the most. Peptides 3F were not at all effective compared to 2F and 7F, which were less effective than the peptides 4F, 5F and 6F.

Discussion.

Effect of Increasing Hydrophobicity of a Class A Amphipathic Helical Peptide Analogue on its Physical-chemical and Lipid Binding Properties:

The peptides studied in this paper are homologues of the parent peptide, 18A. The calculated hydrophobicity per residue (according to modified GES scale (Palgunachari et al (1996) *Arterioscler. Thromb. Vasc. Biol.* 16: 328–338)) on the nonpolar face increased as the number of Phe residues increased. This increase in hydrophobicity (Table 5) is reflected in the theoretical lipid affinity, / (Ibid.). However, the / value increases gradually from 2F to 4F (from 13.03 to 14.59) with a sudden increase in the value from 14. 59 (for 4F) to 19.07 for 5F. A gradual increase in / was again observed after 5F in the values for 6F and 7F (Table 5). This is due to the substitution of Leu at positions 3 and 14 in Ac-18A-NH$_2$ with Phe which results in a slight increase in the hydrophobicity of the nonpolar face and thus, a slight increase in / values for the two 3F analogues and 4F. In homologues 5F, 6F and 7F however, besides the Leu to Phe substitutions, Ala in positions 11 and 17 are also substituted by Phe, resulting in a significant increase in the / values (Table 5). Since Ala is less hydrophobic than Leu and Leu is less hydrophobic than Phe, the substitution of Ala to Phe causes a greater change in hydrophobicity and theoretical lipid affinity of the resulting peptide than a Leu to Phe substitution.

The retention time on a $C_{18}$ reversed phase HPLC column, solubility of these peptides and their ability to penetrate an EPC monolayer, all exhibit a trend similar to that seen in the theoretical lipid affinity values (Table 6). The retention times of peptides 2F, 3F$^3$, 3F$^{14}$ and 4F are about the same (21–22 min.) and significantly less than those of 5F, 6F and 7F, which comprise a second group (26–27 min.). The peptides 2F to 4F have considerably higher aqueous solubility than homologues 5F to 7F, which are sparingly soluble (Table 6). A gradual increase in exclusion pressure was observed from 2F to 4F after which there is an abrupt increase from 40 dyn/cm to 45 dyn/cm. The exclusion pressures for the peptides 5F, 6F and 7F are not very different from each other and are significantly higher than that of apo A-I (Table 6). The parent peptide 18A (30 dyn/cm) and even the dimer of 18A, 37pA (40 dyn/cm) were also significantly less effective in penetrating into an egg PC monolayer spread at the air-water interface. Based on the above physical properties, the F peptides can be separated into two groups; group I with 2F, 3F$^3$, 3F$^{14}$, 4F and group II with peptides 5F, 6F and 7F.

The CD data (Table 7) indicate that the percent helicity value of all the peptides increases in the presence of DMPC suggesting that all of the peptides associate with lipids. The binding of these peptides to DMPC appears to be similar as suggested by DSC (Table 8). However, the effect of these peptides on the stabilization of the bilayer structure of DiPoPE is different. 4F and 5F seem to interact better with DiPoPE because they appear to be better stabilizers than the other peptides.

While apo A-I is not able to clarify EPC MLVs, all of the peptide analogs are able to do so, but to different extents. Among the group I peptides that are easily soluble in aqueous buffer and exhibit a monolayer exclusion pressure value in the range 38–40 dyn/cm (2F, 3F analogs and 4F), 4F appears to be the most efficient and at the peptide:lipid ratio under investigation, exhibits similar kinetics to that of Triton X-100 (FIG. 16). While the monolayer exclusion pressures of the peptides 2F and 3F are similar, the 3F homologues are the slowest in clarifying EPC MLVs. The reason for reduced EPC clarifying ability of the 3F homologues is not clear at this time. The group II peptides (5F, 6F and 7F) that are not easily soluble in aqueous buffer and possess surface pressure values 45dyn/cm solubilize EPC MLVs relatively slowly. These results are consistent with peptide aggregates having to disassociate and then interact with EPC. The superior reactivity of 4F can be explained by the fact that its hydrophobicity is optimal so that hydrophobic peptide:peptide interactions favoring self-association do not prevent peptide:lipid interactions.

Effect of Increased Hydrophobicity on LCAT Activation:

Activation of LCAT is a complex process and is not only dependent on lipid affinity but also on the interaction of the amphipathic helical protein with the enzyme LCAT (Jonas (2000) *Biochim. Biophys. Acta* 1529: 245–256). In agreement with this, the ability to activate LCAT was found to be different for the homologous peptides. The peptide 5F showed the maximum LCAT-activating ability, in agreement with the physical properties studied in Table 6 wherein an abrupt increase was seen from 4F to 5F, including exclusion pressure values at the egg PC-water interface. The fact that the peptides 6F and 7F are not as effective as 5F could be explained by the increased peptide:peptide interaction (as reflected in the low aqueous solubility of these peptides) which does not allow for peptide:lipid or peptide:LCAT interaction. These results are in agreement with our earlier observations with the 18A dimer peptides in which the enhanced self-association of the dimer 18A-18A (36A) peptide reduced its ability to interact with lipids compared to 18A-Pro-18A peptide (Jonas (2000) *Biochim. Biophys. Acta* 1529: 245–256). Although LCAT activation by the peptides has been compared with that of apo A-I, it should be noted that apo A-I and the peptides interact differently with the substrate since they all have different reactivities to EPC (FIG. 16). Similar observations were made by Chung et al who showed that a synthetic peptide 18A-Pro-18A and apo A-I interact differently with EPC (Chung et al. (1985) *J. Biol. Chem.* 260: 10256–10262).

Effect of Increased Hydrophobicity of the Nonpolar Face on LDL-induced Monocyte Chemotaxis:

Since removal of "seeding molecules" depends on the amphipathicity of the peptide as reported by us (Navab et al. (2000) *J. Lipid Res.* 41: 1481–1494; Navab et al. (2000) *J. Lipid Res.* 41: 1495–1508), we examined the ability of these peptides to inhibit LDL-induced monocyte chemotaxis. In this assay, peptides 4F, 5F and 6F at 100 IIg/ml level, showed significant and similar inhibition of LDL-induced chemotaxis based on one way analysis of variance. Although the homologue 2F showed some inhibitory activity, for reasons that are not clear, peptide analogs 3F showed no inhibition compared to LDL alone. These results were in agreement with the fact that the peptide 3F was not able to remove the lipid hydroperoxides (results not shown) and the reduced ability to clarify EPC MLVs. Peptide 7F was significantly less effective than peptides 4F, 5F and 6F ($P<0.001$). The reduced ability of 7F can again be explained by increased self-association of the peptide that decreased its ability to interact with the lipid as seen in EPC MLV clarification studies. These results again demonstrate that the delicate balance existing between the contributions of the hydrophobicity of the peptide to self association can critically affect apo A-I-mimicking properties.

In vivo administration of peptide 5F, which possesses increased LCAT-activating ability and increased ability to remove "seeding molecules" protected mice from diet-induced atherosclerosis. In contrast, administration of 2F, that is similar in LCAT-activating ability to 4F, but less effective than 4F and 5F in removing "seeding molecules" from LDL, did not significantly inhibit diet-induced lesion formation in C57 BL6 mice (mean lesion area for control mice administered with PBS $14.7\pm1.8$ $\Pi m^2 \times 10^{-3}$ compared to 2F-administered mice $13.2\pm1.7$ $\Pi m^2 10^{-3}$, n=15). It follows that in this mouse model, inhibition of LDL-induced monocyte chemotaxis is more anti-atherogenic than LCAT activation. Since the peptides 2F and 4F are similar in activating LCAT, and 4F and 5F are similar in removing "seeding molecules" from LDL, the peptide 4F may serve as a reagent to distinguish between the importance of LCAT activation and the inhibition of LDL-induced monocyte chemotaxis in different atherosclerosis-sensitive mouse models. If the inhibition of LDL-induced chemotaxis is more important than the LCAT-activating ability, then 4F should be better peptide to use as an inhibitor of atherosclerosis since this peptide is more soluble than the peptides 5F, 6F and 7F.

Example 4

Peptides D-4F Maintains Paroxynase Levels and Blocks Oxidized Phospholipid Production During an Acute Inflammatory Response We have observed that intranasal instillation of the influenza A virus in mice caused a time dependent loss in the anti-inflammatory properties of HDL reaches a maximum 7 to 9 days after inoculation. The dose chosen was one that did not cause viremia and so the changes were not due directly to the virus but were due to the inflammatory state induced by the host's systemic response to the viral infection. This response is part of the innate immune system and is known as the acute phase reaction or acute phase response.

One of the consequences was diminution in paraoxonase and platelet activating acetylhydrolase activity in the HDL of the mice after the influenza infection. As a result of the loss of these HDL enzymatic activities and also as a result of the association of pro-oxidant proteins with HDL during the acute phase response, HDL was no longer able to prevent LDL oxidation and was no longer able to prevent the LDL-induced production of monocyte chemotactic activity by endothelial cells. Normal HDL is able to prevent the LDL-induced production of monocyte chemotactic activity by endothelial cells because normal HDL contains sufficient paraoxonase and platelet activating acetylhydrolase activities to destroy the biologically active oxidized phospholipids.

Figure 19:
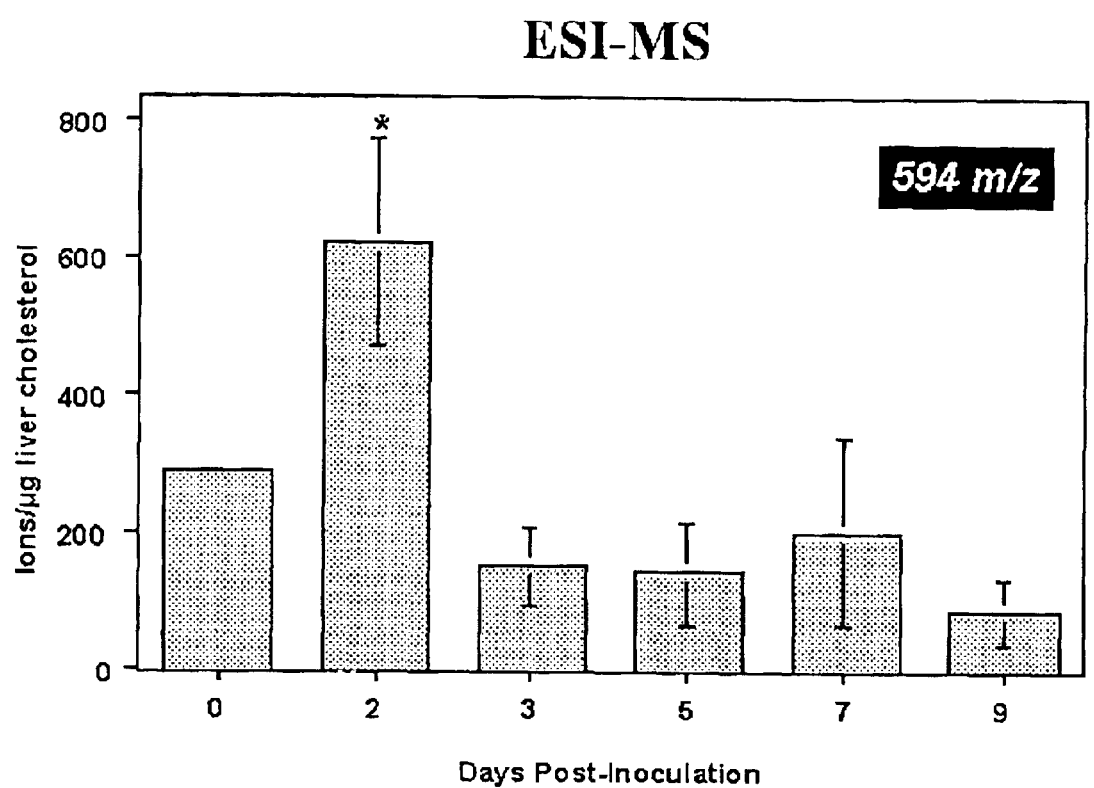
FIG. 19 shows that Influenza A infection causes an increase in hepatic oxidized phospholipids two days after infection. C57BL/6 mice on a chow diet were infected with a dose of influenza A virus intranasally such that no viremia resulted as described by Van Lenten et al. (2001) *Circulation*, 103: 2283–2288. Zero, 2, 3, 5, 7, and 9 days after infection the livers were removed and oxidized phospholipid content determined by ESI-MS.
Figure 20:
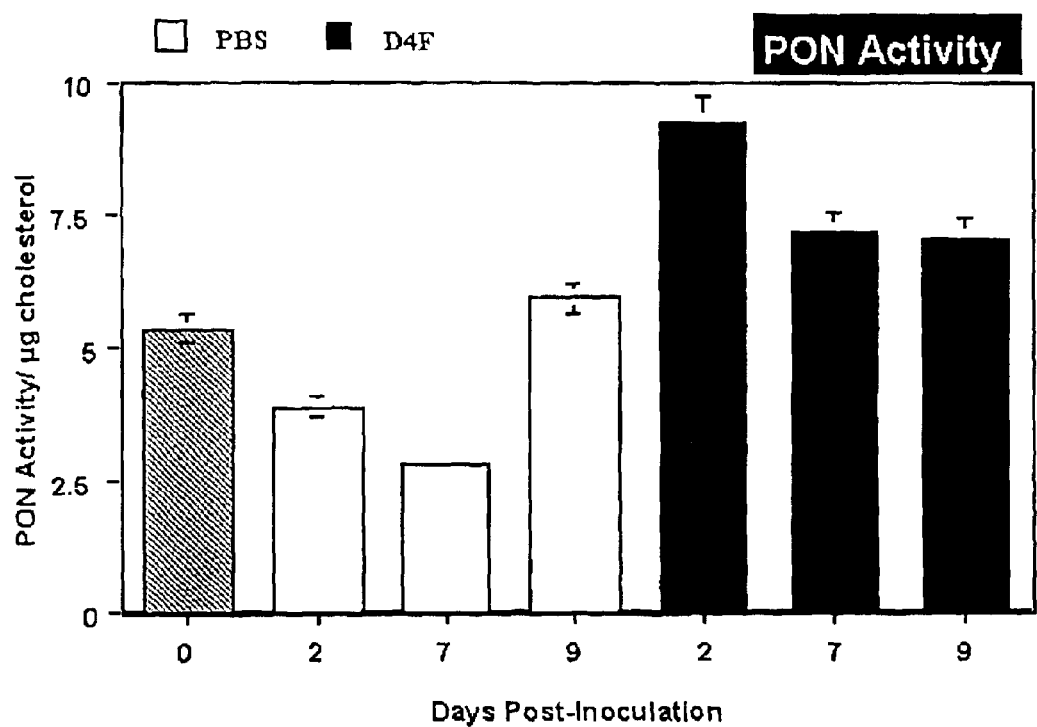
FIG. 20 shows that D-4F prevents the decrease in paraoxonase activity after Influenza A infection. Some of the mice described in FIG. 19 were injected intraperitoneally with 20 Πg daily of D-4F and the others were injected with phosphate buffered saline (PBS). Paraoxonase activity (PON) was measured in the plasma at zero, 2, 7, and 9 days after infection.
Figure 21:
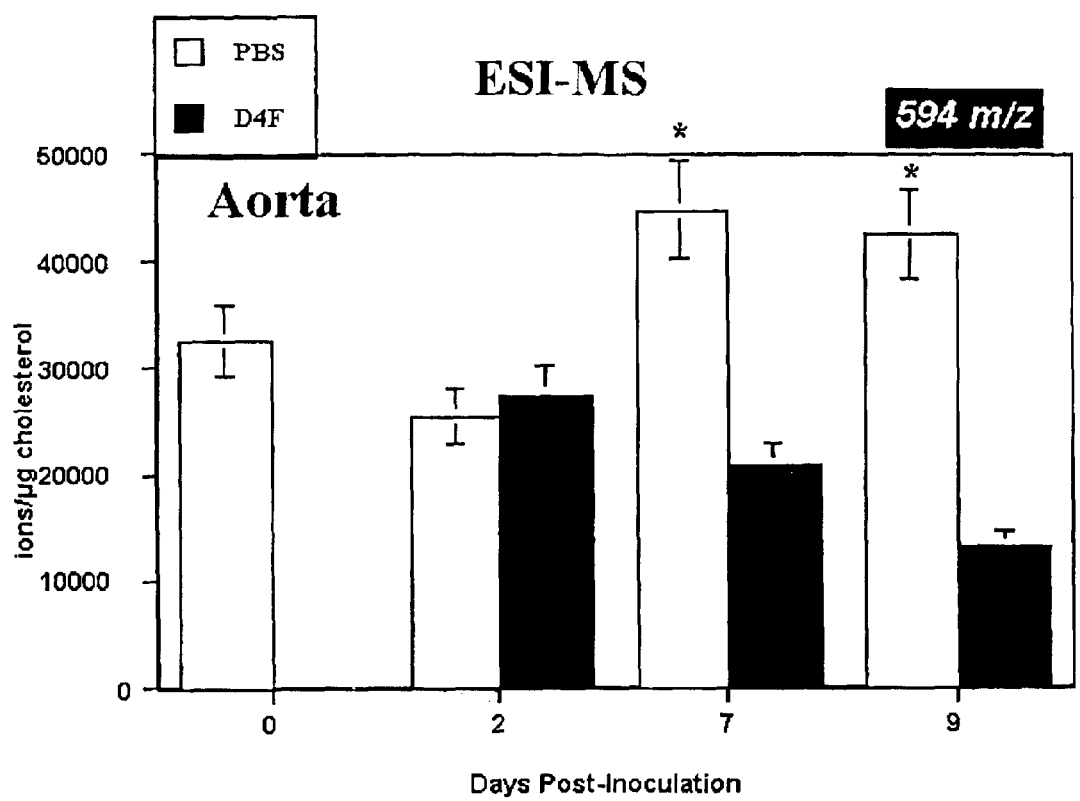
FIG. 21 shows that D-4F prevents the induction of oxidized phospholipids in aortas of mice infected with Influenza A virus. Some of the mice described in FIG. 19 were injected intraperitoneally with 20 Πg daily of D-4F and the others were injected with phosphate buffered saline (PBS). The aortas of the mice were harvested at days zero, 2, 7 and 9 days after infection and oxidized phospholipid content was determined by ESI-MS.

In this example, we demonstrate that early (two days) after influenza A infection the livers of infected mice generated these oxidized phospholipids (FIG. 19) and later (7 to 9 days after infection) these biologically active oxidized phospholipids appeared in the aorta of the mice. However, if the mice were injected with 20 micrograms of D-4F daily after infection with the influenza A virus paraoxonase levels did not fall (FIG. 20) and the biologically active oxidized phospholipids were not generated beyond background (FIG. 21).

These data indicate that D-4F (and/or other peptides of this invention) can be given either orally or by injection to patients with known coronary artery disease during influenza infection or other events that can generate an acute phase inflammatory response (e.g. due to viral infection, bacterial infection, trauma, transplant, various autoimmune conditions, etc.) and thus we can prevent by this short term treatment the increased incidence of heart attack and stroke associated with pathologies that generate such inflammatory states.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A peptide that ameliorates a symptom of atherosclerosis, wherein said peptide:
   ranges in length up to 30 amino acids;
   comprises at least one class A amphipathic helix;
   protects a phospholipid against oxidation by an oxidizing agent;
   comprises the amino acid sequence-D-W-F-K-A-F-Y-D-K-V-A-E-K-F-K-E-A-F(SEQ-ID-NO:5); and
   bears at least one protecting group.

2. The peptide of claim 1, wherein said protecting group is a protecting group selected from the group consisting of amide, 3 to 20 carbon alkyl groups, Fmoc, 9-fluoreneacetyl group, 1-fluorenecarboxylic group, 9-fluorenecarboxylic group, 9-fluorenone-1-carboxylic group, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimethyl-2,6-dioxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), Benzyloxymethyl (Bom), t-butoxycarbonyl (Boc), cyclohexyloxy (cHxO),t-butoxymethyl (Bum), t-butoxy (tBuO), t-Butyl (tBu), Acetyl (Ac), a carbobenzoxy group, a propyl group, a butyl group, a pentyl group, a hexyl group, and Trifluoroacetyl (TFA).

3. The peptide of claim 2, wherein said peptide comprises a first protecting group coupled to the amino terminus and a second protecting group coupled to the carboxyl terminus.

4. The peptide of claim 1, wherein said peptide is mixed with a pharmacologically acceptable excipient.

5. The peptide of claim 1, wherein said peptide is mixed with a pharmacologically acceptable excipient suitable for oral administration to a mammal.

6. The peptide of claim 1, wherein said peptide comprises a protecting group coupled to the amino terminus and said amino terminal protecting group is a protecting group selected from the group consisting of a benzoyl group, an acetyl, a propionyl, a carbobenzoxy, a propyl, a butyl, a pentyl, a hexyl, and a 3 to 20 carbon alkyl.

7. The peptide of claim 1, wherein said peptide comprises a protecting group coupled to the carboxyl terminus and said carboxyl terminal protecting group is an amide.

8. The peptide of claim 1, wherein said peptide comprises a first protecting group coupled to the amino terminus and a second protecting group coupled to the carboxyl terminus.

9. The peptide of claim 1, wherein said peptide comprises:
   a first protecting group coupled to the amino terminus wherein said protecting group is a protecting group selected from the group consisting of a benzoyl group, an acetyl, a propionyl, a carbobenzoxy, a propyl, a butyl, a pentyl, a hexyl, and a 3 to 20 carbon alkyl; and
   a second protecting group coupled to the carboxyl terminus and said carboxyl terminal protecting group is an amide.

10. The peptide of claim 1, wherein said oxidizing agent is selected from the group consisting of hydrogen peroxide, 13(S)-HPODE, 15(S)-HPETE, HPODE, HPETE, HODE, and HETE.

11. The peptide of claim 1, wherein said phospholipid is selected from the group consisting of 1-palmitoyl-2-arachidonoyl-sn-glycero-3-phosphorylcholine (PAPC), 1-stearoyl-2-arachidonoyl-sn-glycero-3-phosphorylcholine (SAPC)), and 1-stearoyl-2-arachidonyl-sn-glycero-3-phosphorylethanolamine (SAPE).

12. A method of mitigating or preventing a coronary complication associated with an acute phase response to an inflammation in a mammal, wherein said coronary complication is a symptom of atherosclerosis, said method comprising administering to a mammal having said acute phase response, or at risk for said acute phase response, a peptide of any one of claims 2, 3, 4, 5, 1, 6, 7, 8, 9, 10 and 11.

13. The method of claim 12, where said administration is by a route selected from the group consisting of oral administration, nasal administration, rectal administration, intraperitoneal injection, intravascular injection, subcutaneous injection, transcutaneous administration, and intramuscular injection.

14. The method of claim 12, wherein said peptide is provided as a unit formulation in a pharmaceutically acceptable excipient.

15. The method of claim 12, wherein said acute phase response is an inflammatory response associated with a recurrent inflammatory disease.

16. The method of claim 13, wherein said acute phase response is associated with a disease selected from the group consisting of leprosy, tuberculosis, systemic lupus erythematosus, polymyalgia rheumatica, polyarteritis nodosa, scleroderma, idiopathic pulmonary fibrosis, chronic obstructive pulmonary disease, coronary calcification, calcific aortic stenosis, osteoporosis, and rheumatoid arthritis.

17. The method of claim 12, wherein said acute phase response is an inflammatory response associated with a condition selected from the group consisting of a bacterial infection, a viral infection, a fungal infection, an organ transplant, a wound, an implanted prosthesis, parasitic infection, sepsis, endotoxic shock syndrome, and biofilm formation.

18. A method of mitigating or preventing a coronary complication associated with an acute phase response to an inflammation in a mammal, wherein said coronary complication is a symptom of atherosclerosis, said method comprising:
   assaying said mammal for an acute phase protein (APP) level indicative of an acute phase response or a significant risk of an acute phase response; and
   administering to a mammal showing an acute phase protein (APP) level indicative of an acute phase response a peptide of any one of claims 2, 3, 4, 5, 1, 6, 7, 8, 9, 10 and 11.

19. The method of claim 18, wherein said acute phase protein (APP) is a positive APR selected from the group consisting of serum amyloid A, c-reactive protein, serum amyloid P component, C2 complement protein, C3 complement protein, C4 complement protein, C5 complement protein, C9 complement protein, B complement protein, C1 inhibitor, C4 binding protein, fibrinogen, von Willebrand factor, α1-antitrypsin, α1-antichymotrypsin, α2 antiplasmin, heparin cofactor II, plasminogen activator inhibitor I, haptoglobin, haemopexin, ceruloplasmin, manganese superoxide dismutase, α1-acid glycoprotein, haeme oxygenase, mannose binding protein, leukocyte protein I, lipoprotein (a), and lipopolysaccharide binding protein.

20. The method of claim 18, wherein said acute phase protein (APP) is a negative APR selected from the group consisting of albumin, prealbumin, transferin, apoAI, apoAII, α2-HS glycoprotein, inter-α-trypsin inhibitor, and histidine-rich glycoprotein.

21. The peptide of claim 1, wherein said peptide has the formula:

P¹-D-W-F-K-A-F-Y-D-K-V-A-E-K-F-E-A-F-P² (SEQ ID NO:5)

wherein P¹ and P² are protecting groups.

22. The peptide of claim 21, wherein:
P¹ is selected from the group consisting of a benzoyl group, an acetyl, a propionyl, a carbobenzoxy, a propyl, a butyl, a pentyl, a hexyl, and a 3 to 20 carbon alkyl; and
P² is an amide.

23. The peptide of claim 22, wherein P¹ is an acetyl and P² is an amide.

24. The peptide of claim 22, wherein said peptide is mixed with a pharmacologically acceptable excipient.

25. The peptide of claim 22, wherein said peptide is mixed with a pharmacologically acceptable excipient for oral administration.

26. A method of ameliorating a symptom of atherosclerosis in a mammal, said method comprising administering to said mammal a peptide or a concatamer of a peptide that:
ranges in length up to about 30 amino acids;
comprises at least one class A amphipathic helix;
protects a phospholid against oxidation by an oxidizing agent; and
comprises the amino acid sequence D-W-F-K-A-F-Y-D-K-V-A-E-K-E-A-F (SEQ-ID-NO:5).

27. The method of claim 26, wherein said administering comprises orally administering said peptide.

28. The method of claim 26, wherein said mammal is a mammal diagnosed as having one or more symptoms of atherosclerosis.

29. The method of claim 26, wherein said mammal is a mammal diagnosed as at risk for atherosclerosis.

30. The method of claim 26, wherein said mammal is a human.

31. The method of claim 26, wherein said mammal is non-human mammal.

32. The method of claim 26, wherein said peptide is combined with a pharmacological excipient.

33. The method of claim 26, wherein said peptide is combined with a pharmacological excipient suitable for oral administration to a mammal.

34. The method of claim 26, wherein said peptide further comprises a protecting group coupled to the amino or carboxyl terminus.

35. The method of claim 34, wherein said protecting group is a protecting group selected from the group consisting of amide, 3 to 20 carbon alkyl groups, Fmoc, 9-fluoreneacetyl group, 1-fluorenecarboxylic group, 9-fluorenecarboxylic group, 9-fluorenone-1-carboxylic group, Xanthyl (Xan), Trityl (Trt), 4-methyltrityl (Mtt), 4-methoxytrityl (Mmt), 4-methoxy-2,3,6-trimethylbenzenesulphonyl (Mtr), Mesitylene-2-sulphonyl (Mts), 4,4-dimethoxybenzhydryl (Mbh),Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimethyl-2,6-dioxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), Benzyloxymethyl (Bom), t-butoxycarbonyl (Boc), cyclohexyloxy (cHxO),t-butoxymethyl (Bum), t-butoxy (tBuO), t-Butyl (tBu), Acetyl (Ac), a carbobenzoxy group, a propyl group, a butyl group, a pentyl group, a hexyl group, and Trifluoroacetyl (TFA).

36. The method of claim 34, wherein said protecting group is a protecting group selected from the group consisting of acetyl, $CH_3—(CH_2)_n—CO—$ where n ranges from 1 to 20, and an amide.

37. The method of claim 34, wherein said peptide comprises a first protecting group coupled to the amino terminus and a second protecting group coupled to the carboxyl terminus.

38. The method of claim 26, wherein said oxidizing agent is selected from the group consisting of hydrogen peroxide, 13(S)-HPODE, 15(S)-HPETE, HPODE, HPETE, HODE, and HETE.

39. The method of claim 26, wherein said phospholipid is selected from the group consisting of 1-palmitoyl-2-arachidonoyl-sn-glycero-3-phosphorylcholine (PAPC), 1-stearoyl-2-arachidonoyl-sn-glycero-3-phosphorylcholine (SAPC)), and 1-stearoyl-2-arachidonyl-sn-glycero-3-phosphorylethanolamine (SAPE).

40. A kit for ameliorating a symptom of atherosclerosis, said kit comprising a container containing a peptide that:
ranges in length up to about 30 amino acids;
comprises at least one class A amphipathic helix;
protects a phospholid against oxidation by an oxidizing agent;
comprises the amino acid sequence D-W-F-K-A-F-Y-D-K-V-A-E-K-E-A-F (SEQ-ID-NO:5); and
bears at least one protecting group.

41. The kit of claim 40, wherein said peptide is combined with a pharmaceutically acceptable excipient in a unit dosage formulation.

42. The kit of claim 41, wherein said unit dosage formulation is for oral administration.

43. The kit of claim 40, further comprising instructional materials teaching the use of said peptide for ameliorating one or more symptoms of atherosclerosis.

44. The kit of claim 40, wherein said peptide comprises a protecting group coupled to the amino or carboxyl terminus.

45. The kit of claim 44, wherein said peptide comprises a protecting group coupled to the amino terminus and said amino terminal protecting group is a protecting group selected from the group consisting of a benzoyl group, an acetyl, a propionyl, a carbobenzoxy, a propyl, a butyl, a pentyl, a hexyl, and a 3 to 20 carbon alkyl.

46. The kit of claim 44, wherein said peptide comprises a protecting group coupled to the carboxyl terminus and said carboxyl terminal protecting group is an amide.

47. The kit of claim 44, wherein said peptide further comprises a first protecting group coupled to the amino terminus and a second protecting group coupled to the carboxyl terminus.

48. The kit of claim 44, wherein said peptide comprises:
a first protecting group coupled to the amino terminus wherein said protecting group is a protecting group selected from the group consisting of a benzoyl group, an acetyl, a propionyl, a carbobenzoxy, a propyl, a butyl, a pentyl, a hexyl, and a 3 to 20 carbon alkyl; and
a second protecting group coupled to the carboxyl terminus and said carboxyl terminal protecting group is an amide.

* * * * *

UNITED STATES PATENT AND TRADEMARK OFFICE
CERTIFICATE OF CORRECTION

PATENT NO.        : 6,933,279 B2                               Page 1 of 1
APPLICATION NO. : 09/896841
DATED             : August 23, 2005
INVENTOR(S)       : Fogelman et al.

It is certified that error appears in the above-identified patent and that said Letters Patent is hereby corrected as shown below:

CLAIMS:

In line 3 of claim 21 (column 89, line 4) change "$P^1$-D-W-F-K-A-F-Y-D-K-V-A-E-K-F-E-A-F-$P^2$" to --$P^1$-D-W-F-K-A-F-Y-D-K-V-A-E-K-F-K-E-A-F-$P^2$--.

In lines 7-8 of claim 40 (column 90, lines 28-29) change "D-W-F-K-A-F-Y-D-K-V-A-E-K-E-A-F" to --D-W-F-K-A-F-Y-D-K-V-A-E-K-F-K-E-A-F--.

Signed and Sealed this

Seventeenth Day of March, 2009

JOHN DOLL
*Acting Director of the United States Patent and Trademark Office*